United States Patent
Ng et al.

(10) Patent No.: US 7,566,733 B2
(45) Date of Patent: Jul. 28, 2009

(54) BENZIMIDAZOLE DERIVATIVES USEFUL AS SELECTIVE ANDROGEN RECEPTOR MODULATORS (SARMS)

(75) Inventors: Raymond Ng, Raritan, NJ (US); Zhihua Sui, Raritan, NJ (US); Jihua Guan, Raritan, NJ (US); James C. Lanter, Raritan, NJ (US); Vernon C. Alford, Jr., Raritan, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 69 days.

(21) Appl. No.: 11/235,024

(22) Filed: Sep. 26, 2005

(65) Prior Publication Data
US 2006/0116412 A1 Jun. 1, 2006

Related U.S. Application Data

(60) Provisional application No. 60/614,751, filed on Sep. 30, 2004.

(51) Int. Cl.
*A61K 31/4184* (2006.01)
*C07D 235/10* (2006.01)
*C07D 235/12* (2006.01)

(52) U.S. Cl. .................. 514/394; 548/309.7; 548/310.1
(58) Field of Classification Search ................. 514/394; 548/309.7, 310.1
See application file for complete search history.

(56) References Cited

U.S. PATENT DOCUMENTS

| 3,897,432 | A | | 7/1975 | Shen et al. |
| 3,987,182 | A | | 10/1976 | Gold et al. |
| 5,504,089 | A | * | 4/1996 | Russell ..................... 514/266.3 |

FOREIGN PATENT DOCUMENTS

| DE | 947610 | 8/1956 |
| EP | 0260744 A2 | 3/1988 |
| EP | 0625511 A1 | 11/1994 |
| GB | 1356736 | 6/1974 |
| JP | 05163246 A | 6/1993 |

OTHER PUBLICATIONS

Patani et al. "Bioisosterism: A Rational Approach in Drug Design" Chemical Reviews, 1996, vol. 96, pp. 3147-3176.*
PCT International Search Report for International Appln No. PCT/US2005/034462 dated Mar. 14, 2006.
Cuong, Luu Duc et al. "Some aspects of the chemistry of benzimidazoles: bisbenzimidazoles with antiallergic activity". Bulletin des Travaux de la Societe de Pharmacie de Lyon, 27(1), 3-11 Coden: Btslav; Issn: 0037-9107, 1983, XP000120180.
Popov, I.I., et al. "Investigations of Unsaturated Azoles. 15, Synthesis and Reactions of Acylated Benzimidazoles". Chemistry of Heterocyclic Compounds (A translation of Khimiya Geterotsiklicheskikh Soedinenii), XP000974045, Issn: 0009-3122.
Shazhenov, A.A., et al. "Condensation of aniline, o-phenylenediamine, and their derivatives with lactones". Khimiya Geterotsiklicheskikh Soedinenii, (5), 641-4 Coden: KGSSAQ: Issn: 0132-6244, 1972, XP009062926.
Alloum, A.B. et al.: "Synthese chimioselective des benzimidazoles sur silice traitee par le chlorure du thionyle", Tetrahedron Letters 44 (2003): 5935-5937. (Note: English-language abstract only).
Basaria, S. et al.: Anabolic-Androgenic Steroid Therapy in the Treatment of Chronic Diseases; The J. of Clin. Endocrinology & Metab (2001), 86(11), pp. 5108-5117.
Beaulieu, P.L. et al.: "A Practical Oxone® —Mediated, High-Throughput, Solution-Phase Synthesis of Benzimidazoles from 1,2-Phenylenediamines and Aldehydes and its Application to Preparative Scale Synthesis", Synthesis 2003, No. 11: 1683-1692.
Matsushita, H. et al.: "Smart cleavage reactions: the synthesis of benzimidazoles and benzothiazoles from polymer-bound esters", Tetrahedron Letters 45 (2004): 313-316.
Mayer, J.P. et al.: "Solid-Phase Synthesis of Benzimidazoles", Tetrahedron Letters 39 (1998): 6655-6658.
Newling, D.W.: Anti-androgens in the treatment of prostate cancer; Br. J. Urology (1996) 77(6), pp. 776-784.
Shahidi, N.T.: A Review of the Chemistry, Biological Action, and Clinical Applications of Anabolic-Androgenic Steroids; Clin. Therapeutics (2001), 23(9), pp. 1355-1390.

* cited by examiner

*Primary Examiner*—Rei-Tsang Shiao
*Assistant Examiner*—Joseph R Kosack
(74) *Attorney, Agent, or Firm*—Timothy E. Tracy

(57) ABSTRACT

The present invention is directed to novel benzimidazole derivatives, pharmaceutical compositions containing them and their use in the treatment of disorders and conditions modulated by the androgen receptor.

3 Claims, No Drawings

BENZIMIDAZOLE DERIVATIVES USEFUL AS SELECTIVE ANDROGEN RECEPTOR MODULATORS (SARMS)

CROSS REFERENCE TO RELATED APPLICATIONS

This application claims the benefit of U.S. Provisional Application 60/614,751, filed on Sep. 30, 2004, which is incorporated by reference herein in its entirety.

FIELD OF THE INVENTION

The present invention is directed to novel benzimidazole derivatives, pharmaceutical compositions containing them and their use in the treatment of disorders and conditions modulated by the androgen receptor. More particularly, the compounds of the present invention are useful in the treatment of prostate carcinoma, benign prostatic hyperplasia (BPH), hirsutism, alopecia, anorexia nervosa, breast cancer, acne, AIDS, cachexia, as a male contraceptive, and/or as a male performance enhancer.

BACKGROUND OF THE INVENTION

Androgens are the anabolic steroid hormones of animals, controlling muscle and skeletal mass, the maturation of the reproductive system, the development of secondary sexual characteristics and the maintenance of fertility in the male. In women, testosterone is converted to estrogen in most target tissues, but androgens themselves may play a role in normal female physiology, for example, in the brain. The chief androgen found in serum is testosterone, and this is the effective compound in tissues such as the testes and pituitary. In prostate and skin, testosterone is converted to dihydrotestosterone (DHT) by the action of 5α-reductase. DHT is a more potent androgen than testosterone because it binds more strongly to the androgen receptor.

Like all steroid hormones, androgens bind to a specific receptor inside the cells of target tissues, in this case the androgen receptor. This is a member of the nuclear receptor transcription factor family. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Although modulators of androgen receptor function have been employed clinically for some time, both the steroidal (Basaria, S., Wahlstrom, J. T., Dobs, A. S., *J. Clin Endocrinol Metab* (2001), 86, pp 5108-5117; Shahidi, N. T., *Clin Therapeutics*, (2001), 23, pp 1355-1390), and non-steroidal (Newling, D. W., *Br. J. Urol.*, 1996, 77 (6), pp 776-784) compounds have significant liabilities related to their pharmacological parameters, including gynecomastia, breast tenderness and hepatoxicity. In addition, drug-drug interactions have been observed in patients receiving anticoagulation therapy using coumarins. Finally, patients with aniline sensitivities could be compromised by the metabolites of non-steroidal antiandrogens.

Non-steroidal agonists and antagonists of the androgen receptor are useful in the treatment of a variety of disorders and diseases. More particularly, agonists of the androgen receptor could be employed in the treatment of prostate cancer, benign prostatic hyperplasia, hirsutism in women, alopecia, anorexia nervosa, breast cancer and acne. Antagonists of the androgen receptor could be employed in male contraception, male performance enhancement, as well as in the treatment of cancer, AIDS, cachexia, and other disorders.

Nonetheless, there exists a need for small molecule, non-steroidal agonist and/or antagonists of the androgen receptor. We now describe a novel series of benzimidazole derivatives as androgen receptor modulators.

SUMMARY OF THE INVENTION

The present invention is directed to compounds of formula (I)

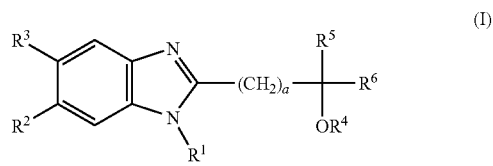

wherein $R^1$ is selected from the group consisting of hydrogen, $C_{1-4}$alkyl, —$C_{1-4}$alkyl-OH, —$C_{1-4}$alkyl-CN, —$C_{1-4}$alkyl-NO$_2$, —$C_{1-4}$alkyl-N($R^A R^B$), —$C_{1-4}$alkyl-CO$_2$H, —($C_{1-4}$alkyl)-X—$R^7$, —CH$_2$-aryl and —CH$_2$-heteroaryl; wherein the aryl or heteroaryl group (on the —CH$_2$-aryl and —CH$_2$-heteroaryl group) is optionally substituted with one or more substituents independently selected from halogen, $C_{1-4}$alkyl, halogen substituted $C_{1-4}$alkyl, $C_{1-4}$alkoxy, halogen substituted $C_{1-4}$alkoxy, —$C_{1-4}$alkyl-CN, —$C_{1-4}$alkyl-OH, cyano, nitro, amino, $C_{1-4}$alkylamino, di($C_{1-4}$alkyl)amino, —S—$C_{1-4}$ alkyl, —S-(halogen substituted $C_{1-4}$alkyl), —SO—$C_{1-4}$alkyl, —SO$_2$—$C_{1-4}$alkyl, —O-aralkyl, —C(O)O—$C_{1-4}$alkyl, —CO$_2$H, —C(O)H, heteroaryl or heterocycloalkyl;

wherein $R^A$ and $R^B$ are independently selected from hydrogen or $C_{1-4}$alkyl; alternatively, $R^A$ and $R^B$ are taken together with the nitrogen atom to which they are bound to form a five to seven membered aromatic, partially unsaturated or saturated ring structure, optionally containing one to two additional heteroatoms selected from O, S or N; and wherein the ring structure is optionally substituted with $C_{1-4}$alkyl;

wherein X is selected from the group consisting of —S—, —SO—, SO$_2$—, —O—SO$_2$—, —O—, —C(OH)—, —C(=N(OH))—, —C(O)—, —C(O)—O—, —NR$^C$—, —NR$^C$—C(O)—, —C(O)—NR$^C$—, —NR$^C$—SO$_2$— and —SO$_2$—NR$^C$—; wherein R$^C$ is selected from hydrogen or $C_{1-4}$alkyl;

wherein $R^7$ is selected from the group consisting of $C_{1-4}$alkyl, halogen substituted $C_{1-4}$alkyl, $C_{2-4}$alkenyl, aryl, aralkyl, biphenyl, cycloalkyl, cycloalkyl-($C_{1-4}$alkyl)-, heteroaryl, heteroaryl-($C_{1-4}$alkyl)-, heterocycloalkyl and heterocycloalkyl-($C_{1-4}$alkyl)-; wherein the cycloalkyl, aryl, heteroaryl or heterocycloalkyl group, whether alone or as part of a substituent group is optionally substituted with one or more substituents independently selected from halogen, hydroxy, carboxy, $C_{1-4}$alkyl, halogen substituted $C_{1-4}$alkyl, $C_{1-4}$alkoxy, halogen substituted $C_{1-4}$alkoxy, cyano, nitro, amino, $C_{1-4}$alkylamino, di($C_{1-4}$alkyl)amino, —S(O)$_{0-2}$—($C_{1-4}$alkyl), —SO$_2$—N($R^D$)$_2$, aryl, heteroaryl or heterocycloalkyl; wherein each $R^D$ is independently selected from hydrogen or $C_{1-4}$alkyl;

provided that when X is O or NR$^C$, then $R^6$ is other than $C_{2-4}$alkenyl;

$R^2$ is selected from the group consisting of hydrogen, halogen, $C_{1-4}$alkyl, halogen substituted $C_{1-4}$alkyl, cyano, nitro, amino, $C_{1-4}$alkylamino, di($C_{1-4}$alkyl)amino, —O—$C_{1-4}$alkyl, —S—$C_{1-4}$alkyl, —SO—$C_{1-4}$alkyl, —$SO_2$—$C_{1-4}$alkyl and —$NR^E$—C(O)—$C_{1-4}$alkyl; wherein $R^E$ is selected from hydrogen or $C_{1-4}$alkyl;

$R^3$ is selected from the group consisting of hydrogen, halogen, $C_{1-4}$alkyl, halogen substituted $C_{1-4}$alkyl, cyano, nitro, amino, $C_{1-4}$alkylamino, di($C_{1-4}$alkyl)amino, —O—$C_{1-4}$alkyl, —S—$C_{1-4}$alkyl, —SO—$C_{1-4}$alkyl, —$SO_2$—$C_{1-4}$alkyl and —$NR^F$—C(O)—$C_{1-4}$alkyl; wherein $R^F$ is selected from hydrogen or $C_{1-4}$alkyl;

provided that at least one of $R^2$ or $R^3$ is other than hydrogen;

a is an integer from 0 to 1;

$R^4$ is selected from the group consisting of hydrogen, $C_{1-4}$alkyl, halogen substituted $C_{1-4}$alkyl and —C(O)—$R^8$;

wherein $R^8$ is selected from the group consisting of $C_{1-4}$alkyl, cycloalkyl, cycloalkyl-($C_{1-4}$alkyl)-, aryl, aralkyl, heteroaryl, heteroaryl-($C_{1-4}$alkyl)-, heterocycloalkyl and heterocycloalkyl-($C_{1-4}$alkyl)-; wherein the alkyl, cycloalkyl, aryl, heteroaryl or heterocycloalkyl group, whether alone or as part of a substituent group is optionally substituted with one or more substituents independently selected from halogen, hydroxy, carboxy, $C_{1-4}$alkyl, halogen substituted $C_{1-4}$alkyl, $C_{1-4}$alkoxy, halogen substituted $C_{1-4}$alkoxy, cyano, nitro, amino, $C_{1-4}$alkylamino or di($C_{1-4}$alkyl)amino;

$R^5$ is selected from the group consisting of hydrogen, halogen, $C_{1-4}$alkyl and halogen substituted $C_{1-4}$alkyl;

$R^6$ is selected from the group consisting of $C_{1-4}$alkyl, halogen substituted $C_{1-4}$alkyl, —$C_{1-4}$alkyl-OH, —$C_{1-4}$alkyl-CN, —$C_{1-4}$alkyl-$NO_2$, —$C_{1-4}$alkyl-N($R^G R^H$), $C_{1-4}$alkyl-$CO_2H$, —($C_{1-4}$alkyl)-Y—$R^9$, —$CH_2$-aryl and —$CH_2$-heteroaryl; wherein the aryl or heteroaryl (on the —$CH_2$-aryl or —$CH_2$-heteroaryl group) is optionally substituted with one or more substituents independently selected from halogen, hydroxy, $C_{1-4}$alkyl, halogen substituted $C_{1-4}$alkyl, $C_{1-4}$alkoxy, halogen substituted $C_{1-4}$alkoxy, cyano, nitro, amino, $C_{1-4}$alkylamino, di($C_{1-4}$alkyl)amino, —$S(O)_{0-2}$—$C_{1-4}$alkyl or —$SO_2$—N($R^J$)$_2$; wherein each $R^J$ is independently selected from hydrogen or $C_{1-4}$alkyl;

wherein $R^G$ and $R^H$ are independently selected from hydrogen or $C_{1-4}$alkyl; alternatively, $R^G$ and $R^H$ are taken together with the nitrogen atom to which they are bound to form a five to seven membered aromatic, partially unsaturated or saturated ring structure, optionally containing one to two additional heteroatoms selected from O, S or N; and wherein the ring structure is optionally substituted with $C_{1-4}$alkyl;

wherein Y is selected from the group consisting of —S—, —SO—, $SO_2$—, —O—$SO_2$—, —O—, —C(OH)—, —C(=N(OH))—, —C(O)—, —C(O)—O—, —$NR^K$, —$NR^K$—C(O)—, —C(O)—$NR^K$—, —$NR^K$—$SO_2$— and —$SO_2$—$NR^K$—; wherein $R^K$ is selected from hydrogen or $C_{1-4}$alkyl;

wherein $R^9$ is selected from the group consisting of $C_{1-4}$alkyl, halogen substituted $C_{1-4}$alkyl, $C_{2-4}$alkenyl, aryl, aralkyl, biphenyl, cycloalkyl, cycloalkyl-($C_{1-4}$alkyl)-, heteroaryl, heteroaryl-($C_{1-4}$alkyl)-, heterocycloalkyl and heterocycloalkyl-($C_{1-4}$alkyl)-; wherein the cycloalkyl, aryl, heteroaryl or heterocycloalkyl group, whether alone or as part of a substituent group is optionally substituted with one or more substituents independently selected from halogen, hydroxy, carboxy, $C_{1-4}$alkyl, halogen substituted $C_{1-4}$alkyl, $C_{1-4}$alkoxy, halogen substituted $C_{1-4}$alkoxy, cyano, nitro, amino, $C_{1-4}$alkylamino, di($C_{1-4}$alkyl)amino, —$S(O)_{0-2}$—($C_{1-4}$alkyl), —$SO_2$—N($R^L$)$_2$ or —$NR^M$—C(O)—$C_{1-4}$alkyl;

wherein each $R^L$ is independently selected from hydrogen or $C_{1-4}$alkyl; and wherein $R^M$ is selected from hydrogen or $C_{1-4}$alkyl;

provided that when Y is O or $NR^K$, then $R^9$ is other than $C_{2-4}$alkenyl;

provided that when $R^4$ is hydrogen and $R^5$ is hydrogen, then $R^6$ is other than $C_{1-4}$alkyl;

provided further that when $R^1$ is hydrogen; a is 0; $R^4$ is hydrogen and $R^5$ is $C_{1-4}$alkyl; then $R^6$ is other than $C_{1-4}$alkyl;

provided further that when $R^1$ is hydrogen; a is 0; $R^2$ is —O—$C_{1-4}$alkyl; $R^3$ is hydrogen; $R^4$ is hydrogen; $R^5$ is hydrogen; then $R^6$ is other than —$CH_2$-phenyl, wherein the phenyl is substituted with —O—$C_{1-4}$alkyl;

provided further that when $R^1$ is hydrogen, a is 0, $R^4$ is hydrogen and $R^5$ is hydrogen; then $R^6$ is other than —$CH_2$-(benzimidazolyl), wherein the benzimidazolyl is substituted with one to two substituents selected from halogen, $C_{1-4}$alkyl or —O—$C_{1-4}$alkyl;

or a pharmaceutically acceptable salt thereof.

The present invention is further directed to compounds of formula (II)

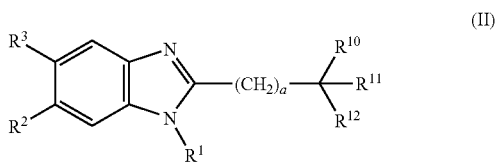

(II)

wherein $R^1$ is selected from the group consisting of hydrogen, $C_{1-4}$alkyl, —$C_{1-4}$alkyl-OH, —$C_{1-4}$alkyl-CN, —$C_{1-4}$alkyl-$NO_2$, —$C_{1-4}$alkyl-N($R^A R^B$), —$C_{1-4}$alkyl-$CO_2H$, —($C_{1-4}$alkyl)-X—$R^7$, —$CH_2$-aryl and —$CH_2$-heteroaryl; wherein the aryl or heteroaryl group (on the —$CH_2$-aryl and —$CH_2$-heteroaryl group) is optionally substituted with one or more substituents independently selected from halogen, $C_{1-4}$alkyl, halogen substituted $C_{1-4}$alkyl, $C_{1-4}$alkoxy, halogen substituted $C_{1-4}$alkoxy, —$C_{1-4}$alkyl-CN, —$C_{1-4}$alkyl-OH, cyano, nitro, amino, $C_{1-4}$alkylamino, di($C_{1-4}$alkyl)amino, —S—$C_{1-4}$ alkyl, —S-(halogen substituted $C_{1-4}$alkyl), —SO—$C_{1-4}$alkyl, —$SO_2$—$C_{1-4}$alkyl, —O-aralkyl, —C(O)O—$C_{1-4}$alkyl, —$CO_2H$, —C(O)H, heteroaryl or heterocycloalkyl;

wherein $R^A$ and $R^B$ are independently selected from hydrogen or $C_{1-4}$alkyl; alternatively, $R^A$ and $R^B$ are taken together with the nitrogen atom to which they are bound to form a five to seven membered aromatic, partially unsaturated or saturated ring structure, optionally containing one to two additional heteroatoms selected from O, S or N; and wherein the ring structure is optionally substituted with $C_{1-4}$alkyl;

wherein X is selected from the group consisting of —S—, —SO—, $SO_2$—, —O—$SO_2$—, —O—, —C(OH)—, —C(=N(OH))—, —C(O)—, —C(O)—O—, —$NR^C$—, —$NR^C$—C(O)—, —C(O)—$NR^C$—, —$NR^C$—$SO_2$— and —$SO_2$—$NR^C$—; wherein $R^C$ is selected from hydrogen or $C_{1-4}$alkyl;

wherein $R^7$ is selected from the group consisting of $C_{1-4}$alkyl, halogen substituted $C_{1-4}$alkyl, $C_{2-4}$alkenyl, aryl, aralkyl, biphenyl, cycloalkyl, cycloalkyl-($C_{1-4}$alkyl)-, heteroaryl, heteroaryl-($C_{1-4}$alkyl)-, heterocycloalkyl and heterocycloalkyl-($C_{1-4}$alkyl)-; wherein the cycloalkyl, aryl, heteroaryl or heterocycloalkyl group, whether alone or as part of a substituent group is optionally substituted with one or more substituents independently selected from halogen, hydroxy, carboxy, $C_{1-4}$alkyl, halogen substituted $C_{1-4}$alkyl, $C_{1-4}$alkoxy, halogen substituted $C_{1-4}$alkoxy, cyano, nitro, amino, $C_{1-4}$alkylamino, di($C_{1-4}$alkyl)amino, —S(O)$_{0-2}$—($C_{1-4}$alkyl), —SO$_2$—N(R$^D$)$_2$, aryl, heteroaryl or heterocycloalkyl; wherein each R$^D$ is independently selected from hydrogen or $C_{1-4}$alkyl;

provided that when X is O or NR$^C$, then R$^6$ is other than C$_{2-4}$alkenyl;

R$^2$ is selected from the group consisting of hydrogen, halogen, $C_{1-4}$alkyl, halogen substituted $C_{1-4}$alkyl, cyano, nitro, amino, $C_{1-4}$alkylamino, di($C_{1-4}$alkyl)amino, —O—($C_{1-4}$alkyl, —S—$C_{1-4}$alkyl, —SO—$C_{1-4}$alkyl, —SO$_2$—$C_{1-4}$alkyl and —NR$^E$—C(O)—$C_{1-4}$alkyl; wherein R$^E$ is selected from hydrogen or $C_{1-4}$alkyl;

R$^3$ is selected from the group consisting of hydrogen, halogen, $C_{1-4}$alkyl, halogen substituted $C_{1-4}$alkyl, cyano, nitro, amino, $C_{1-4}$alkylamino, di($C_{1-4}$alkyl)amino, —O—($C_{1-4}$alkyl, —S—$C_{1-4}$alkyl, —SO—($C_{1-4}$alkyl, —SO$_2$—$C_{1-4}$alkyl and —NR$^F$—C(O)—$C_{1-4}$alkyl; wherein R$^F$ is selected from hydrogen or $C_{1-4}$alkyl;

provided that at least one of R$^2$ or R$^3$ is other than hydrogen;

a is an integer from 0 to 1;

R$^{10}$ is selected from the group consisting of hydrogen, halogen, $C_{1-4}$alkyl, halogen substituted $C_{1-4}$alkyl and —O—C(O)—R$^8$;

wherein R$^8$ is selected from the group consisting of $C_{1-4}$alkyl, cycloalkyl, cycloalkyl-($C_{1-4}$alkyl)-, aryl, aralkyl, heteroaryl, heteroaryl-($C_{1-4}$alkyl)-, heterocycloalkyl and heterocycloalkyl-($C_{1-4}$alkyl)-; wherein the alkyl, cycloalkyl, aryl, heteroaryl or heterocycloalkyl group, whether alone or as part of a substituent group is optionally substituted with one or more substituents independently selected from halogen, hydroxy, carboxy, $C_{1-4}$alkyl, halogen substituted $C_{1-4}$alkyl, $C_{1-4}$alkoxy, halogen substituted $C_{1-4}$alkoxy, cyano, nitro, amino, $C_{1-4}$alkylamino or di($C_{1-4}$alkyl)amino;

R$^{11}$ is selected from the group consisting of hydrogen and halogen;

alternatively, R$^{10}$ and R$^{11}$ are taken together with the carbon atom to which they are abound to form —C(O)—, C=N(OH) or —C=N(O—$C_{1-4}$alkyl);

R$^{12}$ is selected from the group consisting of $C_{1-4}$alkyl, halogen substituted $C_{1-4}$alkyl, —$C_{1-4}$alkyl-OH, —$C_{1-4}$alkyl-CN, —$C_{1-4}$alkyl-NO$_2$, —$C_{1-4}$alkyl-N(R$^G$R$^H$), $C_{1-4}$alkyl-CO$_2$H, —($C_{1-4}$alkyl)-Y—R$^9$, —CH$_2$-aryl and —CH$_2$-heteroaryl; wherein the aryl or heteroaryl (on the —CH$_2$-aryl or —CH$_2$-heteroaryl group) is optionally substituted with one or more substituents independently selected from halogen, hydroxy, $C_{1-4}$alkyl, halogen substituted $C_{1-4}$alkyl, $C_{1-4}$alkoxy, halogen substituted C-4alkoxy, cyano, nitro, amino, $C_{1-4}$alkylamino, di($C_{1-4}$alkyl)amino, —S(O)$_{0-2}$—$C_{1-4}$ alkyl or —SO$_2$—N(R$^J$)$_2$; wherein each R$^J$ is independently selected from hydrogen or $C_{1-4}$alkyl;

wherein R$^G$ and R$^H$ are independently selected from hydrogen or $C_{1-4}$alkyl; alternatively, R$^G$ and R$^H$ are taken together with the nitrogen atom to which they are bound to form a five to seven membered aromatic, partially unsaturated or saturated ring structure, optionally containing one to two additional heteroatoms selected from O, S or N; and wherein the ring structure is optionally substituted with $C_{1-4}$alkyl;

wherein Y is selected from the group consisting of —S—, —SO—, SO$_2$—, —O—SO$_2$—, —O—, —C(OH)—, —C(=N(OH))—, —C(O)—, —C(O)—O—, —NR$^K$—, NR$^K$—C(O)—, —C(O)—NR$^K$—, —NR$^K$—SO$_2$— and —SO$_2$—NR$^K$—; wherein R$^K$ is selected from hydrogen or $C_{1-4}$alkyl;

wherein R$^9$ is selected from the group consisting of $C_{1-4}$alkyl, halogen substituted $C_{1-4}$alkyl, $C_{2-4}$alkenyl, aryl, aralkyl, biphenyl, cycloalkyl, cycloalkyl-($C_{1-4}$alkyl)-, heteroaryl, heteroaryl-($C_{1-4}$alkyl)-, heterocycloalkyl and heterocycloalkyl-($C_{1-4}$alkyl)-; wherein the cycloalkyl, aryl, heteroaryl or heterocycloalkyl group, whether alone or as part of a substituent group is optionally substituted with one or more substituents independently selected from halogen, hydroxy, carboxy, $C_{1-4}$alkyl, halogen substituted $C_{1-4}$alkyl, $C_{1-4}$alkoxy, halogen substituted $C_{1-4}$alkoxy, cyano, nitro, amino, $C_{1-4}$alkylamino, di($C_{1-4}$alkyl)amino, —S(O)$_{0-2}$—($C_{1-4}$alkyl), —SO$_2$—N(R$^L$)$_2$ or —NR$^M$—C(O)—$C_{1-4}$alkyl; wherein each R$^L$ is independently selected from hydrogen or $C_{1-4}$alkyl; and wherein R$^M$ is selected from hydrogen or $C_{1-4}$alkyl;

provided that when Y is O or NR$^K$, then R$^9$ is other than C$_{2-4}$alkenyl;

provided that when R$^1$ is —CH$_2$-phenyl wherein the phenyl is substituted with —C(O)O—$C_{1-4}$alkyl or —CO$_2$H; R$^2$ is methyl; R$^3$ is methyl; a is 0; R$^{10}$ is hydrogen; and R$^{11}$ is hydrogen; then R$^{12}$ is other than —CH$_2$-phenyl;

provided further that when R$^1$ is —CH$_2$-phenyl wherein the phenyl is substituted with —C(O)O—$C_{1-4}$alkyl or —CO$_2$H; R$^2$ and R$^3$ are selected to be (H and fluoro), (fluoro and H), (methyl, methyl) or (H and trifluoromethyl); a is an integer form 0 to 1; R$^{10}$ is hydrogen; and R$^{11}$ is hydrogen; then R$^{12}$ is other than $C_{1-4}$alkyl;

provided further that when R$^1$ is hydrogen or $C_{1-4}$alkyl; a is 0; R$^{10}$ and R$^{11}$ are taken together with the carbon atom to which they are abound to form —C(O)—, one of R$^2$ or R$^3$ is hydrogen and the other of R$^2$ or R$^3$ is selected from halogen, $C_{1-4}$alkyl, —O—$C_{1-4}$alkyl or nitro, then R$^{12}$ is other than $C_{1-4}$alkyl, $C_{1-4}$alkyl substituted with one halogen or benzyl;

provided further that when R$^1$ is —CH$_2$-phenyl; a is 0; R$^{10}$ and R$^{11}$ are taken together with the carbon atom to which they are abound to form —C(O)—, of R$^2$ is hydrogen; and R$^3$ is nitro, then R$^{12}$ is other than $C_{1-4}$alkyl;

provided further that when R$^1$ is hydrogen; a is 0; R$^2$ is —O—$C_{1-4}$alkyl, R$^3$ is —O—$C_{1-4}$alkyl; and R$^{10}$ and R$^{11}$ are taken together with the carbon atom to which they are abound to form —C(O)—; then R$^{12}$ is other than benzyl;

provided further that when R$^1$ is —$C_{1-4}$alkyl-N($C_{1-4}$alkyl)$_2$; a is 0; R$^2$ is —O—$C_{1-4}$alkyl; R$^3$ is —O—$C_{1-4}$alkyl; and R$^{10}$ and R$^{11}$ are taken together with the carbon atom to which they are abound to form —C(O)—, then R$^{12}$ is other than benzyl, wherein the benzyl is substituted with a halogen;

or a pharmaceutically acceptable salt thereof.

Illustrative of the invention is a pharmaceutical composition comprising a pharmaceutically acceptable carrier and any of the compounds described herein. An illustration of the invention is a pharmaceutical composition made by mixing any of the compounds described herein and a pharmaceutically acceptable carrier. Illustrating the invention is a process for making a pharmaceutical composition comprising mixing any of the compounds described herein and a pharmaceutically acceptable carrier.

Exemplifying the invention are methods of treating disorders and conditions modulated by the androgen receptor in a subject in need thereof comprising administering to the subject a therapeutically effective amount of any of the compounds or pharmaceutical compositions described herein.

An example of the invention is a method for treating an androgen receptor modulated disorder selected from the group consisting of prostate carcinoma, benign prostatic hyperplasia, hirsutism, or for male contraception, in a subject in need thereof comprising administering to the subject an effective amount of any of the compounds or pharmaceutical compositions described herein.

Another example of the invention is the use of any of the compounds described herein in the preparation of a medicament for treating: (a) prostate carcinoma, (b) benign prostatic hyperplasia, (c) hirsutism, (d) alopecia, (e) anorexia nervosa, (f) breast cancer, (g) acne, (h) AIDS, (i) cachexia, for (j) male contraception, or for (k) male performance enhancement, in a subject in need thereof.

DETAILED DESCRIPTION OF THE INVENTION

The present invention is directed to compounds of formula (I) and compounds of formula (II)

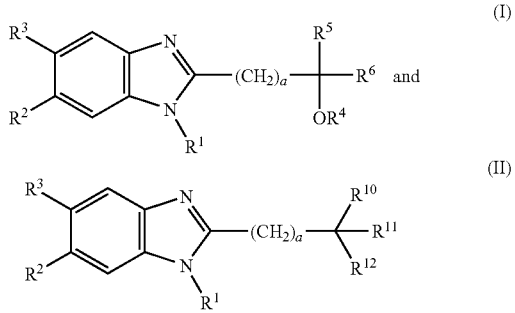

wherein $R^1$, $R^2$, $R^3$, a, $R^4$, $R^5$, $R^6$, $R^{10}$, $R^{11}$ and $R^{12}$ are as herein defined, useful as selective androgen receptor modulators for the treatment of prostate carcinoma, benign prostatic hyperplasia (BPH), hirsutism, alopecia, anorexia nervosa, breast cancer, acne, AIDS, cachexia, as a male contraceptive, and/or as a male performance enhancer. One skilled in the art will recognize that some compounds of formula (I) may be metabolites of the corresponding compounds of formula (II).

One skilled in the art will recognize that some of the variables (e.g. $R^1$, $R^2$, $R^3$, a, etc.) appear in compounds of formula (I) and compounds of formula (II). One skilled in the art will further recognize that wherein a particular substituent is selected for a given variable for a compound of formula (I), said selection is not intended to limit the scope of said variable for compounds of formula (II). Similarly, the selection of a particular substituent for a given variable for a compound of formula (II), is not intended to limit the scope of said variable for compounds of formula (I).

In an embodiment of the present invention, $R^1$ is selected from the group consisting of hydrogen, $C_{1-4}$alkyl, —$C_{1-4}$alkyl-OH, —$C_{1-4}$alkyl-CN, —$C_{1-4}$alkyl-X—$R^7$, —$CH_2$-phenyl and —$CH_2$-heteroaryl; wherein the phenyl or heteroaryl (on the —$CH_2$-phenyl or —$CH_2$-heteroaryl group) is optionally substituted with one or more substituents independently selected from halogen, $C_{1-4}$alkyl, —O—$C_{1-4}$alkyl, halogen substituted $C_{1-4}$alkyl, —O-(halogen substituted $C_{1-4}$alkyl), —$C_{1-4}$alkyl-CN, nitro, cyano, —S-(halogen substituted $C_{1-4}$alkyl), —$SO_2$—$C_{1-4}$alkyl, —O—$CH_2$-phenyl, —C(O)O—$C_{1-4}$alkyl, —C(O)H, heteroaryl or heterocycloalkyl.

In another embodiment of the present invention, $R^1$ is selected from the group consisting of hydrogen, $C_{1-4}$alkyl, —$C_{1-4}$alkyl-OH, —$C_{1-4}$alkyl-CN, —$C_{1-4}$alkyl-X—$R^7$, —$CH_2$-phenyl and —$CH_2$-heteroaryl; wherein the phenyl or heteroaryl (on the —$CH_2$-phenyl or —$CH_2$-heteroaryl group) is optionally substituted with one or more substituents independently selected from halogen, $C_{1-4}$alkyl, —O—$C_{1-4}$alkyl, halogen substituted $C_{1-4}$alkyl, —O-(halogen substituted $C_{1-4}$alkyl), —$C_{1-4}$alkyl-CN, nitro, cyano, —S-(halogen substituted $C_{1-4}$alkyl), —$SO_2$—$C_{1-4}$alkyl, —O—$CH_2$-phenyl, —C(O)O—$C_{1-4}$alkyl, —C(O)H, heteroaryl or heterocycloalkyl.

In another embodiment of the present invention, $R^1$ is selected from the group consisting of hydrogen, —$C_{1-4}$alkyl, —$C_{1-4}$alkyl-CN, —$C_{1-4}$alkyl-O—$C_{1-4}$alkyl and —$C_{1-4}$alkyl-S(O)$_{0-2}$—$C_{1-4}$alkyl.

In another embodiment of the present invention, $R^1$ is selected from the group consisting of hydrogen, $C_{1-2}$alkyl, —$C_{1-2}$alkyl-OH, —$C_{1-2}$alkyl-CN, —$C_{1-2}$alkyl-O—$C_{1-2}$alkyl and —$C_{1-2}$alkyl-S(O)$_{0-2}$—$C_{1-2}$alkyl.

In another embodiment of the present invention, $R^1$ is selected from the group consisting of hydrogen, —$CH_2$-heteroaryl and —$C_{1-2}$alkyl-X—$R^7$.

In another embodiment of the present invention, $R^1$ is selected from the group consisting of hydrogen, —$CH_2$-heteroaryl and —$CH_2$—C(O)-heteroaryl.

In another embodiment of the present invention, $R^1$ is selected from the group consisting of hydrogen, methyl, ethyl, n-propyl, n-butyl, cyano-methyl, methoxy-methyl and methyl-thio-methyl.

In another embodiment of the present invention, $R^1$ is selected from the group consisting of hydrogen, methyl, 2-hydroxyethyl-, 2-hydroxy-n-butyl-, cyano-methyl-, methoxy-methyl-, methyl-thio-methyl-, methyl-sulfonyl-methyl-, 4-chlorophenyl-sulfonyl-methyl-, ethoxy-carbonyl-methyl-, ethyl-carbonyl-methyl-, phenyl-carbonyl-methyl-, 4-fluorophenyl-carbonyl-methyl-, 4-bromophenyl-carbonyl-methyl-, 4-chlorophenyl-carbonyl-methyl-, 3-nitrophenyl-carbonyl-methyl-, 4-nitrophenyl-carbonyl-methyl-, 2-methoxyphenyl-carbonyl-methyl-, 3-methoxyphenyl-carbonyl-methyl-, 2,4-dimethoxyphenyl-carbonyl-methyl-, 2-benzofuryl-carbonyl-methyl-, 2-thienyl-carbonyl-methyl-, 2-pyridyl-carbonyl-methyl-, 3-pyridyl-carbonyl-methyl-, 2-(5-(2-pyridyl)-thienyl)-carbonyl-methyl-, 5-(2,3-dihydrobenzo[1,4]dioxinyl)-carbonyl-methyl-, 3-phenyl-5-methyl-isoxazol-4-yl-carbonyl-methyl-, 4-fluorophenoxy-ethyl-, 4-chlorophenoxy-ethyl-, 3-fluorophenoxy-ethyl-, 4-cyanophenoxy-ethyl-, 4-benzaldehyde, benzyl, 2-chlorobenzyl, 3-chlorobenzyl, 4-chlorobenzyl, 2-fluorobenzyl, 3-fluorobenzyl, 4-fluorobenzyl, 2-bromobenzyl, 4-bromobenzyl, 3-methoxybenzyl, 4-methoxybenzyl, 3-methylbenzyl, 3-trifluoromethylbenzyl, 4-trifluoromethylbenzyl, 3-trifluoromethoxybenzyl, 4-trifluoromethoxybenzyl, 2,3,4,5,6-pentafluorobenzyl, 2-cyanomethylbenzyl, 3-cyanomethylbenzyl, 2-methoxy-5-nitro-benzyl, 4-cyanobenzyl, 2-nitrobenzyl, 3-nitrobenzyl, 4-nitrobenzyl, 4-trifluoromethylthio-benzyl, 4-methylsulfonyl-benzyl, 4-benzyloxy-benzyl, 4-ethoxycarbonyl-benzyl, 4-pyrazolyl-benzyl, 4-[1,2,3]-thiadiazol-4-yl-benzyl, 4-pyrrolyl-benzyl, 3-(5-methyl-isoxazolyl)-methyl-, 2-pyridyl-methyl-, 3-pyridyl-methyl-, 4-pyridyl-methyl- and trans-butan-2-one oxime.

In another embodiment of the present invention, $R^1$ is selected from the group consisting of hydrogen and methoxymethyl-.

In another embodiment of the present invention, $R^1$ is hydrogen.

In an embodiment of the present invention, X is selected from the group consisting of —O—, S—, —SO—, —$SO_2$—, —C(O)—, —C(O)O— and —C(=N(OH))—.

In another embodiment of the present invention, X is selected from the group consisting of —O—, —S—, —$SO_2$— and —C(O)—.

In another embodiment of the present invention, X is selected from the group consisting of —O—, —S— and —SO$_2$—.

In an embodiment of the present invention, R$^7$ is selected from the group consisting of C$_{1-4}$alkyl, phenyl, —CH$_2$-phenyl, heteroaryl and heterocycloalkyl; wherein the phenyl or heteroaryl, whether alone or as part of a substituent group, is optionally substituted with one or more substituents independently selected from halogen, cyano, nitro, —C$_{1-4}$alkyl, —O—C$_{1-4}$alkyl, phenyl or heteroaryl.

In another embodiment of the present invention, R$^7$ is selected from the group consisting of C$_{1-4}$alkyl, halogen substituted C$_{1-4}$alkyl, phenyl, benzyl and heteroaryl; wherein the phenyl or heteroaryl is optionally substituted with one to two substituents independently selected from halogen, C$_{1-2}$alkyl, —O—C$_{1-2}$alkyl, halogen substituted C$_{1-2}$alkyl, nitro or cyano.

In an embodiment of the present invention, R$^2$ is selected from the group consisting of hydrogen, halogen, C$_{1-4}$alkyl, halogen substituted C$_{1-4}$alkyl, —O—C$_{1-4}$alkyl, cyano and nitro.

In another embodiment of the present invention, R$^2$ is selected from the group consisting of hydrogen, halogen, C$_{1-4}$alkyl, halogen substituted C$_{1-4}$alkyl, —O—C$_{1-4}$alkyl and nitro.

In another embodiment of the present invention, R$^2$ is selected from the group consisting of halogen, —C$_{1-4}$alkyl, halogen substituted C$_{1-4}$alkyl, —O—C$_{1-4}$alkyl, cyano and nitro.

In another embodiment of the present invention, R$^2$ is selected from the group consisting of halogen, C$_{1-4}$alkyl and halogen substituted C$_{1-4}$alkyl.

In another embodiment of the present invention, R$^2$ is halogen.

In another embodiment of the present invention, R$^2$ is selected from the group consisting of hydrogen, chloro, fluoro, methyl, trifluoromethyl, methoxy and nitro.

In another embodiment of the present invention, R$^2$ is selected from the group consisting of chloro and trifluoromethyl.

In another embodiment of the present invention, R$^2$ is selected from the group consisting of fluoro, chloro and methyl.

In an embodiment of the present invention, R$^3$ is selected from the group consisting of hydrogen, halogen, C$_{1-4}$alkyl, halogen substituted C$_{1-4}$alkyl, —O—C$_{1-4}$alkyl, cyano and nitro.

In another embodiment of the present invention, R$^3$ is selected from the group consisting of halogen, C$_{1-4}$alkyl, —O—C$_{1-4}$alkyl, cyano and nitro.

In another embodiment of the present invention, R$^3$ is selected from the group consisting of halogen, —C$_{1-4}$alkyl, halogen substituted C$_{1-4}$alkyl, —O—C$_{1-4}$alkyl, cyano and nitro.

In another embodiment of the present invention, R$^3$ is selected from the group consisting of halogen and cyano.

In another embodiment of the present invention, R$^3$ is halogen.

In another embodiment of the present invention, R$^3$ is selected from the group consisting of chloro, fluoro, methyl, methoxy, cyano and nitro.

In another embodiment of the present invention, R$^3$ is selected from the group consisting of chloro and cyano.

In another embodiment of the present invention, R$^3$ is chloro.

In an embodiment of the present invention R$^2$ is halogen and R$^3$ is halogen. In another embodiment of the present invention R$^2$ is chloro and R$^3$ is chloro.

In an embodiment of the present invention, R$^4$ is selected from the group consisting of hydrogen, C$_{1-4}$alkyl and

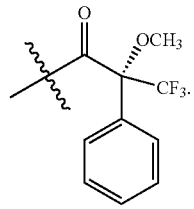

In another embodiment of the present invention, R$^4$ is selected from the group consisting of hydrogen, C$_{1-4}$alkyl and halogen substituted C$_{1-4}$alkyl.

In another embodiment of the present invention, R$^4$ is selected from the group consisting of hydrogen and C$_{1-4}$alkyl.

In another embodiment of the present invention, R$^4$ is selected from the group consisting of hydrogen, methyl, ethyl and

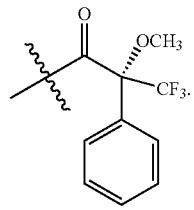

In an embodiment of the present invention, R$^5$ is selected from the group consisting of hydrogen, halogen and C$_{1-4}$alkyl.

In another embodiment of the present invention, R$^5$ is selected from the group consisting of hydrogen, C$_{1-4}$alkyl and halogen substituted C$_{1-4}$alkyl.

In another embodiment of the present invention, R$^5$ is selected from the group consisting of hydrogen and C$_{1-4}$alkyl.

In another embodiment of the present invention, R$^5$ is selected from the group consisting of hydrogen and methyl.

In an embodiment of the present invention, R$^6$ is selected from the group consisting of C$_{1-4}$alkyl, halogen substituted C$_{1-4}$alkyl, —C$_{1-4}$alkyl-CN, —C$_{1-4}$alkyl-OH, —C$_{1-4}$alkyl-Y—R$^9$ and —CH$_2$-phenyl; wherein the phenyl is optionally substituted with one to two substituent independently selected from halogen, C$_{1-4}$alkyl, halogen substituted C$_{1-4}$alkyl, —O—C$_{1-4}$alkyl, —O-(halogen substituted C$_{1-4}$alkyl), nitro or cyano.

In another embodiment of the present invention, R$^6$ is selected from the group consisting of C$_{1-4}$alkyl, halogen substituted C$_{1-4}$alkyl, —C$_{1-4}$alkyl-CN, —C$_{1-4}$alkyl-OH, —C$_{1-4}$alkyl-Y—R$^9$ and —CH$_2$-phenyl; wherein the phenyl is optionally substituted with a halogen.

In another embodiment of the present invention, R$^6$ is selected from the group consisting of C$_{1-4}$alkyl, halogen substituted C$_{1-4}$alkyl, —C$_{1-4}$alkyl-CN, —C$_{1-4}$alkyl-OH and —C$_{1-4}$alkyl-Y—R$^9$.

In another embodiment of the present invention, R$^6$ is selected from the group consisting of C$_{1-4}$alkyl, halogen substituted C$_{1-4}$alkyl and —C$_{1-4}$alkyl-CN.

In another embodiment of the present invention, $R^6$ is selected from the group consisting of methyl, chloro-methyl-, trifluoromethyl, cyano-methyl-, hydroxy-methyl, 3-fluoro-benzyl-, methoxy-methyl-, ethoxy-methyl-, methyl-thio-methyl-, ethyl-thio-methyl-, n-propyl-thio-methyl-, isopropyl-thio-methyl-, trifluoroethyl-thio-methyl-, benzyl-thio-methyl-, 4-fluorophenyl-thio-methyl-, 4-methoxybenzyl-thio-methyl-, 4-chlorobenzyl-thio-methyl-, 4-fluorobenzyl-thio-methyl-, methyl-sulfonyl-methyl-, ethyl-sulfonyl-methyl-, n-propyl-sulfonyl-methyl-, isopropyl-sulfonyl-methyl-, trifluoroethyl-sulfonyl-methyl-, 4-fluorophenyl-sulfonyl-methyl-, 4-methylphenyl-sulfonyl-methyl-, 4-methylphenyl-sulfonyloxy-methyl-, benzyl-sulfonyl-methyl-, 4-fluorobenzyl-sulfonyl-methyl-, 4-methoxybenzyl-sulfonyl-methyl- and 4-methylcarbonylaminophenyl-sulfonyl-methyl-.

In an embodiment of the present invention, Y is selected from —O—, —S—, —SO—, —SO$_2$— and —O—SO$_2$—.

In another embodiment of the present invention, Y is selected from —O—, —S— and —SO$_2$—.

In another embodiment of the present invention, $R^9$ is selected from $C_{1-4}$alkyl, halogen substituted $C_{1-4}$alkyl, phenyl and —CH$_2$-phenyl; wherein the phenyl, whether alone or as part of a substituent group, is optionally substituted with one or more substituents independently selected from halogen, $C_{1-4}$alkyl, —O—$C_{1-4}$alkyl or —NR$^M$—C(O)—$C_{1-4}$alkyl; wherein R$^M$ is selected from hydrogen or $C_{1-2}$alkyl.

In another embodiment of the present invention, $R^9$ is selected from $C_{1-4}$alkyl, halogen substituted $C_{1-4}$alkyl and —CH$_2$-phenyl; wherein the phenyl is optionally substituted with one or more substituents independently selected from halogen, $C_{1-4}$alkyl or —O—$C_{1-4}$alkyl.

In an embodiment of the present invention, $R^{10}$ is selected from the group consisting of hydrogen, halogen, $C_{1-4}$alkyl and

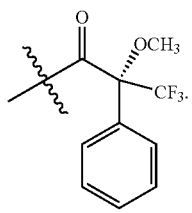

In another embodiment of the present invention, $R^{10}$ is selected from the group consisting of hydrogen, $C_{1-4}$alkyl and halogen substituted $C_{1-4}$alkyl.

In another embodiment of the present invention, $R^{10}$ is selected from the group consisting of hydrogen, fluoro, methyl and

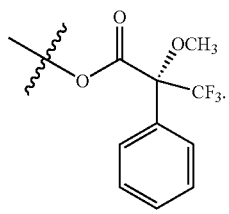

In another embodiment of the present invention, $R^{10}$ is hydrogen.

In an embodiment of the present invention, $R^{11}$ is selected from the group consisting of hydrogen, halogen and $C_{1-4}$alkyl.

In another embodiment of the present invention, $R^{11}$ is selected from the group consisting of hydrogen and halogen.

In another embodiment of the present invention, $R^{11}$ is selected from the group consisting of hydrogen and fluoro.

In another embodiment of the present invention, $R^{11}$ is hydrogen.

In an embodiment of the present invention, $R^{10}$ and $R^{11}$ are taken together with the carbon atom to which they are bound to form —C(O)— or —C(=N(OH))—.

In another embodiment of the present invention, $R^{10}$ and $R^{11}$ are taken together with the carbon atom to which they are bound to form —C(O)—.

In an embodiment of the present invention, $R^{12}$ is selected from the group consisting of $C_{1-4}$alkyl, halogen substituted $C_{1-4}$alkyl, —$C_{1-4}$alkyl-CN, —$C_{1-4}$alkyl-OH, —$C_{1-4}$alkyl-Y—$R^9$ and —CH$_2$-phenyl; wherein the phenyl is optionally substituted with one to two substituent independently selected from halogen, $C_{1-4}$alkyl, halogen substituted $C_{1-4}$alkyl, —O—$C_{1-4}$alkyl, —O-(halogen substituted $C_{1-4}$alkyl), nitro or cyano.

In another embodiment of the present invention, $R^{12}$ is selected from the group consisting of $C_{1-4}$alkyl, halogen substituted $C_{1-4}$alkyl and —$C_{1-4}$alkyl-CN.

In another embodiment of the present invention, $R^{12}$ is selected from the group consisting of $C_{1-4}$alkyl and halogen substituted $C_{1-4}$alkyl.

In another embodiment of the present invention, $R^{12}$ is selected from the group consisting of methyl, n-propyl, trifluoromethyl and 2,2,2-trifluoroethyl.

In another embodiment of the present invention, $R^{12}$ is trifluoromethyl.

In an embodiment of the present invention $R^2$ and $R^3$ are each other than hydrogen.

In an embodiment of the present invention $R^1$ is other than —CH$_2$-phenyl.

In an embodiment of the present invention, when $R^4$ is hydrogen and $R^5$ is hydrogen or $C_{1-4}$alkyl; then $R^6$ is other than $C_{1-4}$alkyl. In another embodiment of the present invention, $R^5$ and $R^6$ are not each $C_{1-4}$alkyl. In another embodiment of the present invention, $R^{10}$ and $R^{11}$ are not each $C_{1-4}$alkyl.

In an embodiment of the present invention, $R^6$ is other than —CH$_2$-phenyl. In another embodiment of the present invention, $R^6$ is other than —CH$_2$-benzimidazolyl.

In an embodiment of the present invention, $R^{12}$ is other than —CH$_2$-phenyl. In another embodiment of the present invention, $R^{12}$ is other than —CH$_2$-benzimidazolyl. In yet another embodiment of the present invention, $R^{12}$ is other than $C_{1-4}$alkyl.

In an embodiment of the present invention, wherein $R^{10}$ and $R^{11}$ are taken together with the carbon atom to which they are bound to form —C(O)—, then $R^{12}$ is other than $C_{1-4}$alkyl.

In an embodiment of the present invention are compounds of formula (I) selected from the group consisting of the compounds listed in Tables 1-3 below. In another embodiment of the present invention are compounds of formula (II) selected from the group consisting of the compounds listed in Tables 4-6 below.

Additional embodiments of the present invention, include those wherein the substituents selected for one or more of the variables defined herein (i.e. $R^1$, $R^2$, $R^3$, a, $R^4$, $R^5$, $R^6$, X, Y, $R^7$, $R^8$, $R^9$, $R^{10}$, $R^{11}$, $R^{12}$, etc.) are independently selected to be any individual substituent or any subset of substituents selected from the complete list as defined herein.

Representative compounds of the present invention are as listed in Tables 1-6, below. Tables 1-3 list representative compounds of formula (I). Tables 4-6 list representative compounds of formula (II). Unless otherwise noted, wherein a stereogenic center is present in the compound (as indicated by the "*" symbol), the compound was prepared as a mixture of stereo-configurations.

TABLE 1

Representative Compounds of Formula (I)

| ID No. | $R^1$ | $R^2$ | $R^3$ | $R^5$ | $R^6$ |
|---|---|---|---|---|---|
| 1 | H | chloro | chloro | methyl | 4-fluoro-phenyl-sulfonyl-methyl |
| 2 | H | chloro | chloro | methyl | 4-methyl-phenyl-sulfonyl-methyl |
| 3 | H | chloro | chloro | methyl | 3-fluoro-benzyl |
| 4 | H | chloro | chloro | methyl | hydroxy-methyl |
| 5 | H | chloro | chloro | methyl | methyl-sulfoflyl-methyl |
| 6 | H | chloro | chloro | methyl | 4-methyl-phenyl-sulfonyloxy-methyl |
| 7 | H | chloro | chloro | methyl | cyano-methyl |
| 8 | methyl | chloro | chloro | methyl | cyano-methyl |
| 9 | methyl | chloro | chloro | methyl | trifluoro-methyl |
| 10 | methyl | chloro | chloro | methyl | ethoxy-methyl |
| 11 | ethyl | chloro | chloro | methyl | chloro-methyl |
| 12 | methyl | chloro | chloro | methyl | methyl-thio-methyl |
| 13 | ethyl | chloro | chloro | methyl | trifluoro-methyl |
| 14 | n-propyl | chloro | chloro | methyl | trifluoro-methyl |
| 15 | n-butyl | chloro | chloro | methyl | trifluoro-methyl |
| 16 | ethyl | chloro | chloro | methyl | cyano-methyl |
| 17 | ethyl | chloro | chloro | methyl | methoxy-methyl |
| 18 | methyl | chloro | chloro | methyl | chloro-methyl |
| 20 | H | chloro | chloro | methyl | trifluoro-methyl |
| 21 | methyl | chloro | chloro | methyl | n-propyl-thio-methyl |
| 22 | methyl | chloro | chloro | methyl | 4-fluoro-phenyl-thio-methyl |
| 23 | methyl | chloro | chloro | methyl | benzyl-thio-methyl |
| 24 | methyl | chloro | chloro | methyl | isopropyl-thio-methyl |
| 25 | methyl | chloro | chloro | methyl | ethyl-thio-methyl |
| 29 | methoxy-methyl | chloro | chloro | methyl | trifluoro-methyl |
| 30 | methoxy-methyl | chloro | chloro | methyl | cyano-methyl |
| 31 | ethyl | chloro | chloro | methyl | ethyl-thio-methyl |
| 36 | ethyl | chloro | chloro | methyl | 4-methoxy-benzyl-thio-methyl |
| 38 | ethyl | chloro | chloro | methyl | 4-chloro-benzyl-thio-methyl |
| 39 | ethyl | chloro | chloro | methyl | 4-fluoro-benzyl-thio-methyl |
| 40 | methoxy-methyl | chloro | chloro | methyl | methyl |
| 42 | methyl | chloro | chloro | methyl | n-propyl-sulfonyl-methyl |
| 44 | ethyl | chloro | chloro | methyl | trifluoro-ethyl-thio-methyl |
| 45 | methyl | chloro | chloro | methyl | benzyl-sulfonyl-methyl |
| 46 | ethyl | chloro | chloro | methyl | 4-fluoro-benzyl-sulfonyl-methyl |
| 47 | ethyl | chloro | chloro | methyl | 4-methoxy-benzyl-sulfonyl-methyl |
| 48 | ethyl | chloro | chloro | methyl | ethyl-sulfonyl-methyl |
| 49 | ethyl | chloro | chloro | methyl | trifluoro-ethyl-sulfonyl-methyl |
| 51 | methyl-thio-methyl | chloro | chloro | methyl | methyl |
| 53 | cyano-methyl | chloro | chloro | methyl | methyl |
| 54 | methyl | chloro | chloro | methyl | isopropyl-sulfonyl-methyl |
| 55 | methyl | chloro | chloro | methyl | ethyl-sulfonyl-methyl |
| 56 | methyl | chloro | chloro | methyl | 4-(methyl-carbonyl-amino)-phenyl-thio-methyl |
| 64 | methoxy-ethyl | chloro | chloro | methyl | methyl |
| 66 | cyano-methyl | chloro | chloro | methyl | trifluoro-methyl |
| 59 | H | chloro | chloro | H | trifluoro-methyl |
| 82[a] | H | chloro | chloro | H | trifluoro-methyl |
| 83[a] | H | chloro | chloro | H | trifluoro-methyl |
| 111 | H | methyl | methyl | H | trifluoro-methyl |
| 112 | H | chloro | fluoro | H | trifluoro-methyl |
| 113 | H | fluoro | fluoro | H | trifluoro-methyl |
| 128 | H | methyl | chloro | H | trifluoro-methyl |
| 135 | H | trifluoro-methyl | cyano | H | trifluoro-methyl |
| 155 | H | nitro | nitro | H | trifluoro-methyl |
| 156 | H | H | chloro | H | trifluoro-methyl |
| 157 | H | methoxy | methoxy | H | trifluoro-methyl |

[a] Racemic compound #59 was reacted to yield a mixture of diastereomers - the compounds #78 and #107, which were then separated. The isolated compounds #78 and #102 were then reacted to yield compounds #82 and #83, which were determined to have (−) and (+) optical rotation as noted.

TABLE 2

Representative Compounds of Formula (I)

| ID No. | $R^1$ | $R^4$ | $R^5$ | $R^6$ |
|---|---|---|---|---|
| 28 | methyl | methyl | methyl | cyano-methyl |
| 34 | methyl | methyl | methyl | trifluoro-methyl |
| 35 | H | methyl | methyl | trifluoro-methyl |
| 61 | methyl | methyl | H | trifluoro-methyl |
| 62 | ethyl | ethyl | H | trifluoro-methyl |

TABLE 2-continued

Representative Compounds of Formula (I)

| ID No. | R¹ | R⁴ | R⁵ | R⁶ |
|---|---|---|---|---|
| 67 | H | t-butyl-dimethyl-silyl- | H | trifluoro-methyl |
| 78[b] | H | (structure: C(=O)-C(OCH₃)(CF₃)(phenyl)) | H | trifluoro-methyl |
| 107[b] | H | (structure: C(=O)-C(OCH₃)(CF₃)(phenyl)) | H | trifluoro-methyl |

[b]Racemic compound #59 was reacted to yield a mixture of diastereomers - the compounds #78 and #107, which were then separated.

TABLE 3

Representative Compounds of Formula (I)

| ID No. | R¹ | R² | R³ | R⁵ | R⁶ |
|---|---|---|---|---|---|
| 27 | H | chloro | chloro | methyl | trifluoromethyl |
| 33 | methyl | chloro | chloro | methyl | trifluoromethyl |
| 37 | ethyl | chloro | chloro | methyl | trifluoromethyl |

TABLE 4

Representative Compounds of Formula (II)

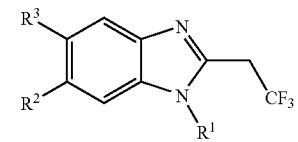

| ID No. | R¹ | R² | R³ | W | R⁶ |
|---|---|---|---|---|---|
| 26 | methoxy-methyl | chloro | chloro | O | methyl |
| 114 | H | chloro | chloro | O | trifluoromethyl |
| 141 | H | chloro | chloro | N(OH) | trifluoromethyl |

TABLE 4-continued

Representative Compounds of Formula (II)

| ID No. | R¹ | R² | R³ | W | R⁶ |
|---|---|---|---|---|---|
| 159 | H | fluoro | chloro | O | trifluoromethyl |
| 160 | H | methyl | chloro | O | trifluoromethyl |

TABLE 5

Representative Compounds of Formula (II)

| ID No. | R¹ | R² | R³ |
|---|---|---|---|
| 57 | methoxy-methyl | chloro | chloro |
| 58 | methylthio-methyl | chloro | chloro |
| 41 | H | chloro | chloro |
| 68 | H | trifluoro-methyl | chloro |
| 69 | H | trifluoro-methyl | cyano |
| 71 | methyl | chloro | chloro |
| 72 | 4-chloro-phenoxy-methyl | chloro | chloro |
| 73 | methyl-sulfonyl-methyl | chloro | chloro |
| 74 | phenyl-carbonyl-methyl | chloro | chloro |
| 75 | 4-fluoro-phenyl-carbonyl-methyl | chloro | chloro |
| 76 | 4-nitro-phenyl-carbonyl-methyl | chloro | chloro |
| 77 | 2,4-dimethoxy-phenyl-carbonyl-methyl | chloro | chloro |
| 79 | 4-bromo-phenyl-carbonyl-methyl | chloro | chloro |
| 80 | ethyl-carbonyl-methyl | chloro | chloro |
| 81 | ethoxy-carbofiyl-methyl | chloro | chloro |
| 84 | 2-benzofuryl-carbonyl-methyl | chloro | chloro |
| 85 | 4-chloro-phenyl-carbonyl-methyl | chloro | chloro |
| 86 | 3-methoxy-phenyl-carbonyl-methyl | chloro | chloro |
| 87 | 3-pyridyl-carbonyl-methyl | chloro | chloro |
| 88 | 2-(5-(2-pyridyl)-thienyl)-carbonyl-methyl | chloro | chloro |
| 89 | 4-fluoro-benzyl | chloro | chloro |
| 90 | 2-methoxy-phenyl-carbonyl-methyl | chloro | chloro |
| 91 | 2-thienyl-carbonyl-methyl | chloro | chloro |
| 92 | 2-pyridyl-carbonyl-methyl | chloro | chloro |
| 93 | 3-trifluoro-methyl-benzyl | chloro | chloro |
| 94 | 2,3,4,5,6-pentafluoro-benzyl | chloro | chloro |
| 95 | 3-methyl-benzyl | chloro | chloro |
| 96 | 3-nitro-phenyl-carbonyl-methyl | chloro | chloro |
| 97 | benzyl | chloro | chloro |
| 98 | 2-hydroxy-ethyl | chloro | chloro |
| 99 | 3-pyridyl-methyl | chloro | chloro |
| 100 | 4-trifluoro-methyl-benzyl | chloro | chloro |
| 101 | 4-trifluoro-methoxy-benzyl | chloro | chloro |
| 102 | 2-pyridyl-methyl | chloro | chloro |
| 104 | 5-(2,3-dihydro-benzo[1,4]dioxinyl)-carbonyl-methyl- | chloro | chloro |

TABLE 5-continued

Representative Compounds of Formula (II)

| ID No. | R¹ | R² | R³ |
|---|---|---|---|
| 105 | 4-nitro-benzyl | chloro | chloro |
| 108 | 4-pyridyl-methyl | chloro | chloro |
| 109 | 3-cyano-methyl-benzyl | chloro | chloro |
| 110 | 2-cyano-methyl-benzyl | chloro | chloro |
| 115 | 4-fluoro-phenoxy-ethyl | chloro | chloro |
| 116 | 4-cyano-benzyl | chloro | chloro |
| 117 | 2-fluoro-benzyl | chloro | chloro |
| 119 | 3-fluoro-benzyl | chloro | chloro |
| 120 | 3-chloro-benzyl | chloro | chloro |
| 121 | 4-chloro-benzyl | chloro | chloro |
| 123 | 3-fluoro-phenoxy-ethyl | chloro | chloro |
| 124 | 4-chloro-phenoxy-ethyl | chloro | chloro |
| 125 | 2-chloro-benzyl | chloro | chloro |
| 126 | 3-phenyl-5-methyl-isoxazol-4-yl-carbonyl-methyl- | chloro | chloro |
| 129 | 3-methoxy-beflzyl | chloro | chloro |
| 130 | 2-methoxy-5-nitro-benzyl | chloro | chloro |
| 131 | 4-pyrazolyl-benzyl | chloro | chloro |
| 132 | 4-[1,2,3]-thiodiazol-4-yl-benzyl- | chloro | chloro |
| 133 | 3-(5-methyl)-isoxazolyl-methyl | chloro | chloro |
| 134 | 3-trifluoro-methoxy-benzyl | chloro | chloro |
| 136 | 4-cyano-phenoxy-ethyl | chloro | chloro |
| 137 | 2-nitro-benzyl | chloro | chloro |
| 138 | 4-pyrrolyl-benzyl | chloro | chloro |
| 139 | 3-nitro-benzyl | chloro | chloro |
| 140 | 4-trifluoromethyl-thio-benzyl | chloro | chloro |
| 142 | 4-methyl-sulfonyl-benzyl | chloro | chloro |
| 144 | trans-butan-2-one oxime | chloro | chloro |
| 145 | trans-butan-2-one oxime | chloro | chloro |
| 146 | 4-benzyloxy-benzyl | chloro | chloro |
| 147 | 4-methoxy-benzyl | chloro | chloro |
| 148 | 2-hydroxy-n-butyl | chloro | chloro |
| 149 | 4-bromo-benzyl | chloro | chloro |
| 150 | 4-ethoxy-carbonyl-benzyl | chloro | chloro |
| 151 | 2-bromo-benzyl | chloro | chloro |
| 153 | 4-benzaldehyde | chloro | chloro |

TABLE 6

Representative Compounds of Formula (II)

| ID No. | R¹ | R² | R³ | R¹⁰ | R¹¹ | R¹² |
|---|---|---|---|---|---|---|
| 50 | cyano-methyl | chloro | chloro | methyl | H | methyl |
| 60 | methoxy-ethyl | chloro | chloro | methyl | H | methyl |
| 63 | methoxy-methyl | chloro | chloro | methyl | H | methyl |
| 65 | methoxy-methyl | chloro | chloro | methyl | H | n-propyl |
| 70 | H | chloro | chloro | H | H | 2,2,2-trifluoro-ethyl |
| 106 | H | chloro | chloro | (–O–C(=O)–C(OCH₃)(CF₃)(phenyl)) | H | trifluoro-methyl |
| 152 | H | chloro | chloro | fluoro | H | trifluoro-methyl |
| 154 | H | chloro | chloro | fluoro | fluoro | trifluoro-methyl |

As used herein, unless otherwise noted, "halogen" shall mean chlorine, bromine, fluorine and iodine.

As used herein, the term "alkyl" whether used alone or as part of a substituent group, shall include straight and branched chains. For example, alkyl radicals include methyl, ethyl, propyl, isopropyl, butyl, isobutyl, sec-butyl, t-butyl, pentyl and the like. Similarly, "$C_{1-4}$alkyl" shall denote an alkyl chain as defined above comprising one to four carbon atoms.

As used herein, unless otherwise noted, the term "halogen substituted $C_{1-4}$alkyl" shall mean any of the above defined alkyl chains substituted with one or more, preferably one to three halogens. Preferably the halogen(s) are selected from chloro or fluoro. Suitable examples include, but are not limited to chloromethyl, dichloromethyl, fluoromethyl, trifluoromethyl, 2,2,2-trifluoroethyl, and the like.

As used herein, unless otherwise noted, the terms "alkoxy" and "—O-alkyl" shall denote an oxygen ether radical of the above described straight or branched chain alkyl groups. For example, methoxy, ethoxy, n-propoxy, sec-butoxy, t-butoxy, n-hexyloxy and the like. Similarly, "$C_{1-4}$alkoxy" or "—O—$C_{1-4}$alkyl" shall denote an oxygen ether radical as defined above comprising one to four carbon atoms.

As used herein, unless otherwise noted, "aryl" shall refer to unsubstituted carbocylic aromatic groups such as phenyl, naphthyl, and the like.

As used herein, unless otherwise noted, "aralkyl" shall mean any lower alkyl group substituted with an aryl group such as phenyl, naphthyl and the like. For example, benzyl, phenylethyl-, phenyl-n-propyl-, naphthylmethyl-, and the like. One skilled in the art will recognize that the terms "benzyl" and "—CH$_2$-phenyl" are used interchangeably throughout the specification.

As used herein, unless otherwise noted, the term "cycloalkyl" shall mean any stable 3-8 membered monocyclic, saturated ring system, for example, cyclopropyl, cyclobutyl, cyclopentyl, cyclohexyl, cycloheptyl and cyclooctyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, the notation "*" shall denote the presence of a stereogenic center.

When a particular group is "substituted" (e.g., Phe, aryl, heteroalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, CH$_2$=CH—CH$_2$—, and the like; amides—groups of the formula —C(O)—R' wherein R' is for example methyl, phenyl, trifluoromethyl, and the like; N-sulfonyl derivatives—groups of the formula —SO$_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

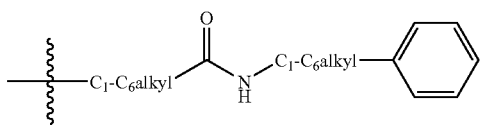

One skilled in the art will further recognize that some substituent groups may begin or terminate with a "-", as in for example, "ethyl-carbonyl-methyl-". The presence of the "-" is intended, for the sake of clarity, to indicate the point of attachment between the substituent group and the rest of the molecule.

Abbreviations used in the specification, particularly the Schemes and Examples, are as follows:
DCM=Dichloromethane
DMAC=N,N-Dimethylacetamide
DME=1,2-Dimethoxyethane
DMF=N,N-Dimethylformamide
DMSO=Dimethylsulfoxide
EtOAc=Ethyl acetate
mCPBA=m-Chloro-peroxybenzoic acid
MeOH=Methanol
NMP=N-methyl-2-pyrrolidinone
Oxone®=Potassium monopersulfate triple salt
TEMPO=2,2,6,6,-Tetramethyl-1-piperidinyloxy, free radical
THF=Tetrahydrofuran The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "*Design of Prodrugs*", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) wherein $R^4$ is hydrogen may be prepared according to the process outlined in Scheme 1.

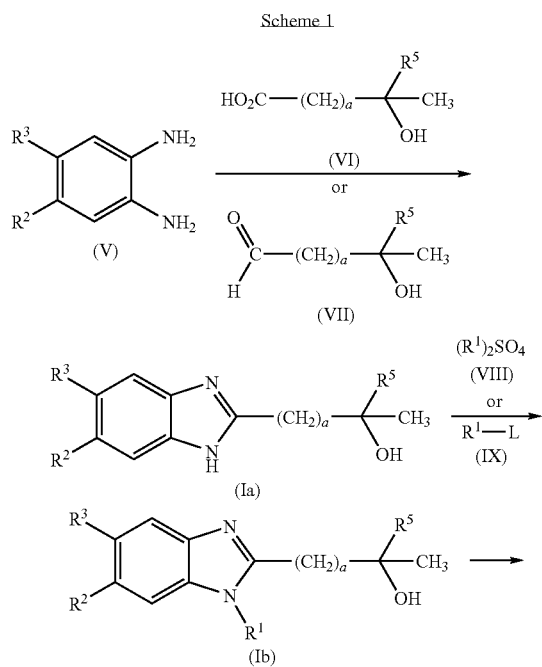

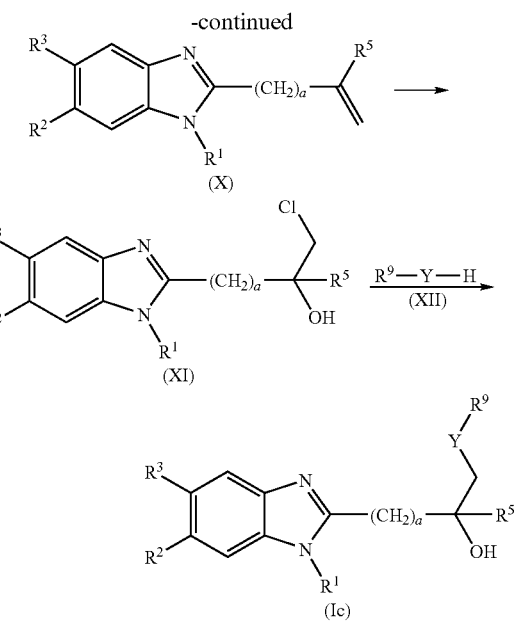

Accordingly, a suitably substituted compound of formula (V), a known compound or compound prepared by known methods, is reacted with a suitably substituted compound of formula (VI), a known compound or compound prepared by known methods, in the presence of an acid such as HCl, $H_2SO_4$, acetic acid, and the like, in water, to yield the corresponding compound of formula (Ia).

Alternatively, a suitably substituted compound of formula (V), a known compound or compound prepared by known methods, is reacted with a suitably substituted compound of formula (VII), a known compound or compound prepared by known methods, in the presence of sodium bisulfite, in water, to yield the corresponding compound of formula (Ia).

Alternatively, the compound of formula (V), a known compound or compound prepared by known methods, is reacted with a suitably substituted compound of formula (VII), a known compound or compound prepared by known methods, in the presence of Oxone® or silica supported thionyl chloride, according to known methods, to yield the corresponding compound of formula (Ia).

Alternatively still, the compound of formula (V) is reacted with a suitably substituted carboxylic acid derivative, such as a suitably substituted acid chloride or anhydride, a known compound or compound prepared by known methods, according to known methods, followed by treatment with an organic acid such as toluenesulfonic acid or with a Lewis acid such as $Al(CH_3)_3$, $(CH_3CH_2)_2AlCl$, and the like, according to known methods, to yield the corresponding compound of formula (Ia).

(See also for example, Mayer, J. P., Lweis, G. S., McGee, C., Bankaitis-Davis, D., *Tetrahedron Letters*, 1998, 39(37) pp 6655-6658; Ben Alloum, A., Bougrin, k., Soufiaoui, M., *Tetrahedron letters*, 2003, 44(31) pp 5935-5937; Beaulieu, P. L., Hache, B., Von Moos, E., *Synthesis*, 2003 (11), pp 1683-1692; and/or Matsushita, H., Lee, S-H., Joung, M., Clapham, B., Janda, K. D., *Tetrahedron Letters*, 2004 45(2), pp 313-316)

The compound of formula (Ia) is optionally reacted with a suitably substituted compound of formula (VIII), a known compound or compound prepared by known methods, or a suitably substituted compound of formula (IX), wherein L is a leaving group, a known compound or compound prepared by known methods, in the presence of a base such as NaOH, KOH, NaH, K$_2$CO$_3$, and the like, in a polar, aprotic organic solvent such as acetonitrile, THF, DMF, and the like, to yield the corresponding compound of formula (Ib).

The compound of formula (Ib) is optionally reacted with a dehydrating reagent such as Burgess' salt, and the like, in the presence of an organic solvent such as THF, DMF, DCM, acetonitrile, toluene, and the like, to yield the corresponding compound of formula (X).

The compound of formula (X), wherein a is 0, may be further, optionally reacted with 1,3,5-trichloroisocyanoic acid, in a mixture of organic solvent which is miscible with water and water such as acetone:water, THF:water, acetonitrile:water, DMF:water, dioxane:water, and the like, to yield the corresponding compound of formula (XI).

The compound of formula (XI) is reacted with a suitably substituted compound of formula (XII), a known compound or compound prepared by known methods, in the presence of a base such as sodium methoxide, sodium t-butoxide, sodium

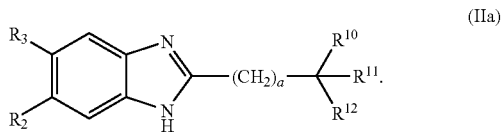

One skilled in the art will further recognize that the compound of formula (IIa) may then be further, optionally substituted with a suitably selected R$^1$ group, as outlined in Scheme 1 above.

One skilled in the art will recognize further that compounds of formula (I) wherein R$^4$ is other than hydrogen may be prepared by reacting the corresponding compound of formula (I) wherein R$^4$ is hydrogen with a suitably substituted alkylating or acylating reagent, according to known methods.

Compounds of formula (I) may alternatively, be prepared according to the process outlined in Scheme 2.

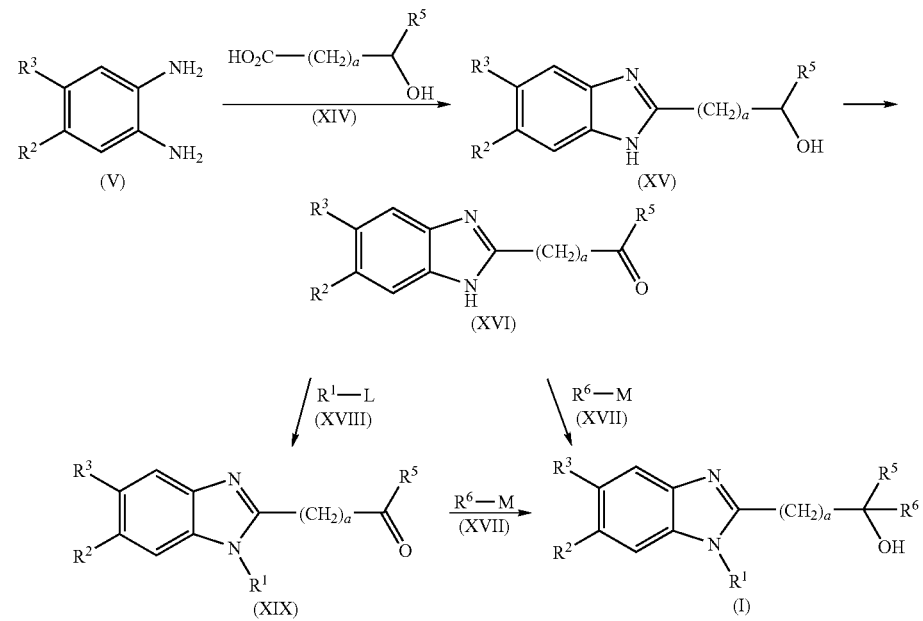

Scheme 2 hydride, and the like, in an organic solvent such as DMF, THF, dioxane, methanol, and the like, to yield the corresponding compound of formula (Ic).

One skilled in the art will recognize that compounds of formula (II) may be similarly prepared according to the process outlined in Scheme 1 above, by selecting and substituting, a suitably substituted compound of formula (XIII)

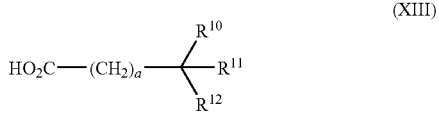

(XIII)

a known compound or compound prepared by known methods, for the compound of formula (VI), to yield the corresponding compound of formula (IIa)

Accordingly, a suitably substituted compound of formula (V), a known compound or compound prepared by known methods, is reacted with a suitably substituted compound of formula (XIV), a known compound or compound prepared by known methods, in the presence of an acid such as HCl, H$_2$SO$_4$, acetic acid, and the like, in water, to yield the corresponding compound of formula (XV).

The compound of formula (XV) is reacted with a suitably selected oxidizing agent such as Na$_2$Cr$_2$O$_7$, and the like, in the presence of an acid such as sulfuric acid, and the like, in an aqueous solvent, to yield the corresponding compound of formula (XVI).

Alternatively, the compound of formula (XV) wherein R$^5$ is hydrogen is reacted with a suitably selected oxidizing agent such as MnO$_2$ in a solvent such as dichloromethane, dichloroethane, benzene, toluene and the like at a temperature range from room temperature to 110°, preferably at room temperature; Dess-Martin Periodinane in a solvent such as dichloromethane, dichloroethane and the like at a temperature range from 0° C. to room temperature, preferably at room temperature; or a mixture of (a) TEMPO, (b) bleach and (c) KBr or NaBr, in an organic solvent such as THF, DME, dioxane, and the like, at a reduced temperature in the range of about −40° C. to about room temperature, preferably at a reduced temperature in the range of about −10 to about 0° C.; to yield the corresponding compound of formula (XVI).

The compound of formula (XVI) is reacted with a suitably substituted compound of formula (XVII), wherein M is MgBr or Li, a known compound or compound prepared by known methods, according to known methods, to yield the corresponding compound of formula (I) wherein $R^1$ is hydrogen.

Alternatively, the compound of formula (XVI) is reacted with a suitably substitued compound of formula (XVIII), wherein L is a suitable leaving group such as Br, I, and the like, a known compound or compound prepared by known methods, in the presence of an base such as NaH, $K_2CO_3$, $Na_2CO_3$, and the like, in an organic solvent such as DMF, DMAC, DMSO, NMP, and the like, to yield the corresponding compound of formula (XIX).

The compound of formula (XIX) is reacted with a suitably substituted compound of formula (XVII), wherein M is MgBr or Li, a known compound or compound prepared by known methods, according to known methods, to yield the corresponding compound of formula (I) wherein $R^1$ is other than hydrogen.

One skilled in the art will recognize that compound of formula (II) may be similarly prepared according to the process outlined in Scheme 2 above, by selecting and substituting, suitably substituted starting materials and reagents.

One skilled in the art will further recognize that compounds of formula (II) wherein $R^{10}$ and $R^{11}$ are taken together with the carbon atom to which they are bound to form a group selected from —C=N(OH) or —C=N(O—$C_{1-4}$alkyl) may be prepared from the corresponding compound of formula (II) wherein $R^{10}$ and $R^{11}$ are taken together with the carbon atom to which they are bound to form —C(O), according to known methods.

The present invention further comprises pharmaceutical compositions containing one or more compounds of formula (I) and/or (II) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.5-5.0 mg/kg/day, preferably from about 1.0-3.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders or conditions modulated by the androgen receptor described in the present invention may also be carried out using a pharmaceutical composition comprising any of the compounds as defined herein and a pharmaceutically acceptable carrier. The pharmaceutical composition may contain between about 0.01 mg and 500 mg, preferably about 50 to 100 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders or conditions modulated by the androgen receptor is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day. Preferably, the range is from about 0.5 to about 5.0 mg/kg of body weight per day, most preferably, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

Example 1

3-(5,6-dichloro-1H-benzoimidazol-2-yl)-3-hydroxy-butyronitrile

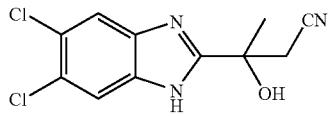

CH$_3$CN was added to a solution of n-butyl lithium in THF (8 ml) at −78° C. and the mixture was stirred at −78° C. for 45 minutes. To this solution was added 1-(5,6-dichloro-1H-benzimidazol-2-yl)-ethanone in THF (6 ml) and the resulting mixture was stirred at −78° C. for an addition ½ hour. After stirring at 0° C. for 6 hrs, water was added, the resulting solution was extracted with EtOAc, the organic layer was washed with brine and then dried over anhydrous Na$_2$SO$_4$. Solvent was distilled off under reduced pressure. Column chromatography (silica gel, EtOAc/hexanes 10% to 50%) yielded the title product as an off-white solid.
MS m/z (M+H) 270

Example 2

2-(5,6-Dichloro-1-ethyl-1H-benzoimidazol-2-yl)-1-(2,2,2-trifluoro-ethylsulfanyl)-propan-2-ol

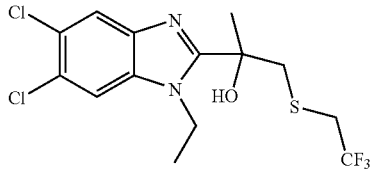

To 1-chloro-2-(5,6-dichloro-1-ethyl-1H-benzoimidazol-2-yl)-propan-2-ol (249 mg) in methanol (5 mL) at room temperature was added a solution of 2,2,2-trifluoroethanethiol (109 mg) and sodium methoxide (0.222 mls of 25 wt % in MeOH). The resulting mixture was then stirred at room temperature overnight. The reaction mixture was concentrated. The crude product was purified by flash chromatography (10%-40% EtOAc/hexanes) to yield the title compound as a brown solid.
$^1$H NMR (400 MHz, d$_6$-DMSO): δ 7.96 (s, 1H), 7.88 (s, 1H), 6.12 (s, 1H), 4.53-4.61 (m, 2H), 3.48-3.54 (m, 2H), 3.31 (ABq, 2H, J$_{AB}$=13.3 Hz, Δv$_B$=71 Hz), 1.69 (s, 3H), 1.35 (t, 3H, J=7.0 Hz).

Example 3

2-(5,6-Dichloro-1-methyl-1H-benzoimidazol-2-yl)-1-phenylmethanesulfonyl-propan-2-ol

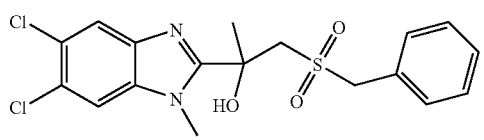

To a solution of 2-(5,6-dichloro-1-methyl-1H-benzoimidazol-2-yl)-1-phenylmethanesulfanyl-propan-2-ol (76.5 mg) in CH$_2$Cl$_2$ (2 mL) at room temperature was added mCPBA (69 mg). The resulting mixture was stirred at room temperature overnight. The reaction was then quenched with saturated NaHCO$_3$ (aq) and extracted with EtOAC. The crude product was purified by flash chromatography (10%-70% EtOAc/hexanes) to yield the title compound as a white foam.
$^1$H NMR (300 MHz, CDCl$_3$): δ 7.82 (s, 1H), 7.59-7.62 (m, 2H), 7.50 (s, 1H), 7.42-7.44 (m, 3H), 5.09 (s, 1H), 4.56 (ABq, 2H, J$_{AB}$=13.7 Hz, Δv$_{AB}$=137 Hz), 4.02 (s, 3H), 3.86 (ABq, 2H, J$_{AB}$=15.1 Hz, Δv$_{AB}$=354 Hz), 1.68 (s, 3H).

Example 4

2-(5,6-Dichloro-1-ethyl-1H-benzoimidazol-2-yl)-1-(4-methoxy-phenylmethanesulfonyl)-propan-2-ol

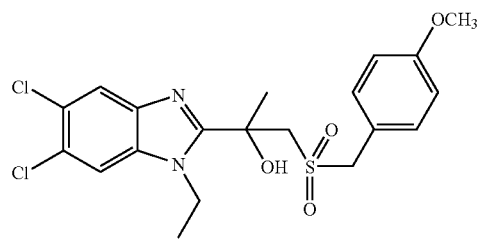

To a solution of 2-(5,6,-dichloro-1-ethyl-1H-benzoimidazol-2-yl)-1-(4-methoxy-phenylmethanesulfanyl)-propan-2-ol (97.6 mg) in CH$_2$Cl$_2$ (2 mL) at room temperature was added mCPBA (93 mg). The resulting mixture was stirred at room temperature overnight. The reaction was quenched with saturated NaHCO$_3$ (aq) and extracted with EtOAc. The crude product was purified by flash chromatography (20%-60% EtOAc/hexanes) to yield the title compound as an off-white solid.
$^1$H NMR (300 MHz, CDCl$_3$): δ 7.81 (s, 1H), 7.51 (s, 1H), 7.24 (ABq, 2H, J$_{AB}$=8.6 Hz, Δv$_{AB}$=173 Hz), 5.19 (s, 1H), 4.44 (ABq, 2H, J$_{AB}$=13.9 Hz, Δv$_{AB}$=149 Hz), 4.41-4.69 (m, 2H), 3.85 (ABq, 2H, J$_{AB}$=15 Hz, Δv$_{AB}$=367 Hz), 3.83 (s, 3H), 1.68 (s, 3H), 1.48 (t, 3H, J=7.1 Hz).

Example 5

2-(5,6-Dichloro-1-ethyl-1H-benzoimidazol-2-yl)-1-ethylsulfanyl-propan-2-ol

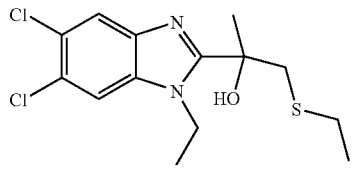

To 1-chloro-2-(5,6-dichloro-1-ethyl-1H-benzoimidazol-2-yl)-propan-2-ol (161 mg) in methanol (5 mL) at room temperature was added a solution of ethanethiol (37 mg) and sodium methoxide (0.144 mls of 25 wt % in MeOH). The resulting mixture was stirred at room temperature overnight. The reaction mixture was quenched with NH$_4$Cl (aq), extracted with EtOAc, and dried over Na$_2$SO$_4$. The crude product was purified by flash chromatography (10%-40% EtOAc/hexanes) to yield the title compound as an off-white solid.

$^1$H NMR (300 MHz, CDCl$_3$): δ 7.80 (s, 1H), 7.45 (s, 1H), 4.43-4.64 (m, 2H), 3.77 (s, 1H), 3.35 (ABq, 2H, J$_{AB}$=13.6 Hz, Δv$_{AB}$=246 Hz, 2.48-2.60 (m, 2H), 1.71 (s, 3H), 1.47 (t, 3H, J=7.2 Hz), 1.24 (t, 3H, J=7.4 Hz).

Example 6

2-(5,6-Dichloro-1-ethyl-1H-benzoimidazol-2-yl)-1-(2,2,2-trifluoro-ethanesulfonyl)-propan-2-ol

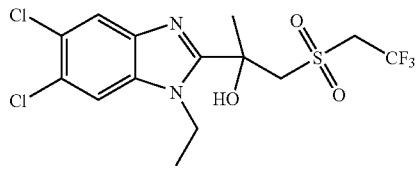

To 2-(5,6-dichloro-1-ethyl-1H-benzoimidazol-2-yl)-1-(2,2,2-trifluoro-ethylsulfanyl)-propan-2-ol (101 mg) in CH$_2$Cl$_2$ (2 mL) at room temperature was added mCPBA (106 mg). The resulting mixture was stirred at room temperature for 16 h. The reaction was quenched with sat. NaHCO$_3$ (aq), extracted with EtOAc, dried over Na$_2$SO$_4$, filtered off dessicant, and concentrated. The residue was chromatographed with 10%-60% EtOAc/hexanes as the eluant to yield the title compound as a white solid.

$^1$H NMR (300 MHz, CDCl$_3$): δ 7.74 (s, 1H), 7.50 (s, 1H), 4.87-5.01 (m, 1H), 4.83 (s, 1H), 4.41-4.66 (m, 2H), 4.16 (ABq, 2H, J$_{AB}$=15.4 Hz, Δv$_{AB}$=334 Hz), 3.78-3.93 (m, 1H), 1.71 (s, 3H), 1.48 (t, 3H, J=7.2 Hz).

Example 7

2-(5,6-Dichloro-1-ethyl-1H-benzoimidazol-2-yl)-1-ethanesulfonyl-propan-2-ol

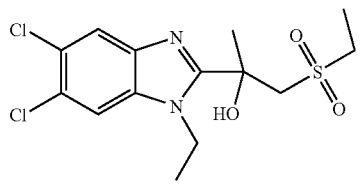

To 2-(5,6-dichloro-1-ethyl-1H-benzoimidazol-2-yl)-1-ethanesulfanyl-propan-2-ol (134.8 mg) in CH$_2$Cl$_2$ (2 mL) at room temperature was added mCPBA (164 mg). The resulting mixture was stirred at room temperature for 16 h. The reaction was quenched with saturated NaHCO$_3$ (aq), extracted with EtOAc, dried over Na$_2$SO$_4$, filtered off dessicant, and concentrated. The residue was chromatographed with 10%-60% EtOAc/hexanes as the eluant to yield the title compound as a white solid.

$^1$H NMR (300 MHz, CDCl$_3$): δ 7.74 (s, 1H), 7.49 (s, 1H), 5.25 (s, 1H), 4.40-4.72 (m, 2H), 3.96 (ABq, 2H, J$_{AB}$=14.8 Hz, Δv$_{AB}$=289 Hz), 3.00-3.26 (m, 2H), 1.74 (s, 3H), 1.47 (t, 3H, J=7.2 Hz), 1.41 (t, 3H, J=7.8 Hz).

Example 8

1-Chloro-2-(5,6-dichloro-1-methyl-1H-benzoimidazol-2-yl)-propan-2-ol

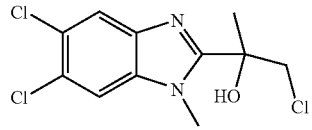

To 5,6-dichloro-1-methyl-2-isopropenyl-1H-benzimidazole (2.5 g) in acetone (30 mL) and water (6 mL) at room temperature was added trichloroisocyanuric acid (845 mg). The resulting mixture was stirred at room temperature for 18 h. The reaction mixture was quenched with water, extracted with EtOAc, and dried over Na$_2$SO$_4$. After removal of the dessicant by filtration, concentration yielded an orange crude oil. The crude product was purified by flash chromatography (10%-40% EtOAc/hexanes) to yield the title compound as a yellow solid.

$^1$H NMR (400 MHz, d$_6$-DMSO): δ 7.97 (s, 1H), 7.90 (s, 1H), 6.22 (s, 1H), 4.04 (m, 2H), 4.01 (s, 3H), 1.68 (s, 3H).

Example 9

2-(5,6-Dichloro-1-methyl-1H-benzoimidazol-2-yl)-1-isobutylsulfanyl-propan-2-ol

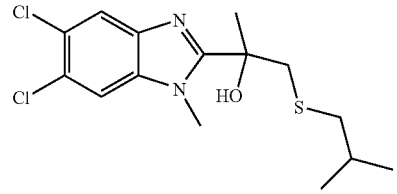

To 1-chloro-2-(5,6-dichloro-1-methyl-1H-benzoimidazol-2-yl)-propan-2-ol (408 mg) in methanol (10 mL) at room temperature was added a solution of 2-methyl-1-propanethiol (150 mg) and sodium methoxide (0.381 mls of 25 wt % in MeOH). The resulting mixture was stirred at room temperature overnight. The reaction mixture was then concentrated. The crude product was purified by flash chromatography (10%-40% EtOAc/hexanes) to yield the title compound as a light orange solid.

$^1$H NMR (300 MHz, CDCl$_3$): δ7.80 (s, 1H), 7.43 (s, 1H), 4.00 (s, 3H), 3.75 (s, 1H), 3.33 (ABq, 2H, J$_{AB}$=13.6 Hz, Δv$_{AB}$=248 Hz), 2.36-2.51 (m, 2H), 1.73-1.83 (m, 1H), 1.70 (s, 3H), 0.95 (d, 6H, J=6.8 Hz)

MS (M+1)=347.1; (M+Na)=369.1.

Example 10

2-(5,6-Dichloro-1-methyl-1H-benzoimidazol-2-yl)-1-(2-methyl-propane-1-sulfonyl)-propan-2-ol

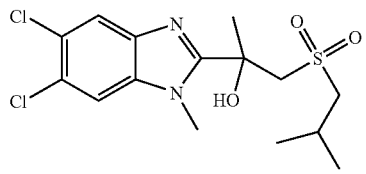

To 2-(5,6-dichloro-1-methyl-1H-benzoimidazol-2-yl)-1-isobutylsulfanyl-propan-2-ol (97 mg) in CH$_2$Cl$_2$ (2 mL) at room temperature was added mCPBA (113 mg) and subsequently stirred overnight. The reaction mixture was quenched with NaHCO$_3$ (aq), extracted with EtOAc, and dried over Na$_2$SO$_4$. The crude product was purified by flash chromatography (10%-70% EtOAc/hexanes) to yield the title compound as an off-white solid.

$^1$H NMR (300 MHz, CDCl$_3$): δ7.73 (s, 1H), 7.48 (s, 1H), 5.17 (s, 1H), 4.02 (s, 3H), 3.96 (ABq, 2H, J$_{AB}$=14.9 Hz, Δv$_{AB}$=260 Hz), 2.37 (nonet, 1H, J=6.7 Hz), 1.73 (s, 3H), 1.12 (d, 3H, J=6.7 Hz), 1.07 (d, 3H, J=6.7 Hz).

Example 11

2-(5,6-Dichloro-1-methyl-1H-benzoimidazol-2-yl)-1-ethylsulfanyl-propan-2-ol

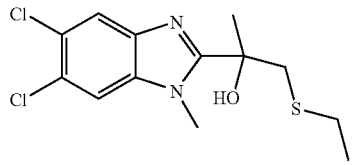

To 1-chloro-2-(5,6-dichloro-1-methyl-1H-benzoimidazol-2-yl)-propan-2-ol (141 mg) in MeOH (4 mL) at room temperature was added a solution of ethanethiol (34 mg) and sodium methoxide (0.132 mls of 25 wt % in MeOH). The resulting mixture was stirred at room temperature overnight. The reaction mixture was then concentrated. The crude product was purified by flash chromatography (10%-40% EtOAc/hexanes) to yield the title compound as a yellow crystalline solid.

$^1$H NMR (300 MHz, CDCl$_3$): δ 7.80 (s, 1H), 7.43 (s, 1H), 4.00 (s, 3H), 3.74 (s, 1H), 3.34 (ABq, 2H, J$_{AB}$=13.7 Hz, Δv$_{AB}$=246 Hz), 2.48-2.62 (m, 2H), 1.71 (3, 3H), 1.25 (t, 3H, J=7.4 Hz)

MS (M+1)=319.0.

Example 12

N-{4-[2-(5,6-Dichloro-1-methyl-1H-benzoimidazol-2-yl)-2-hydroxy-propylsulfanyl]-phenyl}-acetamide

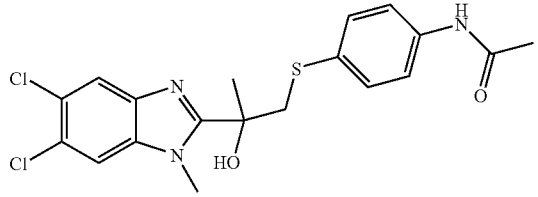

To 1-chloro-2-(5,6-dichloro-1-methyl-1H-benzoimidazol-2-yl)-propan-2-ol (60 mg) in MeOH (2 mL) at room temperature was added a solution of 4-acetamidothiophenol (40 mg) and sodium methoxide (0.047 mls of 25 wt % in MeOH). The resulting mixture was stirred at room temperature overnight. The reaction mixture was concentrated. The crude product was purified by flash chromatography (25%-100% EtOAc/hexanes) to yield the title compound as a white foam solid.

$^1$H NMR (300 MHz, CDCl$_3$): δ 7.72 (s, 1H), 7.29 (s, 1H), 7.27 (s, 1H), 7.20 (s, 4H), 3.85 (s, 3H), 3.83 (s, 1H), 3.62 (ABq, 2H, J$_{AB}$=14 Hz, Δv$_{AB}$=179 Hz), 2.16 (s, 3H), 1.76 (s, 3H)

MS (M+1)=424.0; (M+Na)=446.0

Example 13

5,6-Dichloro-2-(2,2,2-trifluoro-ethyl)-1H-benzoimidazole

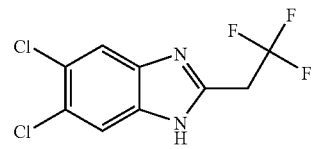

To 4,5-dichloro-1,2-phenylenediamine (25 g) was added 3,3,3-trifluoropropionic acid (25 mls) and 4N HCl (90 mL). The resulting mixture was heated to 100° C. overnight. The reaction mixture was quenched with water, basicified with concentrated NH$_4$OH, extracted with EtOAc, and dried over Na$_2$SO$_4$. The crude product was filtered through a plug of silica gel, eluting with 30% EtOAc/hexanes, and collecting the red band. The fractions were concentrated to yield a mixture of the desired title compound and 4,5-dichloro-1,2-phenylenediamine. The crude material was dissolved in small amount of CH$_2$Cl$_2$ and triturated with hexanes to yield the title compound as a tan solid.

$^1$H NMR (300 MHz, d$_6$-DMSO): δ 12.92 (br s, 1H), 7.88 (s, 2H), 4.06 (ABq, 2H, J$_{AB}$=11 Hz, Δv$_{AB}$=19 Hz).

Example 14

2-[5,6-Dichloro-2-(2,2,2-trifluoro-ethyl)-benzoimidazol-1-yl]-1-phenyl-ethanone

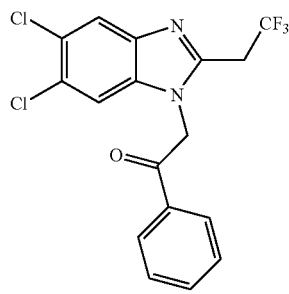

To 5,6-dichloro-2-(2,2,2-trifluoro-ethyl)-1H-benzimidazole (301 mg) in DMF (5 mL) was added sodium hydride (67 mg of 60% in oil dispersion). The resulting mixture was stirred at room temperature for 5 min. To the dark green solution was added 2-bromo-acetophenone (273 mg) and the resulting mixture was stirred at room temperature overnight. The reaction mixture was quenched with water, extracted with EtOAc, and dried over Na$_2$SO$_4$. The crude product was purified by silica gel chromatography (10%-40% EtOAc/hexanes) to yield the title compound as an off-white solid.

$^1$H NMR (300 MHz, CDCl$_3$): δ 8.04-8.07 (m, 2H), 7.92 (s, 1H), 7.73-7.78 (m, 1H), 7.59-7.64 (m, 2H), 7.29 (s, 1H), 5.59 (s, 2H), 3.72 (ABq, 2H, J$_{AB}$=9.9 Hz, Δv$_{AB}$=17.2 Hz).

Example 15

2-[5,6-Dichloro-2-(2,2,2-trifluoro-ethyl)-benzoimidazol-1-yl]-1-(4-fluoro-phenyl)-ethanone

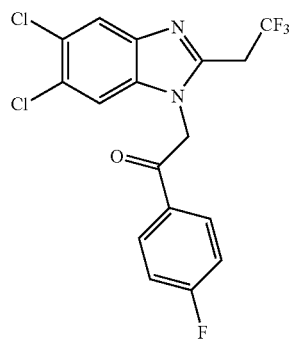

To 5,6-dichloro-2-(2,2,2-trifluoro-ethyl)-1H-benzimidazole (318 mg) in DMF (5 mL) was added sodium hydride (71 mg of 60% in oil dispersion). The resulting mixture was stirred at room temperature for 5 min. To the dark green solution was added 2-bromo-4'fluoroacetophenone (317 mg) and the resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes) to yield the title compound as a peach colored solid.

$^1$H NMR (300 MHz, $CDCl_3$): δ 8.07-8.12 (m, 2H), 7.92 (s, 1H), 7.25-7.32 (m, 3H), 5.56 (s, 2H), 3.72 (ABq, 2H, $J_{AB}$=9.9 Hz, $\Delta v_{AB}$=17.2 Hz).

Example 16

2-[5,6-Dichloro-2-(2,2,2-trifluoro-ethyl)-benzoimidazol-1-yl]-1-(4-nitro-phenyl)-ethanone

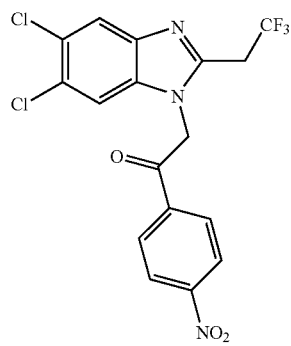

To 5,6-dichloro-2-(2,2,2-trifluoro-ethyl)-1H-benzimidazole (304 mg) in DMF (5 mL) was added sodium hydride (68 mg of 60% in oil dispersion). The resulting mixture was stirred at room temperature for 5 min. To the dark green solution was added 2-bromo-4'nitroacetophenone (348 mg) and the resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes) to yield the title compound as an orange colored solid.

Example 17

2-[5,6-Dichloro-2-(2,2,2-trifluoro-ethyl)-benzoimidazol-1-yl]-1-(2,4-dimethoxy-Phenyl)-ethanone

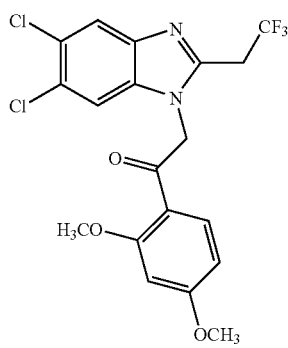

To 5,6-dichloro-2-(2,2,2-trifluoro-ethyl)-1H-benzimidazole (317 mg) in DMF (5 mL) was added sodium hydride (71 mg of 60% in oil dispersion). The resulting mixture was stirred at room temperature for 5 min. To the dark green solution was added 2-bromo-2',4'-dimethoxyacetophenone (382 mg) and the resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes) to yield the title compound as a white solid.

$^1$H NMR (300 MHz, $d_6$-DMSO): δ 7.97 (s, 1H), 7.96 (s, 1H), 7.78 (d, 1H, J=7.0 Hz), 6.67-6.70 (m, 1H), 5.75 (s, 2H), 4.13 (ABq, 2H, $J_{AB}$=11 Hz, $\Delta v_{AB}$19 Hz), 4.03 (s, 3H), 3.89 (s, 3H).

Example 18

5,6-Dichloro-1-methyl-2-(2,2,2-trifluoro-ethyl)-1H-benzoimidazole

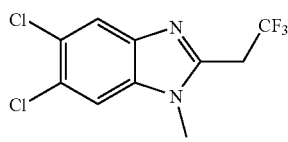

To 5,6-dichloro-2-(2,2,2-trifluoro-ethyl)-1H-benzimidazole (1 g) in DMF (20 mL) was added sodium hydride (230 mg of 60% in oil dispersion). The resulting mixture was stirred at room temperature for 5 min. To the dark green solution was added iodomethane (815 mg) and the resulting mixture was stirred at room temperature overnight. The reaction mixture was quenched with water, extracted with EtOAc, and dried over $Na_2SO_4$. The crude product was purified by silica gel chromatography (5%-25% EtOAc/hexanes) to yield the title compound as an orange solid.

$^1$H NMR (300 MHz, $CDCl_3$): δ 7.85 (s, 1H), 7.46 (s, 1H), 3.80 (ABq, 2H, $J_{AB}$=9.9 Hz, $\Delta v_{AB}$=14 Hz), 3.79 (s, 3H).

Example 19

[5,6-Dichloro-2-(2,2,2-trifluoro-ethyl)-benzoimidazol-1-yl]-acetic Acid Ethyl Ester

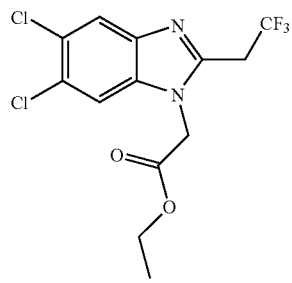

To 5,6-dichloro-2-(2,2,2-trifluoro-ethyl)-1H-benzimidazole (1 g) in DMF (5 mL) was added sodium hydride (85 mg of 60% in oil dispersion). The resulting mixture was stirred at room temperature for 5 min. To the dark green solution was added ethyl bromoacetate (363 mg) and the resulting mixture was stirred at room temperature overnight. The reaction mixture was quenched with water, extracted with EtOAc, and dried over $Na_2SO_4$. The crude product was purified by silica gel chromatography (5%-30% EtOAc/hexanes) to yield the title compound as a yellow solid.

$^1$H NMR (300 MHz, $CDCl_3$): δ 7.89 (s, 1H), 7.40 (s, 1H), 4.86 (s, 2H), 4.26 (q, 2H, J=7.1 Hz), 3.79 (ABq, 2H, $J_{AB}$=9.9 Hz, $\Delta v_{AB}$=17.1 Hz), 1.29 (t, 3H, J=7.1 Hz).

Example 20

1-Benzofuran-2-yl-2-[5,6-dichloro-2-(2,2,2-trifluoro-ethyl)-benzoimidazol-1-yl]-ethanone

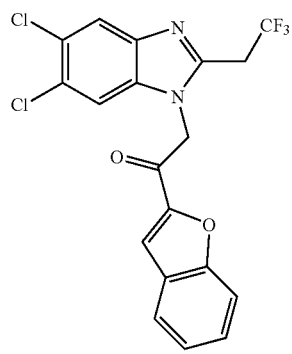

To 5,6-dichloro-2-(2,2,2-trifluoro-ethyl)-1H-benzimidazole (460.5 mg) in DMF (5 mL) was added sodium hydride (103 mg of 60% in oil dispersion). The resulting mixture was stirred at room temperature for 5 min. To the dark green solution was added 1-(1-benzofuran-2-yl)-2-bromoethan-1-one (633 mg) and the resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes) to yield the title compound as a yellow solid.

$^1$H NMR (300 MHz, $d_6$-DMSO): δ 8.10 (s, 1H), 8.08 (s, 1H), 8.01 (s, 1H), 7.95 (d, 1H, J=7.8 Hz), 7.81 (d, 1H, J=8.1 Hz), 7.62 (t, 1H, J=7.4 Hz), 7.44 (t, 1H, J=7.4 Hz), 6.05 (s, 2H), 4.23 (ABq, 2H, $J_{AB}$=10.6 Hz, $\Delta v_{AB}$=18.6 Hz).

Example 21

5,6-Dichloro-1-(4-fluoro-benzyl)-2-(2,2,2-trifluoro-ethyl)-1H-benzoimidazole

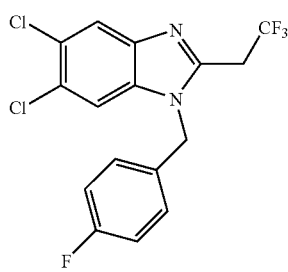

To 5,6-dichloro-2-(2,2,2-trifluoro-ethyl)-1H-benzimidazole (301 mg) in DMF (5 mL) was added potassium carbonate powder (298 mg) and 4-fluorobenzyl bromide (841 mg). The resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes) to yield the title compound as a peach colored solid.

MS (M−1)=375.0.

Example 22

5,6-Dichloro-2-(2,2,2-trifluoro-ethyl)-1-(3-trifluoromethyl-benzyl)-1H-benzoimidazole

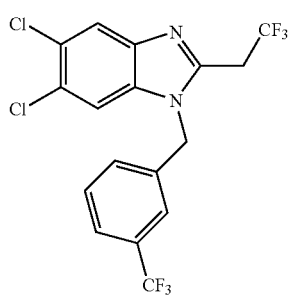

To 5,6-dichloro-2-(2,2,2-trifluoro-ethyl)-1H-benzimidazole (355 mg) in DMF (5 mL) was added potassium carbonate powder (548 mg) and 3-trifluoromethylbenzyl bromide (947 mg). The resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes) to yield the title compound as an orange solid.

$^1$H NMR (300 MHz, CDCl$_3$): δ 7.94 (s, 1H), 7.62 (d, 1H, J=8.0 Hz), 7.48 (t, 1H, J=7.8 Hz), 7.36 (s, 1H), 7.30 (s, 1H), 7.05 (d, 1H, J=8.1 Hz), 5.45 (s, 2H), 3.73 (ABq, 2H, J$_{AB}$=9.7 Hz, Δv$_{AB}$=17 Hz).

Example 23

5,6-Dichloro-1-pentafluorophenylmethyl-2-(2,2,2-trifluoro-ethyl)-1H-benzoimidazole

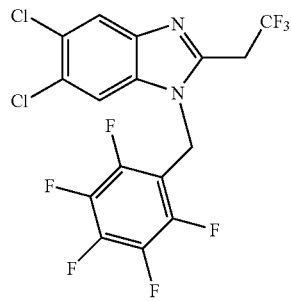

To 5,6-dichloro-2-(2,2,2-trifluoro-ethyl)-1H-benzimidazole (354 mg) in DMF (5 mL) was added potassium carbonate powder (545 mg) and 2,3,4,5,6-pentafluoromethylbenzyl bromide (1.028 g). The resulting mixture was stirred at room temperature overnight. The reaction mixture was quenched with water, extracted with EtOAc, and dried over Na$_2$SO$_4$. The crude product was purified by silica gel chromatography (10%-40% EtOAc/hexanes) to yield the title compound as a tan solid.

Example 24

5,6-Dichloro-1-(3-methyl-benzyl)-2-(2,2,2-trifluoro-ethyl)-1H-benzoimidazole

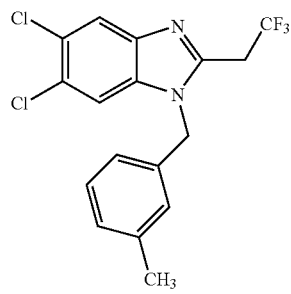

To 5,6-dichloro-2-(2,2,2-trifluoro-ethyl)-1H-benzimidazole (360 mg) in DMF (5 mL) was added potassium carbonate powder (555 mg) and 3-methylbenzyl bromide (774 mg). The resulting mixture was stirred at room temperature overnight. The reaction mixture was quenched with water, extracted with EtOAc, and dried over Na$_2$SO$_4$. The crude product was purified by silica gel chromatography (10%-40% EtOAc/hexanes) to yield the title compound as an off-white solid.

Example 25

5,6-Dichloro-1-pyridin-3-ylmethyl-2-(2,2,2-trifluoro-ethyl)-1H-benzoimidazole

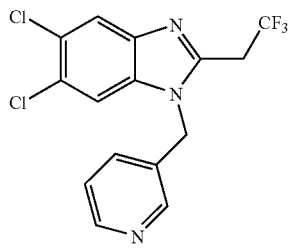

To 5,6-dichloro-2-(2,2,2-trifluoro-ethyl)-1H-benzimidazole (423 mg) in DMF (5 mL) was added potassium carbonate powder (868 mg) and 3-(bromomethyl)pyridine hydrogen bromide (615 mg). The resulting mixture was stirred at room temperature overnight. The reaction mixture was quenched with water, extracted with EtOAc, and dried over Na$_2$SO$_4$. The crude product was purified by silica gel chromatography (15%-60% EtOAc/hexanes) to yield the title compound as a green solid.

Example 26

5,6-Dichloro-1-(4-nitro-benzyl)-2-(2,2,2-trifluoro-ethyl)-1H-benzoimidazole

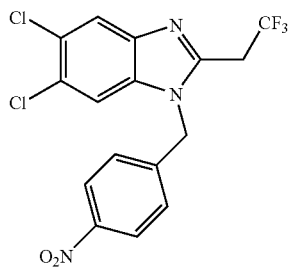

To 5,6-dichloro-2-(2,2,2-trifluoro-ethyl)-1H-benzimidazole (355 mg) in DMF (5 mL) was added sodium hydride (110 mg of 60% in oil) and 4-nitrobenzyl bromide (596 mg). The resulting mixture was stirred at room temperature overnight. The reaction mixture was quenched with water, extracted with EtOAc, and dried over Na$_2$SO$_4$. The crude product was purified by silica gel chromatography (10%-40% EtOAc/hexanes) to yield the title compound as a light orange solid.

$^1$H NMR (300 MHz, CDCl$_3$): δ 8.20 (d, 2H, J=8.8 Hz), 7.92 (s, 1H), 7.26 (s, 1H), 7.16 (d, 2H, J=8.8 Hz), 5.50 (s, 2H), 3.75 (ABq, 2H, J$_{AB}$=9.7 Hz, Δv$_{AB}$=23 Hz).

Example 27

2-[5,6-Dichloro-2-(2,2,2-trifluoro-ethyl)-benzoimidazol-1-yl]-ethanol

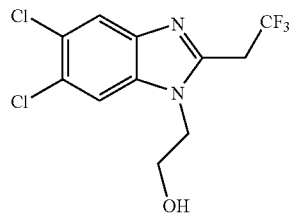

To [5,6-dichloro-2-(2,2,2-trifluoro-ethyl)-benzimidazol-1-yl]-acetic acid ethyl ester (915 mg) in toluene (20 mL) at −78° C. was added DiBAl—H (3.43 mls of 1.5 M in toluene). The resulting mixture was stirred for 1 hour. The reaction mixture was quenched with Rochelle's salt (aq), extracted with EtOAc, and dried over $Na_2SO_4$. The extracts were concentrated to a toluene solution and ethanol (10 mL) was added. To the resulting solution was added $NaBH_4$ (533 mg). The resulting mixture was stirred for 5 hour. The reaction mixture was quenched with water, extracted with EtOAc, and dried over $Na_2SO_4$. The crude product was purified by silica gel chromatography (15%-60% EtOAc/hexanes) to yield the title compound as a yellow solid.

$^1$H NMR (300 MHz, $CDCl_3$): δ 7.41 (s, 1H), 7.37 (s, 1H), 4.37 (t, 1H, J=5.1 Hz), 4.30 (t, 2H, J=4.6 Hz), 3.99-4.03 (m, 2H), 3.86 (ABq, 2H, $J_{AB}$=9.8 Hz, $\Delta v_{AB}$=17 Hz).

Example 28

5,6-Dichloro-1-[2-(4-fluoro-phenoxy)-ethyl]-2-(2,2,2-trifluoro-ethyl)-1H-benzoimidazole

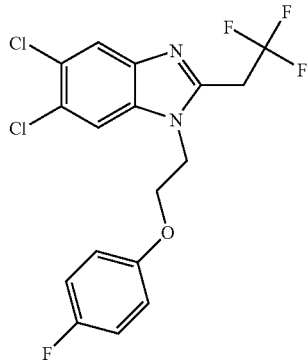

To a mixture of 2-[5,6-dichloro-2-(2,2,2-trifluoro-ethyl)-benzomidazol-1-yl]-ethanol (171 mg), 4-fluorophenol (92 mg), and triphenylphosphine (158 mg) in toluene (5 mL) at 0° C. was added diethylazodicarboxylate (0.11 mls). The resulting mixture was stirred at ambient temperature overnight. The reaction mixture was quenched with 1N HCl (aq), extracted with EtOAc, and dried over $Na_2SO_4$. The crude product was purified by silica gel chromatography (4%-25% EtOAc/hexanes) to yield the title compound as a white solid.

Example 29

5,6-Dichloro-1-[2-(3-fluoro-phenoxy)-ethyl]-2-(2,2,2-trifluoro-ethyl)-1H-benzoimidazole

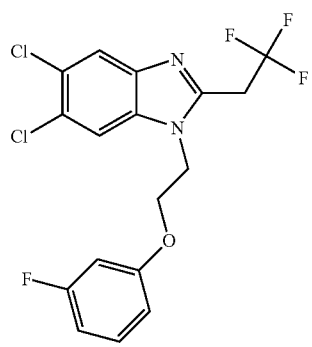

To a mixture of 2-[5,6-dichloro-2-(2,2,2-trifluoro-ethyl)-benzomidazol-1-yl]-ethanol (164 mg), 3-fluorophenol (88 mg), and triphenylphosphine (158 mg) in toluene (5 mL) at 0° C. was added diethylazodicarboxylate (0.11 mls). The resulting mixture was stirred at ambient temperature overnight. The reaction mixture was quenched with 1N HCl (aq), extracted with EtOAc, and dried over $Na_2SO_4$. The crude product was purified by silica gel chromatography (4%-25% EtOAc/hexanes) to yield the title compound as an off-white solid.

$^1$H NMR (300 MHz, $CDCl_3$): δ 7.86 (s, 1H), 7.55 (s, 1H), 7.16-7.24 (m, 1H), 6.64-6.71 (m, 1H), 6.47-6.58 (m, 2H), 4.59 (t, 2H, J=4.8 Hz), 4.25 (t, 2H, J=5.0 Hz), 3.99 (ABq, 2H, $J_{AB}$=9.9 Hz, $\Delta v_{AB}$=17 Hz).

Example 30

5,6-Dichloro-1-[2-(4-chloro-phenoxy)-ethyl]-2-(2,2,2-trifluoro-ethyl)-1H-benzoimidazole

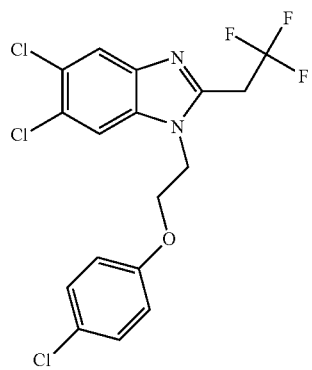

To a mixture of 2-[5,6-dichloro-2-(2,2,2-trifluoro-ethyl)-benzomidazol-1-yl]-ethanol (153 mg), 4-chlorophenol (94 mg), and triphenylphosphine (141 mg) in toluene (5 mL) at 0° C. was added diethylazodicarboxylate (0.10 mls). The resulting mixture was stirred at ambient temperature overnight. The reaction mixture was quenched with 1N HCl (aq), extracted with EtOAc, and dried over $Na_2SO_4$. The crude product was purified by silica gel chromatography (4%-25% EtOAc/hexanes) to yield the title compound as a white foamy solid.

Example 31

5,6-Dichloro-1-(3-methoxy-benzyl)-2-(2,2,2-trifluoro-ethyl)-1H-benzoimidazole

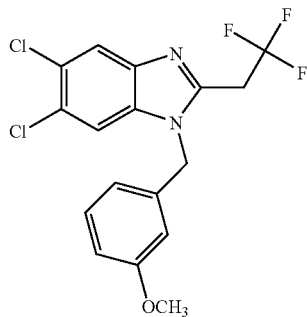

To 5,6-dichloro-2-(2,2,2-trifluoro-ethyl)-1H-benzimidazole (368 mg) in DMF (5 mL) was added potassium carbonate powder (567 mg) and 3-methoxybenzyl bromide (825 mg). The resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes), followed by dissolution in $CH_2Cl_2$ and trituration with hexanes to yield the title compound as a peach solid.

$^1$H NMR (300 MHz, $CDCl_3$): δ 7.91 (s, 1H), 7.37 (s, 1H), 7.26 (t, 1H, J=6.7 Hz), 6.86 (dd, 1H, J=8.3, 2.3 Hz), 6.55 (d, 1H, J=7.6 Hz), 6.51 (s, 1H), 5.34 (s, 2H), 3.75 (s, 3H), 3.71 (ABq, 2H, $J_{AB}$=9.8 Hz, $\Delta v_{AB}$=17 Hz).

Example 32

5,6-Dichloro-1-(2-methoxy-5-nitro-benzyl)-2-(2,2,2-trifluoro-ethyl)-1H-benzoimidazole

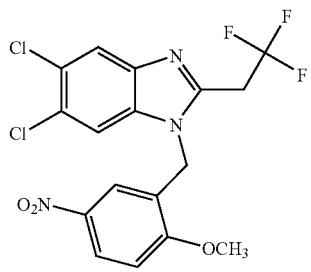

To 5,6-dichloro-2-(2,2,2-trifluoro-ethyl)-1H-benzimidazole (387 mg) in DMF (5 mL) was added potassium carbonate powder (596 mg) and 3-methoxy-5-nitro-benzyl bromide (1.06 g). The resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes) to yield the title compound as a peach-colored solid.

$^1$H NMR (300 MHz, $CDCl_3$): δ 8.25 (dd, 1H, J=9.1, 2.7 Hz), 7.91 (s, 1H), 7.58 (d, 1H, J=2.5 Hz), 7.33 (s, 1H), 7.03 (d, 1H, J=9.1 Hz), 5.37 (s, 2H), 4.01 (s, 3H), 3.82 (ABq, 2H, $J_{AB}$=9.7 Hz, $\Delta v_{AB}$=17 Hz).

Example 33

4-{2-[5,6-Dichloro-2-(2,2,2-trifluoro-ethyl)-benzoimidazol-1-yl]-ethoxy}-benzonitrile

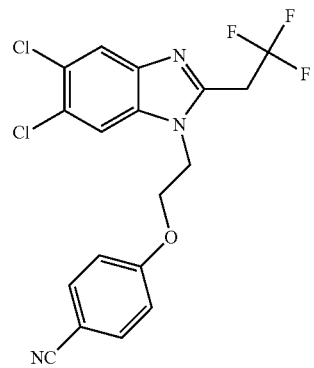

To a mixture of 2-[5,6-dichloro-2-(2,2,2-trifluoro-ethyl)-benzomidazol-1-yl]-ethanol (142 mg), 4-cyanophenol (81 mg), and triphenylphosphine (143 mg) in toluene (5 mL) at 0° C. was added ditert-butylazodicarboxylate (125 mg). The resulting mixture was stirred at ambient temperature overnight. To the mixture was added 2 drops of trifluoroacetic acid and stirred for 4 hours. The reaction mixture was quenched with 1N HCl (aq), extracted with EtOAc, and dried over $Na_2SO_4$. The crude product was purified by silica gel chromatography (5%-30% EtOAc/hexanes) to yield the title compound as a white foamy solid.

$^1$H NMR (300 MHz, $CDCl_3$): δ 7.88 (s, 1H), 7.57 (s, 1H), 7.58 (d, 2H, J=8.6 Hz), 6.86 (d, 2H, J=8.7 Hz), 4.63 (t, 2H, J=4.8 Hz), 4.33 (t, 2H, J=4.9 Hz), 3.97 (ABq, 2H, $J_{AB}$=9.8 Hz, $\Delta v_{AB}$=17 Hz).

Example 34

5,6-Dichloro-2-(2,2,2-trifluoro-ethyl)-1-(3-trifluoromethoxy-benzyl)-1H-benzoimidazole

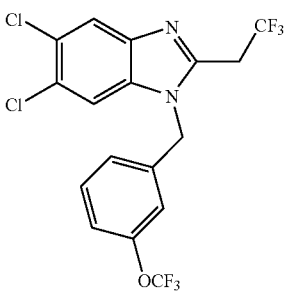

To 5,6-dichloro-2-(2,2,2-trifluoro-ethyl)-1H-benzimidazole (495 mg) in DMF (5 mL) was added potassium carbonate powder (763 mg) and 3-(trifluoromethoxy) benzyl bromide (1.41 g). The resulting mixture was stirred at room temperature overnight. The reaction mixture was quenched with water, extracted with EtOAc, and dried over Na$_2$SO$_4$. The crude product was purified by silica gel chromatography (10%-40% EtOAc/hexanes) to yield the title compound as a brown solid.

$^1$H NMR (300 MHz, CDCl$_3$): δ 7.90 (s, 1H), 7.39 (t; 1H, J=8.0 Hz), 7.31 (s, 1H), 7.20 (d, 1H, J=8.3 Hz), 6.89 (s, 1H), 6.87 (d, 1H, J=8.7 Hz), 5.40 (s, 2H), 3.73 (ABq, 2H, J$_{AB}$=9.8 Hz, Δν$_{AB}$=17 Hz).

Example 35

5,6-Dichloro-2-(2,2,2-trifluoro-ethyl)-1-(4-trifluoromethylsulfanyl-benzyl)-1H-benzoimidazole

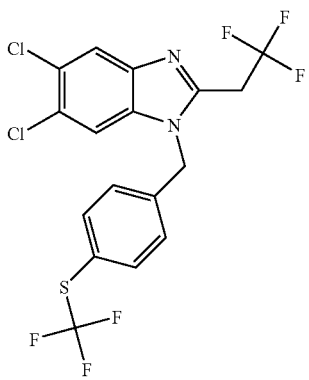

To 5,6-dichloro-2-(2,2,2-trifluoro-ethyl)-1H-benzimidazole (434 mg) in DMF (5 mL) was added potassium carbonate powder (669 mg) and 4-(trifluoromethylthio) benzyl bromide (596 mg). The resulting mixture was stirred at room temperature overnight. The reaction mixture was quenched with water, extracted with EtOAc, and dried over Na$_2$SO$_4$. The crude product was purified by silica gel chromatography (10%-40% EtOAc/hexanes) to yield the title compound as a brown solid.

$^1$H NMR (300 MHz, CDCl$_3$): δ 7.91 (s, 1H), 7.64 (d, 2H, J=8.2 Hz), 7.31 (s, 1H), 7.03 (d, 2H, J=8.3 Hz), 5.42 (s, 2H), 3.71 (ABq, 2H, J$_{AB}$=9.8 Hz, Δν$_{AB}$=17 Hz).

Example 36

5,6-Dichloro-1-(2-nitro-benzyl)-2-(2,2,2-trifluoro-ethyl)-1H-benzoimidazole

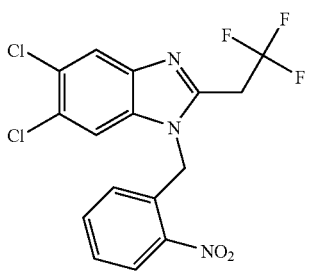

To 5,6-dichloro-2-(2,2,2-trifluoro-ethyl)-1H-benzimidazole (319 mg) in DMF (5 mL) was added potassium carbonate powder (491 mg) I) and 2-nitrobenzyl bromide (768 mg). The resulting mixture was stirred at room temperature overnight. The reaction mixture was quenched with water, extracted with EtOAc, and dried over Na$_2$SO$_4$. The crude product was purified by silica gel chromatography (5%-35% EtOAc/hexanes), followed by dissolution in CH$_2$Cl$_2$ and trituration with hexanes to yield the title compound as orange solid.

$^1$H NMR (300 MHz, CDCl$_3$): δ 7.96 (s, 1H), 7.49-7.61 (m, 2H), 7.24 (s, 1H), 6.42-6.45 (m, 1H), 5.83 (s, 2H), 3.74 (ABq, 2H, J$_{AB}$=9.7 Hz, Δν$_{AB}$=17 Hz).

Example 37

5,6-Dichloro-1-(3-nitro-benzyl)-2-(2,2,2-trifluoro-ethyl)-1H-benzoimidazole

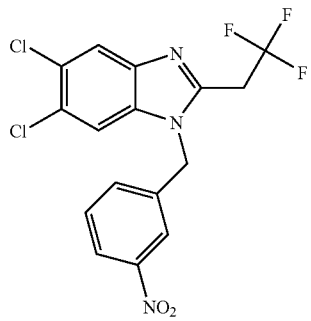

To 5,6-dichloro-2-(2,2,2-trifluoro-ethyl)-1H-benzimidazole (355 mg) in DMF (5 mL) was added sodium hydride (110 mg of 60% in oil) and 3-nitrobenzyl bromide (596 mg). The resulting mixture was stirred at room temperature overnight. The reaction mixture was quenched with water, extracted with EtOAc, and dried over Na$_2$SO$_4$. The crude product was purified by silica gel chromatography (10%-40% EtOAc/hexanes) to yield the title compound as a red solid.

$^1$H NMR (300 MHz, CDCl$_3$): δ 8.22 (d, 1H, J=7.8 Hz), 7.96 (d, 1H, J=11.8 Hz), 7.94 (s, 1H), 7.56 (t, 1H, J=7.9 Hz), 7.27 (s, 1H), 7.21 (s, 1H, J=7.7 Hz), 5.50 (s, 2H), 3.76 (ABq, 2H, J$_{AB}$=9.5 Hz, Δν$_{AB}$=17 Hz).

Example 38

5,6-Dichloro-1-(4-methanesulfonyl-benzyl)-2-(2,2,2-trifluoro-ethyl)-1H-benzoimidazole

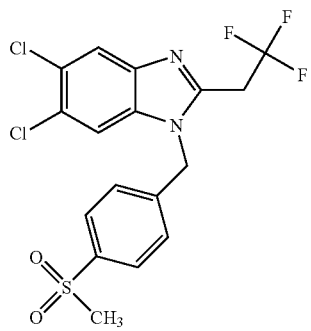

To 5,6-dichloro-2-(2,2,2-trifluoro-ethyl)-1H-benzimidazole (483 mg) in DMF (5 mL) was added potassium carbonate powder (744 mg) and 4-methylsulphonylbenzyl bromide (1.68 g). The resulting mixture was stirred at room temperature overnight. The reaction mixture was quenched with water, extracted with EtOAc, and dried over $Na_2SO_4$. The crude product was purified by silica gel chromatography (10%-40%-75% EtOAc/hexanes) to yield the title compound as an off-white solid.

$^1$H NMR (400 MHz, $CDCl_3$): δ 7.94 (s, 1H), 7.93 (d, 2H, J=7.9 Hz), 7.27 (s, 1H), 7.17 (d, 2H, J=8.3 Hz), 5.48 (s, 2H), 3.74 (ABq, 2H, $J_{AB}$=9.7 Hz, $Δv_{AB}$=17 Hz), 3.06 (s, 3H).

Example 39

[5,6-Dichloro-2-(2,2,2-trifluoro-ethyl)-benzoimidazol-1-yl]-acetonitrile

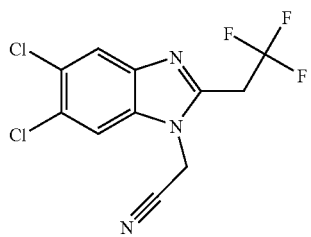

To 5,6-dichloro-2-(2,2,2-trifluoro-ethyl)-1H-benzimidazole (356 mg) in DMF (5 mL) was added sodium hydride (79 mg of 60% in oil) and iodoacetonitrile (331 mg). The resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes), followed by washing solid with $CH_2Cl_2$ to yield the title compound as a peach-colored solid.

$^1$H NMR (300 MHz, $d_6$-DMSO): δ 8.15 (s, 1H), 8.07 (s, 1H), 5.73 (s, 2H), 4.31 (ABq, 2H, $J_{AB}$=11 Hz, $Δv_{AB}$=19 Hz).

Example 40

5,6-Dichloro-1-(2-methyl-benzyl)-2-(2,2,2-trifluoro-ethyl)-1H-benzoimidazole

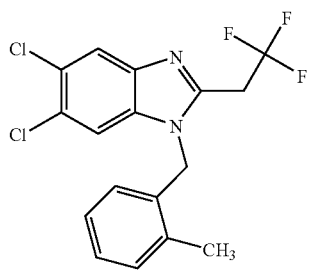

To 5,6-dichloro-2-(2,2,2-trifluoro-ethyl)-1H-benzimidazole (583 mg) in DMF (6 mL) was added potassium carbonate powder (900 mg) and 2-methylbenzyl bromide (1.2 g). The resulting mixture was stirred at room temperature overnight. The reaction mixture was quenched with water, extracted with EtOAc, and dried over $Na_2SO_4$. The crude product was purified by silica gel chromatography (10%-40% EtOAc/hexanes), followed by washing solid with hexanes to yield the title compound as a tan solid.

$^1$H NMR (300 MHz, $CDCl_3$): δ 7.93 (s, 1H), 7.29 (s, 1H), 7.22-7.26 (m, 2H), 7.04-7.10 (m, 1H), 6.31 (d, 1H, J=7.9 Hz), 5.33 (s, 2H), 3.65 (ABq, 2H, $J_{AB}$=9.8 Hz, $Δv_{AB}$=17 Hz).

Example 41

5,6-Dichloro-2-(2,2,2-trifluoro-ethyl)-1-(2-trifluoromethyl-benzyl)-1H-benzoimidazole

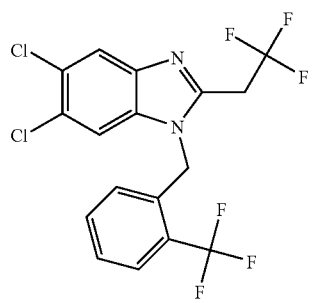

To 5,6-dichloro-2-(2,2,2-trifluoro-ethyl)-1H-benzimidazole (577 mg) in DMF (6 mL) was added potassium carbonate powder (890 mg) and 2-(trifluoromethyl)benzyl bromide (1.54 g). The resulting mixture was stirred at room temperature overnight. The reaction mixture was quenched with water, extracted with EtOAc, and dried over $Na_2SO_4$. The crude product was purified by silica gel chromatography (5%-40% EtOAc/hexanes), followed by recrystallization with hexanes to yield the title compound as an orange-brown solid.

$^1$H NMR (300 MHz, $CDCl_3$): δ 7.95 (s, 1H), 7.80 (d, 1H, J=7.2 Hz), 7.38-7.48 (m, 2H), 7.29 (s, 1H), 6.44 (d, 1H, J=7.5 Hz), 5.58 (s, 2H), 3.68 (ABq, 2H, $J_{AB}$=9.7 Hz, $Δv_{AB}$=17 Hz).
MS (M+1)=427.0

Example 42

1-(2,4-Bis-trifluoromethyl-benzyl)-5,6-dichloro-2-(2,2,2-trifluoro-ethyl)-1H-benzoimidazole

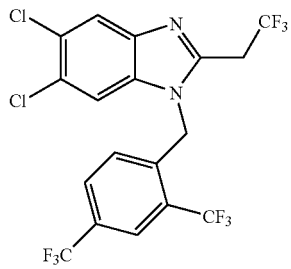

To 5,6-dichloro-2-(2,2,2-trifluoro-ethyl)-1H-benzimidazole (622 mg) in DMF (7 mL) was added potassium carbonate powder (958 mg) and 2,4-bis(trifluoromethyl)-benzyl bromide (2.13 g). The resulting mixture was stirred at room temperature overnight. The reaction mixture was quenched with water, extracted with EtOAc, and dried over $Na_2SO_4$. The crude product was purified by silica gel chromatography (5%-40% EtOAc/hexanes), followed by recrystallization with hexanes to yield the title compound as an orange solid.

¹H NMR (300 MHz, CDCl₃): δ 8.05 (s, 1H), 7.97 (s, 1H), 7.68 (d, 1H, J=8.1 Hz), 7.25 (s, 1H), 6.59 (d, 1H, J=8.2 Hz), 5.63 (s, 2H), 3.71 (ABq, 2H, J$_{AB}$=9.7 Hz, Δv$_{AB}$=17 Hz).
MS (M−1)=492.9

Example 43

1-(2-Benzenesulfonylmethyl-benzyl)-5,6-dichloro-2-(2,2,2-trifluoro-ethyl)-1H-benzoimidazole

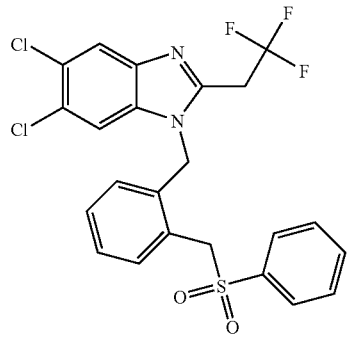

To 5,6-dichloro-2-(2,2,2-trifluoro-ethyl)-1H-benzimidazole (629 mg) in DMF (7 mL) was added potassium carbonate powder (969 mg) and 1-bromomethyl-2-[phenylsulfonyl)methyl]benzyl bromide (2.28 g). The resulting mixture was stirred at room temperature overnight. The reaction mixture was quenched with water, extracted with EtOAc, and dried over Na₂SO₄. The crude product was purified by silica gel chromatography (5%-40% EtOAc/hexanes), followed by recrystallization with hexanes to yield the title compound as a yellow solid.

¹H NMR (300 MHz, CDCl₃): δ 7.94 (s, 1H), 7.78 (d, 1H, J=7.1 Hz), 7.69-7.77 (m, 1H), 7.59 (d, 2H, J=7.9 Hz), 7.36 (s, 1H), 7.14-7.23 (m, 2H), 6.89 (dd, 1H, J=6.8, 1.5 Hz), 6.32 (dd, 1H, J=8.7, 6.8 Hz), 5.69 (s, 2H), 4.44 (s, 2H), 3.76 (ABq, 2H, J$_{AB}$=9.8 Hz, Δv$_{AB}$=17 Hz).

Example 44

1-Biphenyl-2-ylmethyl-5,6-dichloro-2-(2,2,2-trifluoro-ethyl)-1H-benzoimidazole

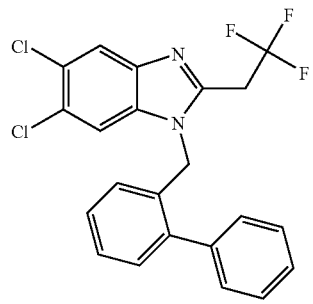

To 5,6-dichloro-2-(2,2,2-trifluoro-ethyl)-1H-benzimidazole (521 mg) in DMF (5 mL) was added potassium carbonate powder (802 mg) and 2-phenyl benzyl bromide (1.43 g). The resulting mixture was stirred at room temperature overnight. The reaction mixture was quenched with water, extracted with EtOAc, and dried over Na₂SO₄. The crude product was purified by silica gel chromatography (5%-40% EtOAc/hexanes), followed by recrystallization with Et₂O/hexanes to yield the title compound as a white solid.

¹H NMR (300 MHz, CDCl₃): δ 7.84 (s, 1H), 7.20-7.48 (m, 8H), 7.43 (s, 1H), 6.84 (d, 1H, J=7.5 Hz), 5.25 (s, 2H), 3.40 (ABq, 2H, J$_{AB}$=9.8 Hz, Δv$_{AB}$=17 Hz).

Example 46

5,6-Dichloro-1-methoxymethyl-2-(2,2,2-trifluoro-ethyl)-1H-benzoimidazole

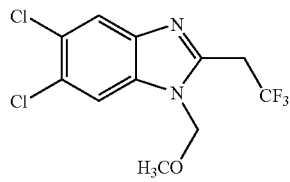

NaH (60%) (44.6 mg, 1.1153 mmol) was added into a solution of dichloro-2-(2,2,2-trifluoro-ethyl)-1H-benzoimidazole (200 mg, 0.7435 mmol) in DMF (5 ml) at 0° C. The resulting mixture was stirred at 0° C. for half hour. Bromomethyl methyl ether (139.4 mg, 0.09 ml, 1.1153 mmol) was added at 0° C. The reaction temperature was raised to 25° C. and stirred for 18 hours. NH₄Cl (aq.) was added and extracted with EtOAc. The organic layer was washed with brine, then dried over anhydrous MgSO₄. Solvent was distilled out under reduced pressure. Column chromatography (silica gel, EtOAc/hexanes 0% to 30%) yielded the title compound as a brown solid.

MS m/z (M+H) 232

Example 47

5,6-Dichloro-1-methylsulfanylmethyl-2-(2,2,2-trifluoro-ethyl)-1H-benzoimidazole

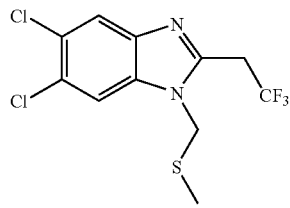

NaH (60%) (44.6 mg, 1.1153 mmol) was added into a solution of dichloro-2-(2,2,2-trifluoro-ethyl)-1H-benzoimidazole (200 mg, 0.7435 mmol) in DMF (5 ml) at 0° C. The resulting mixture was stirred at 0° C. for half hour. Chloromethyl methyl sulfide (108 mg, 0.092 ml, 1.1153 mmol) was added at 0° C. The reaction temperature was raised to 25° C. and the reaction mixture was stirred for 18 hours. NH₄Cl (aq.) was added and the reaction mixture was extracted with EtOAc. The organic layer was washed with brine, then dried over anhydrous MgSO₄. Solvent was distilled out under reduced pressure. Column chromatography (silica gel, EtOAc/hexanes 0% to 30%) yield the title compound as a yellow solid.

MS m/z (M+H) 329, (M−H) 327

Example 48

5,6-Dichloro-1-methanesulfonylmethyl-2-(2,2,2-trifluoro-ethyl)-1H-benzoimidazole

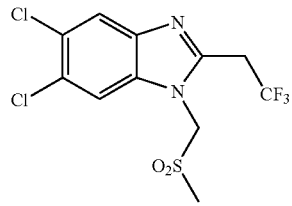

Oxone® (614.8 mg, 1 mmol) was dissolved in water (10 ml) and the pH was adjusted to pH7 with NaHCO₃. To the solution was then added tetrabutylammonium hydrogen sulfate (20 mg). The resulting solution was added at room temperature to a solution of 5,6-dichloro-1-methylsulfanylmethyl-2-(2,2,2-trifluoro-ethyl)-1H-benzoimidazole, prepared as in Example 47, (109.6 mg, 0.33 mmol) in EtOAc (4 mL). The Oxone® solution (608.87 mg) was added until the reaction completed. The resulting mixture was washed with 1N NaOH, then extracted with EtOAc. The organic layer was washed with 15% NaCl, dried over MgSO₄ and the solvent was distilled under reduced pressure to yield the title compound as a yellow solid.

MS m/z (M+H) 361

Example 49

1-(4-Bromo-phenyl)-2-[5,6-dichloro-2-(2,2,2-trifluoro-ethyl)-benzoimidazol-1-yl]-ethanone

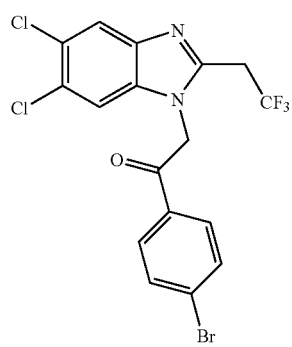

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2,4'-dibromoacetophenone (417 mg, 1.5 mmol) was then added to the reaction mixture at 0° C. The reaction temperature was raised to 25° C. and the reaction mixture was stirred for 18 hours. NH₄Cl (aq.) was added and the reaction mixture was extracted with EtOAc. The organic layer was washed with brine, then dried over anhydrous MgSO₄. The solvent was distilled out under reduced pressure. Column chromatography (silica gel, EtOAc/hexanes 0% to 55%) yielded the title compound as a yellow solid.

MS m/z (M−H) 464.

Example 50

1-[5,6-Dichloro-2-(2,2,2-trifluoro-ethyl)-benzoimidazol-1-yl]-butan-2-one

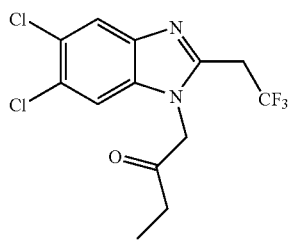

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 1-bromo-2-butanone (226.5 mg, 1.5 mmol) was then added to the reaction mixture at 0° C. The reaction temperature was raised to 25° C. and the reaction mixture was then stirred for 18 hours. NH₄Cl (aq.) was added and the reaction mixture was extracted with EtOAc. The organic layer was washed with brine, then dried over anhydrous MgSO₄. The solvent was distilled out under reduced pressure. Column chromatography (silica gel, EtOAc/hexanes 0% to 55%) yielded the title compound as an off-white solid.

MS m/z (M+H) 339.

Example 51

1-(4-Chloro-phenyl)-2-[5,6-dichloro-2-(2,2,2-trifluoro-ethyl)-benzoimidazol-1-yl]-ethanone

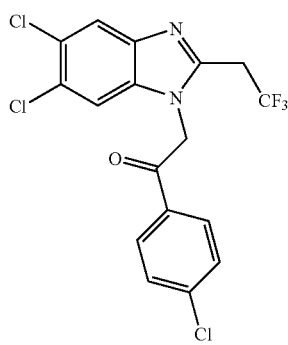

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-bromo-4'-chloroacetophenone (350.25 mg, 1.5 mmol) was then added to the reaction mixture at 0° C. The reaction temperature was raised to 25° C. and the reaction mixture was then stirred for 18 hours. NH₄Cl (aq.) was added and the reaction mixture was extracted with EtOAc. The organic layer was washed with brine, then dried over anhydrous MgSO₄. The solvent was distilled out under

Example 52

2-[5,6-Dichloro-2-(2,2,2-trifluoro-ethyl)-benzoimidazol-1-yl]-1-(3-methoxy-phenyl)-ethanone

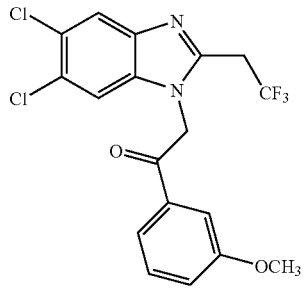

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-bromo-3'-methoxyacetophenone (343.5 mg, 1.5 mmol) was then added to the reaction mixture at 0° C. The reaction temperature was raised to 25° C. and the reaction mixture was then stirred for 18 hours. NH$_4$Cl (aq.) was added and the reaction mixture was extracted with EtOAc. The organic layer was washed with brine, then dried over anhydrous MgSO$_4$. The solvent was distilled out under reduced pressure. Column chromatography (silica gel, EtOAc/hexanes 0% to 60%) yielded the title compound as a yellow solid.

MS m/z (M−H) 415.

Example 53

2-[5,6-Dichloro-2-(2,2,2-trifluoro-ethyl)-benzoimidazol-1-yl]-1-pyridin-3-yl-ethanone

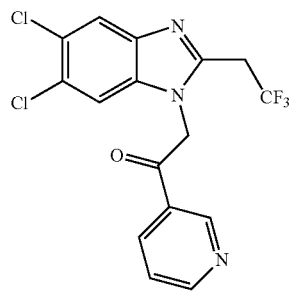

NaH (60%) (120 mg, 3 mmol) was added into a solution of dichloro-2-(2,2,2-trifluoro-ethyl)-1H-benzoimidazole) (269 mg, 1 mmol) in DMF (5 ml) at 0° C. The resulting mixture was stirred at 0° C. for half hour. 2-bromo-1-pyridin-3-ylethan-1-one hydrobromide (421.43 mg, 1.5 mmol) was then added to the reaction mixture at 0° C. The reaction temperature was raised to 25° C. and the reaction mixture was then stirred for 18 hours. NH$_4$Cl (aq.) was added and the reaction mixture was then extracted with EtOAc. The organic layer was washed with brine, then dried over anhydrous MgSO$_4$. The solvent was distilled out under reduced pressure. Column chromatography (silica gel, EtOAc/hexanes 30% to 100%) yielded the title compound as an off-white solid.

MS m/z (M−H) 386.

Example 54

2-[5,6-Dichloro-2-(2,2,2-trifluoro-ethyl)-benzoimidazol-1-yl]-1-(5-pyridin-2-yl-thiophen-2-yl)-ethanone

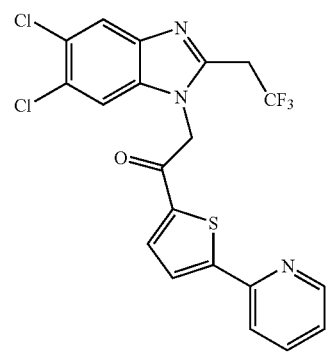

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-bromo-1-[5-(2-pyridinyl)-2-thienyl]-1-ethanone (423.24 mg, 1.5 mmol) was then added to the reaction mixture at 0° C. The reaction temperature was raised to 25° C. and the reaction mixture was then stirred for 18 hours. NH$_4$Cl (aq.) was added and the reaction mixture was then extracted with EtOAc. The organic layer was washed with brine, then dried over anhydrous MgSO$_4$. The solvent was distilled out under reduced pressure. Column chromatography (silica gel, EtOAc/hexanes 50% to 100%) yielded the title compound as a yellow solid.

MS m/z (M−H) 468.

Example 55

2-[5,6-Dichloro-2-(2,2,2-trifluoro-ethyl)-benzoimidazol-1-yl]-1-(2-methoxy-phenyl)-ethanone

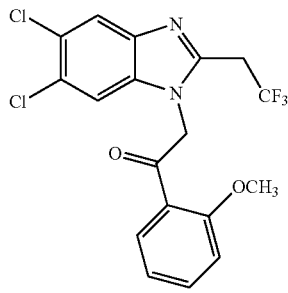

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-bromo-2'-methoxy-acetophenone (350.25 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes 5% to 60%) to yield the title compound as a yellow solid.

MS m/z (M−H) 415.

Example 56

2-[5,6-Dichloro-2-(2,2,2-trifluoro-ethyl)-benzoimidazol-1-yl]-1-thiophen-2-yl-ethanone

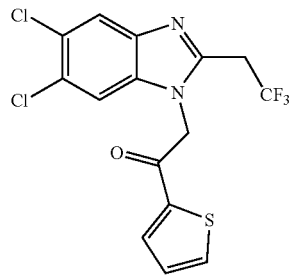

NaH (60%) (60 mg, 1.5 mmol) was added into a solution of dichloro-2-(2,2,2-trifluoro-ethyl)-1H-benzoimidazole) (269 mg, 1 mmol) in DMF (5 ml) at 0° C. The resulting mixture was stirred at 0° C. for half hour. 2-bromo-1-(2-thienyl)-1-ethanone (307.5 mg, 1.5 mmol) was then added to the reaction mixture at 0° C. The reaction temperature was raised to 25° C. and then the reaction mixture was stirred for 18 hours. NH₄Cl (aq.) was added and the reaction mixture was extracted with EtOAc. The organic layer was washed with brine, then dried over anhydrous MgSO₄. The solvent was distilled out under reduced pressure. Column chromatography (silica gel, EtOAc/hexanes 0% to 60%) yielded the title compound as a brown solid.

MS m/z (M+H) 393, (M−H) 391.

Example 57

2-[5,6-Dichloro-2-(2,2,2-trifluoro-ethyl)-benzoimidazol-1-yl]-1-pyridin-2-yl-ethanone

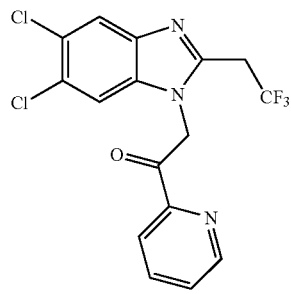

NaH (60%) (120 mg, 3 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-bromo-1-(2-pyridiny)-1-ethanone hydrobromide (421.4 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes 0% to 70%) yielded the title compound as a yellow solid.

MS m/z (M+H) 388, (M−H) 386.

Example 58

2-[5,6-Dichloro-2-(2,2,2-trifluoro-ethyl)-benzoimidazol-1-yl]-1-(3-nitro-phenyl)-ethanone

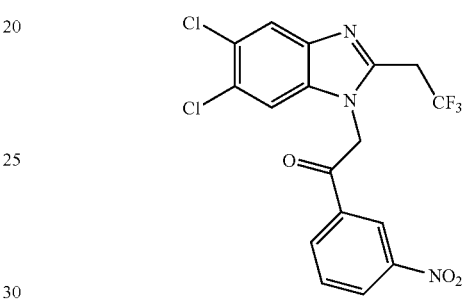

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-bromo-3'nitroacetophenone (366 mg, 1.5 mmol) was then added to the reaction mixture at 0° C. The reaction temperature was raised to 25° C. and the reaction mixture was then stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes 0% to 70%) yielded the title compound as a light brown solid.

MS m/z (M−H) 430.

Example 59

2-[5,6-Dichloro-2-(2,2,2-trifluoro-ethyl)-benzoimidazol-1-yl]-1-(4-nitro-phenyl)-ethanone

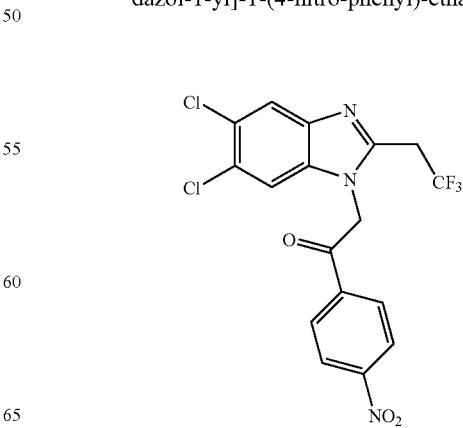

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-bromo-4'nitroacetophenone (366 mg, 1.5 mmol) was then added to the reaction mixture at 0° C. The reaction temperature was raised to 25° C. and the reaction mixture was then stirred for 18 hours. NH₄Cl (aq.) was added and the reaction mixture was extracted with EtOAc. The organic layer was washed with brine, then dried over anhydrous MgSO₄. The solvent was distilled out under reduced pressure. Column chromatography (silica gel, EtOAc/hexanes 0% to 70%) yielded the title compound as a light brown solid.

MS m/z (M+H) 432, (M−H) 430.

Example 60

1-Benzyl-5,6-dichloro-2-(2,2,2-trifluoro-ethyl)-1H-benzoimidazole

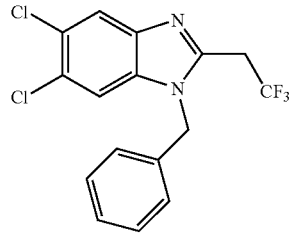

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. Benzyl bromide (256.5 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes 0% to 40%) yielded the title compound as a light brown solid.

MS m/z (M+H) 359, (M−H) 357.

Example 61

5,6-Dichloro-2-(2,2,2-trifluoro-ethyl)-1-(4-trifluoromethyl-benzyl)-1H-benzoimidazole

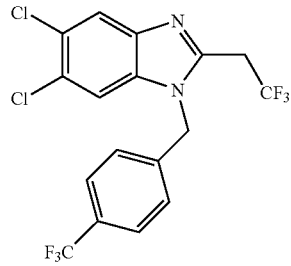

NaH (60%) (60 mg, 1.5 mmol) was added into a solution of dichloro-2-(2,2,2-trifluoro-ethyl)-1H-benzoimidazole (269 mg, 1 mmol). in DMF (5 ml) at 0° C. The resulting mixture was stirred at 0° C. for half hour. 4-(trifluoromethyl)-benzyl bromide (358.5 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes 0% to 50%) yielded the title compound as an off-white solid.

MS m/z (M+H) 427.

Example 62

5,6-Dichloro-2-(2,2,2-trifluoro-ethyl)-1-(4-trifluoromethoxy-benzyl)-1H-benzoimidazole

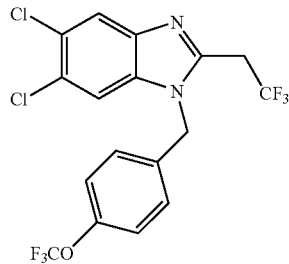

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 4-(trifluoromethoxy)-benzyl bromide (382.5 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes 0% to 60%) yielded the title compound as a brown solid.

MS m/z (M+H) 443.

Example 63

5,6-Dichloro-1-pyridin-2-ylmethyl-2-(2,2,2-trifluoro-ethyl)-1H-benzoimidazole

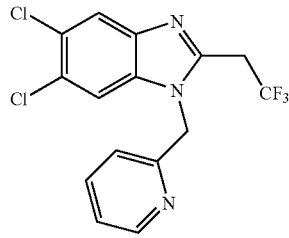

NaH (60%) (120 mg, 3 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-(bromomethyl)-pyridine hydrobromide (379.5 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes 30% to 100%) yielded the title compound as a yellow solid.

MS m/z (M+H) 360.

Example 64

2-[5,6-Dichloro-2-(2,2,2-trifluoro-ethyl)-benzoimidazol-1-yl]-1-(2,3-dihydro-benzo[1,4]dioxin-6-yl)-ethanone

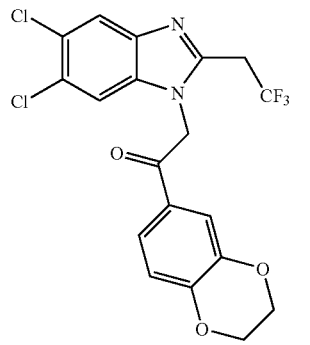

NaH (60%) (60 mg, 1.5 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 2-bromo-1-(2,3-dihydro-1,4-benzodioxin-6-yl)ethann-1-one (385.5 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. The residue was triturated with DCM to yield the title compound as a yellow solid.

MS m/z (M−H) 443.

Example 65

5,6-Dichloro-1-pyridin-4-ylmethyl-2-(2,2,2-trifluoro-ethyl)-1H-benzoimidazole

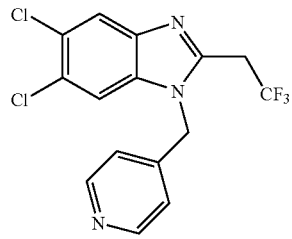

NaH (60%) (120 mg, 3 mmol) was added into a solution of dichloro-2-(2,2,2-trifluoro-ethyl)-1H-benzoimidazole (269 mg, 1 mmol) in DMF (5 ml) at 0° C. The resulting mixture was stirred at 0° C. for half hour. 4-(bromomethyl)-pyridine hydrobromide (379.5 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (30% to 100%) yielded the title compound as a white solid.

MS m/z (M+H) 360.

Example 66

3-[5,6-Dichloro-2-(2,2,2-trifluoro-ethyl)-benzoimidazol-1-ylmethyl]-benzonitrile

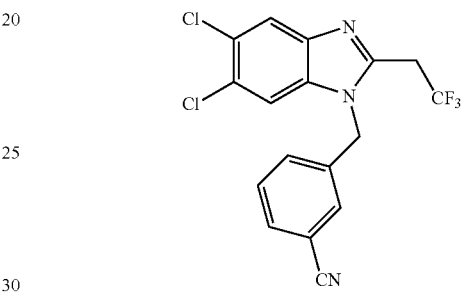

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. α-bromo-m-tolunitrile (294 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 60%) yielded the title compound as an off-white solid.

MS m/z (M+H) 384; (M−H) 382.

Example 67

2-[5,6-Dichloro-2-(2,2,2-trifluoro-ethyl)-benzoimidazol-1-ylmethyl]-benzonitrile

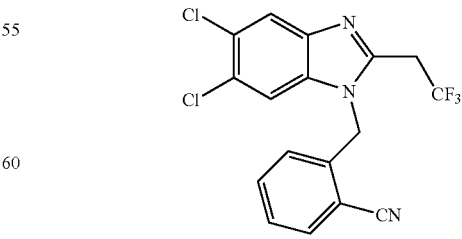

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. α-bromo-o-tolunitrile (294 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 60%) yielded the title compound as an off-white solid.

MS m/z (M+H) 384.

Example 68

2-[5,6-Dichloro-2-(2,2,2-trifluoro-ethyl)-benzoimidazol-1-yl]-1-(5-methyl-3-phenyl-isoxazol-4-yl)-ethanone

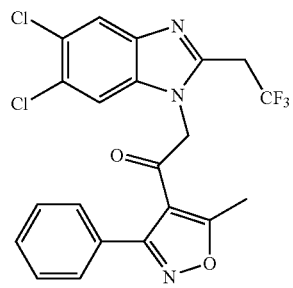

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hours. 2-bromo-1-(5-methyl-3-phenylisoxazol-4-yl)ethan-1-one (420 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 60%) yielded the title compound as a white solid.

MS m/z (M+H) 466.

Example 69

4-[5,6-Dichloro-2-(2,2,2-trifluoro-ethyl)-benzoimidazol-1-ylmethyl]-benzonitrile

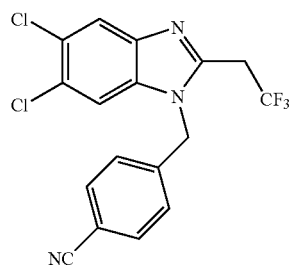

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. α-bromo-p-tolunitrile (294 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 60%) yielded the title compound as a brown solid.

MS m/z (M−H) 381.

Example 70

5,6-Dichloro-1-(2-fluoro-benzyl)-2-(2,2,2-trifluoro-ethyl)-1H-benzoimidazole

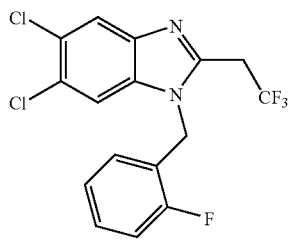

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. 2-fluorobenzyl bromide (283.5 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 60%) yielded the title compound as a light yellow solid.

MS m/z (M+H) 377.

Example 71

5,6-Dichloro-1-(3-fluoro-benzyl)-2-(2,2,2-trifluoro-ethyl)-1H-benzoimidazole

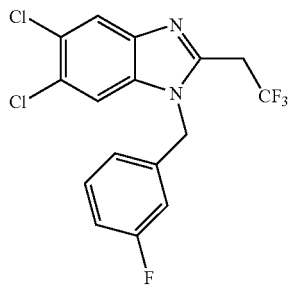

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. 3-fluorobenzyl bromide (283.5 mg, 1.5 mmol) was then added to the reaction mixture at 0° C. The reaction temperature was raised to 25° C. and then the reaction mixture was stirred for 18 hours. NH$_4$Cl (aq.) was added and extracted with EtOAc. The organic layer was washed with brine, then dried over anhydrous MgSO$_4$. The solvent was distilled out under reduced pressure. Column chromatography (silica gel, EtOAc/hexanes (0% to 60%) yielded the title compound as an off-white solid.

MS m/z (M+H) 377.

Example 72

5,6-Dichloro-1-(3-chloro-benzyl)-2-(2,2,2-trifluoro-ethyl)-1H-benzoimidazole

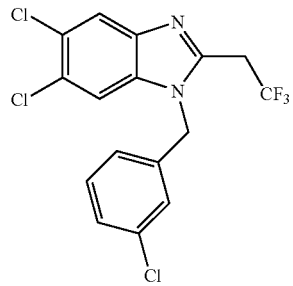

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. 3-chlorobenzyl bromide (308.25 mg, 1.5 mmol) was then added to the reaction mixture at 0° C. The reaction temperature was raised to 25° C. and then the reaction mixture was stirred for 18 hours. NH$_4$Cl (aq.) was added and extracted with EtOAc. The organic layer was washed with brine, then dried over anhydrous MgSO$_4$. The solvent was distilled out under reduced pressure. Column chromatography (silica gel, EtOAc/hexanes (0% to 60%) yielded the title compound as a yellow solid.

MS m/z (M+H) 393.

Example 73

5,6-Dichloro-1-(4-chloro-benzyl)-2-(2,2,2-trifluoro-ethyl)-1H-benzoimidazole

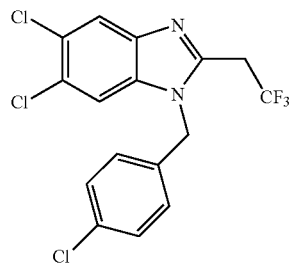

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. 4-chlorobenzyl bromide (308.25 mg, 1.5 mmol) was then added to the reaction mixture at 0° C. The reaction temperature was raised to 25° C. and then the reaction mixture was stirred for 18 hours. NH$_4$Cl (aq.) was added and extracted with EtOAc. The organic layer was washed with brine, then dried over anhydrous MgSO$_4$. The solvent was distilled out under reduced pressure. Column chromatography (silica gel, EtOAc/hexanes (0% to 60%) yielded the title compound as a yellow solid.

MS m/z (M−H) 393.

Example 74

5,6-Dichloro-1-(2-chloro-benzyl)-2-(2,2,2-trifluoro-ethyl)-1H-benzoimidazole

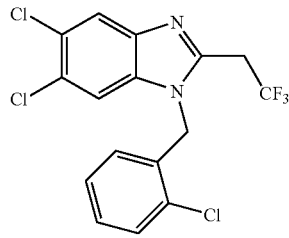

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. 2-chlorobenzyl bromide (283.5 mg, 1.5 mmol) was then added to the reaction mixture at 0° C. The reaction temperature was raised to 25° C. and then the reaction mixture was stirred for 18 hours. NH$_4$Cl (aq.) was added and extracted with EtOAc. The organic layer was washed with brine, then dried over anhydrous MgSO$_4$. The solvent was distilled out under reduced pressure. Column chromatography (silica gel, EtOAc/hexanes (0% to 60%) yielded the title compound as an off-white solid.

MS m/z (M+H) 393.

Example 75

5,6-Dichloro-1-(4-pyrazol-1-yl-benzyl)-2-(2,2,2-trifluoro-ethyl)-1H-benzoimidazole

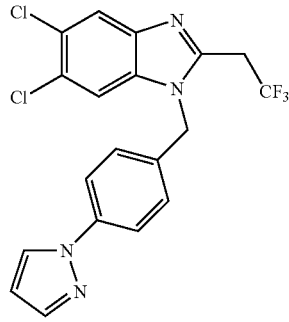

NaH (60%) (60 mg, 1.5 mmol) was added into a solution of dichloro-2-(2,2,2-trifluoro-ethyl)-1H-benzoimidazole. 5,6-

Dichloro-2-(2,2,2-trifluoro-ethyl)-1H-indole (269 mg, 1 mmol) in DMF (5 ml) at 0° C. The resulting mixture was stirred at 0° C. for half hour. 1-[4-(bromomethyl)-phenyl]-1H-pyrazole (356 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 60%) yielded the title compound as a yellow solid.

MS m/z (M+H) 425.

Example 76

5,6-Dichloro-1-(4-[1,2,3]thiadiazol-4-yl-benzyl)-2-(2,2,2-trifluoro-ethyl)-1H-benzoimidazole

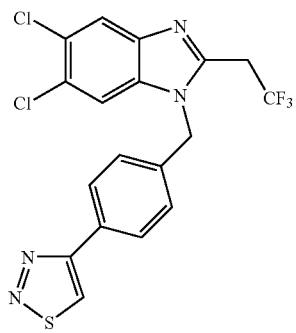

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. 4-[4-(bromomethyl)-phenyl]-1,2,3-thiazole (382.7 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 60%) yielded the title compound as a yellow solid.

MS m/z (M+H) 443.

Example 77

5,6-Dichloro-1-(5-methyl-isoxazol-4-ylmethyl)-2-(2,2,2-trifluoro-ethyl)-1H-benzoimidazole

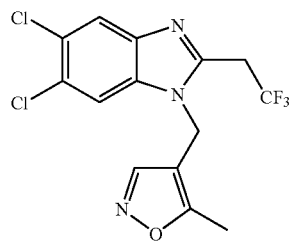

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. 3-(bromomethyl)-5-methylisoxazole (264 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 60%) yielded the title compound as a yellow solid.

MS m/z (M−H) 363.

Example 78

5,6-Dichloro-1-(4-pyrrol-1-yl-benzyl)-2-(2,2,2-trifluoro-ethyl)-1H-benzoimidazole

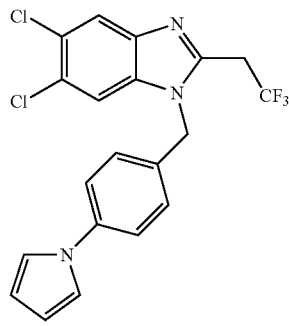

NaH (60%) (60 mg, 1.5 mmol) was added into a solution of dichloro-2-(2,2,2-trifluoro-ethyl)-1H-benzoimidazole. 5,6-Dichloro-2-(2,2,2-trifluoro-ethyl)-1H-indole (269 mg, 1 mmol) in DMF (5 ml) at 0° C. The resulting mixture was stirred at 0° C. for half hour. 1-[4-(bromomethyl)phenyl]-1H-pyrrol (354 mg, 1.5 mmol) was then added to the reaction mixture at 0° C. The reaction temperature was raised to 25° C. and then the reaction mixture was stirred for 18 hours. NH₄Cl (aq.) was added and extracted with EtOAc. The organic layer was washed with brine, then dried over anhydrous MgSO₄. The solvent was distilled out under reduced pressure. Column chromatography (silica gel, EtOAc/hexanes (0% to 70%) yielded the title compound as a yellow solid.

¹H-NMR (300 Hz, d₆-DMSO) δ 4.26 (ABq, 2H, $J_{AB}$=10.7 Hz, $\Delta v_{AB}$=18 Hz), 5.65 (s, 2H), 6.24 (t, 2H, J=2.1 Hz), 7.20 (d, 2H, J=8.6 Hz), 7.34 (t, 2H, J=2.2 Hz), 7.55 (d, 2H, J=8.6 Hz), 7.90 (s, 1H), 8.02 (s, 1H).

Example 79

1-[5,6-Dichloro-2-(2,2,2-trifluoro-ethyl)-benzoimidazol-1-yl]-butan-2-one Oxime

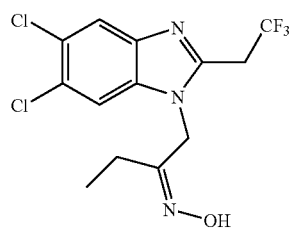

1-[5,6-Dichloro-2-(2,2,2-trifluoro-ethyl)-benzoimidazol-1-yl]-butan-2-one (339 mg, 1 mmol), hydroxylamine hydrochloride (227.5 mg, 3.25 mmol) and pyridine (3 mL) in ethanol (3 mL) were heated to 70° C. for 5 hours. The reaction mixture was then poured into water and extracted with EtOAc. The organic layer was washed with 15% NaCl, brine, then dried over anhydrous $MgSO_4$. The solvent was distilled out under reduced pressure. Column chromatography (silica gel, EtOAc/hexanes (0% to 60%) yielded the title compound as a white solid.

MS m/z (M−H) 354.

Example 80

1-(4-Benzyloxy-benzyl)-5,6-dichloro-2-(2,2,2-trifluoro-ethyl)-1H-benzoimidazole

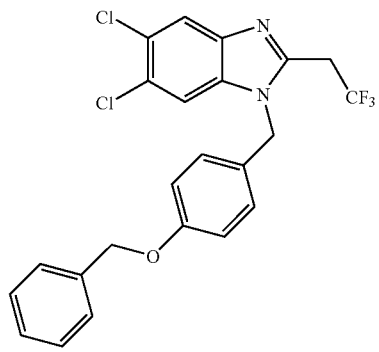

NaH (60%) (120 mg, 3 mmol) was added into a solution of dichloro-2-(2,2,2-trifluoro-ethyl)-1H-benzoimidazole. 5,6-Dichloro-2-(2,2,2-trifluoro-ethyl)-1H-indole (538 mg, 2 mmol) in DMF (5 ml) at 0° C. The resulting mixture was stirred at 0° C. for half hour. 4-benzyloxy-benzyl chloride (698 mg, 3 mmol) and potassium iodide (498 mg, 3 mmol) were then added to the reaction mixture at 0° C. The reaction temperature was raised to 25° C. and then the reaction mixture was stirred for 18 hours. $NH_4Cl$ (aq.) was added and extracted with EtOAc. The organic layer was washed with brine, then dried over anhydrous $MgSO_4$. The solvent was distilled out under reduced pressure. Column chromatography (silica gel, EtOAc/hexanes (0% to 70%) yielded the title compound as a yellow solid.

MS m/z (M−H) 463.

Example 81

5,6-Dichloro-1-(4-methoxy-benzyl)-2-(2,2,2-trifluoro-ethyl)-1H-benzoimidazole

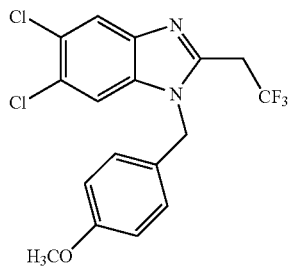

NaH (60%) (120 mg, 3 mmol) was added into a solution of dichloro-2-(2,2,2-trifluoro-ethyl)-1H-benzoimidazole. 5,6-Dichloro-2-(2,2,2-trifluoro-ethyl)-1H-indole (538 mg, 2 mmol) in DMF (5 ml) at 0° C. The resulting mixture was stirred at 0° C. for half hour. 4-methoxy-benzyl chloride (470 mg, 3 mmol) and potassium iodide (498 mg, 3 mmol) were then added to the reaction mixture at 0° C. The reaction temperature was raised to 25° C. and then the reaction mixture was stirred for 18 hours. $NH_4Cl$ (aq.) was added and extracted with EtOAc. The organic layer was washed with brine, then dried over anhydrous $MgSO_4$. The solvent was distilled out under reduced pressure. Column chromatography (silica gel, EtOAc/hexanes (0% to 70%), solvent was distilled under reduced pressure and the residue was dissolved in DCM. The resulting solution was diluted with hexane. The precipitate was filtered and dried to yield the title compound as an off-white solid.

MS m/z (M+H) 389; (M−H) 387.

Example 82

1-[5,6-Dichloro-2-(2,2,2-trifluoro-ethyl)-benzoimidazol-1-yl]-butan-2-ol

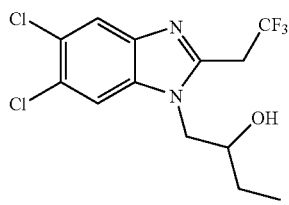

Sodium borohydride (11.16 mg, 0.2949 mmol) was added into methanol (5 mL). After the bubbling ceased, 1-[5,6-dichloro-2-(2,2,2-trifluoro-ethyl)-benzoimidazol-1-yl]-butan-2-one (19170-168) (100 mg, 0.2949 mmol) was added. The resulting mixture was stirred at room temperature for 1 hour. The resulting mixture was poured into water and then extracted with EtOAc. The organic layer was dried over anhydrous $MgSO_4$. The solvent was distilled out under reduced pressure to yield the title compound as an off-white solid.

MS m/z (M+H) 341.

Example 83

1-(4-Bromo-benzyl)-5,6-dichloro-2-(2,2,2-trifluoro-ethyl)-1H-benzoimidazole

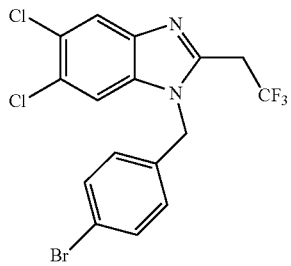

NaH (60%) 120 mg, 3 mmol) was added into a solution of dichloro-2-(2,2,2-trifluoro-ethyl)-1H-benzoimidazole. 5,6-Dichloro-2-(2,2,2-trifluoro-ethyl)-1H-indole (538 mg, 2 mmol) in DMF (5 ml) at 0° C. The resulting mixture was stirred at 0° C. for half hour. 4-bromo-benzyl bromide (749.8 mg, 3 mmol) and potassium iodide (498 mg, 3 mmol) were then added to the reaction mixture at 0° C. The reaction temperature was raised to 25° C. and then the reaction mixture was stirred for 18 hours. NH$_4$Cl (aq.) was added and then the reaction mixture was extracted with EtOAc. The organic layer was washed with brine, then dried over anhydrous MgSO$_4$. Solvent was distilled out under reduced pressure. Column chromatography (silica gel, EtOAc/hexanes (0% to 60%) yielded the title compound as a solid light brown solid.

MS m/z (M+H) 438.

Example 84

4-[5,6-Dichloro-2-(2,2,2-trifluoro-ethyl)-benzoimidazol-1-ylmethyl]-benzoic Acid Ethyl Ester

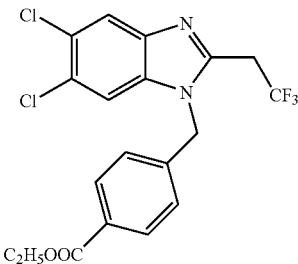

NaH (60%) 120 mg, 3 mmol) was added into a solution of dichloro-2-(2,2,2-trifluoro-ethyl)-1H-benzoimidazole. 5,6-Dichloro-2-(2,2,2-trifluoro-ethyl)-1H-indole (538 mg, 2 mmol) in DMF (5 ml) at 0° C. The resulting mixture was stirred at 0° C. for half hour. Ethyl 4-(bromomethyl)-benzoate (729.3 mg, 3 mmol) and potassium iodide (498 mg, 3 mmol) were then added to the reaction mixture at 0° C. The reaction temperature was raised to 25° C. and then the reaction mixture was stirred for 18 hours. NH$_4$Cl (aq.) was added and extracted with EtOAc. The organic layer was washed with brine, then dried over anhydrous MgSO$_4$. The solvent was distilled out under reduced pressure. Column chromatography (silica gel, EtOAc/hexanes (0% to 60%) yielded the title compound as an off-white solid.

$^1$H-NMR (300 Hz, d$_6$-DMSO) δ 1.29 (t, 3H, J=7.1 Hz), 4.22 (ABq, 2H, J$_{AB}$=10.6 Hz, Δv$_{AB}$=18.4 Hz), 4.29 (q, 2H, J=7.1 Hz), 5.75 (s, 2H), 7.20 (d, 2H, J=8.3 Hz), 7.84 (s, 1H), 7.92 (d, 2H, J=8.4 Hz), 8.03 (s, 1H).

Example 85

1-(2-Bromo-benzyl)-5,6-dichloro-2-(2,2,2-trifluoro-ethyl)-1H-benzoimidazole

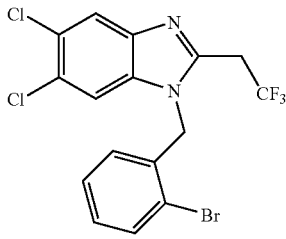

NaH (60%) 120 mg, 3 mmol) was added into a solution of dichloro-2-(2,2,2-trifluoro-ethyl)-1H-benzoimidazole. 5,6-Dichloro-2-(2,2,2-trifluoro-ethyl)-1H-indole (538 mg, 2 mmol) in DMF (5 ml) at 0° C. The resulting mixture was stirred at 0° C. for half hour. Ethyl 4-(bromomethyl)-benzoate (729.3 mg, 3 mmol) and potassium iodide (498 mg, 3 mmol) were then added to the reaction mixture at 0° C. The reaction temperature was raised to 25° C. and then the reaction mixture was stirred for 18 hours. NH$_4$Cl (aq.) was added and extracted with EtOAc. The organic layer was washed with brine, then dried over anhydrous MgSO$_4$. The solvent was distilled out under reduced pressure. Column chromatography (silica gel, EtOAc/hexanes (0% to 60%) yielded the title compound as a white solid.

MS m/z (M+H) 439.

Example 86

1-(5,6-Dimethyl-1H-benzoimidazol-2-yl-)2,2,2-trifluoro-ethanol

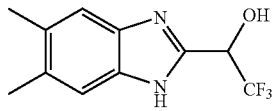

4,5-Dimethyl-benzene-1,2-diamine (5.04 g; 37.0 mmoles) and 3,3,3-trifluoro-2-hydroxy-propionic acid (8.01 g; 55.6 mmoles) were suspended in 6N HCl (9 mL; 54 mmoles) under a nitrogen atmosphere. The reaction was stirred vigorously and heated to 108° C. for 18 hrs, then cooled to room temperature. The reaction was diluted with water (100 mL) and with ethyl acetate (100 mL), then sodium bicarbonate (6.90 g; 81.00 mmoles) was added slowly and in portions to quench the reaction. The aqueous layer was separated and extracted with ethyl acetate (3×40 mL). The extracts were combined, washed with water (30 mL) and brine (30 mL), then dried over Na$_2$SO$_4$. The filtrate was concentrated in vacuo to yield a crude brown solid which was purified by column chromatography (SiO$_2$; 30% ethyl acetate/CH$_2$Cl$_2$) to yield the title compound as an off-white solid.

¹H NMR (400 MHz, CD₃CN) δ 10.51 (br s, 1H), δ 7.37 (br d, 2H), δ 5.36 (q, J=6.9 Hz, 1H), δ 5.16 (brs, 1H), δ 2.35 (s, 6H).
MS calculated for $C_{11}H_{11}F_3N_2O$: 244.08
MS Measured: 245 (M+H); 243 (M−H).

Example 87

1-(5-Chloro-6-fluoro-1H-benzoimidazol-2-yl-)2,2,2-trifluoro-ethanol

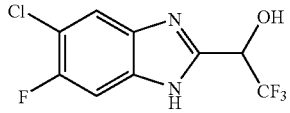

4-Chloro-5-fluoro-benzene-1,2-diamine (5.20 g; 32.4 mmoles) and 3,3,3-trifluoro-2-hydroxy-propionic acid (7.00 g; 48.6 mmoles) were suspended in 6N HCl (9 mL; 54 mmoles) under a nitrogen atmosphere. The reaction was stirred vigorously and heated to 108° C. for 18 hrs, then cooled to room temperature. The reaction was diluted with water (100 mL) and with ethyl acetate (100 mL), then sodium bicarbonate (6.90 g; 81.00 mmoles) was added slowly and in portions to quench the reaction. The aqueous layer was separated and extracted with ethyl acetate (3×40 mL). The extracts were combined, washed with water (30 mL) and brine (30 mL), then dried over $Na_2SO_4$. The filtrate was concentrated in vacuo to yield a crude brown solid which was then purified by column chromatography ($SiO_2$; 30% ethyl acetate/$CH_2Cl_2$) to yield the title compound as an off-white solid.
¹H NMR (400 MHz, CD₃CN) δ 7.74 (d, J=6.7 Hz, 1H), δ 7.49 (d, J=9.5, 1H), δ 5.41 (q, J=6.8 Hz, 1H), δ 5.16 (br s, 1H), δ 2.35 (s, 6H)
MS calculated for $C_9H_5ClF_4N_2O$: 268.00
MS measured: 269 (M+H); 267 (M−H).

Example 88

1-(5-Chloro-6-fluoro-1H-benzoimidazol-2-yl-)2,2,2-trifluoro-ethanone

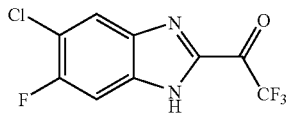

1-(5-Chloro-6-fluoro-1H-benzoimidazol-2-yl)-2,2,2-trifluoro-ethanol (0.34 g; 1.3 mmoles), 4-methoxy-2,2,6,6-tetramethyl-1-piperdinyloxy free radical (4-methoxy-TEMPO free radical; 6.1 mg; 0.03 mmoles) and potassium bromide (KBr; 18 mg; 0.15 mmoles) were dissolved in THF (3.5 mL). The reaction mixture was stirred while cooled to −10° C., after 10 min. a sodium hypochlorite solution (bleach; 10-13% aqueous; 3.0 mL; 5.04 mmoles) was added and allowed to stir for 15 min., then warmed to room temperature and stirred for 15 min. The reaction mixture was diluted with water (20 mL) and ethyl acetate (30 mL), the layers were separated and the aqueous layer was extracted with ethyl acetate (3×30 mL). The extracts were combined and washed with water (30 mL) and brine (40 mL), then dried over $Na_2SO_4$. The filtrate was concentrated in vacuo and purified by column chromatography ($SiO_2$; 100% diethyl ether) to yield the title compound as a light yellow solid.
¹H NMR (400 MHz, CD₃CN) δ 7.83 (d, J=6.7 Hz, 1H), δ 7.77 (d, J=9.5 Hz, 1H)
MS calculated for $C_9H_3ClF_4N_2O$: 265.99
MS Measured: 265, 267 (M−H).

Example 89

1-(5,6-Difluoro-1H-benzoimidazol-2-yl-)2,2,2-trifluoro-ethanol

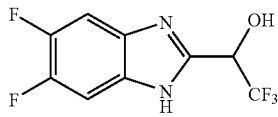

4,5-Difluoro-benzene-1,2-diamine (4.98 g; 34.5 mmoles) and 3,3,3-trifluoro-2-hydroxy-propionic acid (7.48 g; 51.9 mmoles) were suspended in 6N HCl (8 mL; 48 mmoles) under a nitrogen atmosphere. The reaction was stirred vigorously and heated to 108° C. for 18 hrs, then cooled to room temperature. The reaction was diluted with water (100 mL) and with ethyl acetate (100 mL), then sodium bicarbonate (6.05 g; 72.0 mmoles) was added slowly and in portions to quench the reaction. The aqueous layer was separated and extracted with ethyl acetate (3×40 mL). The extracts were combined, washed with water (30 mL) and brine (30 mL), then dried over $Na_2SO_4$. The filtrate was concentrated in vacuo to yield a crude brown solid which was then purified by column chromatography ($SiO_2$; 30% ethyl acetate/$CH_2Cl_2$) to yield the title compound as a pale orange solid.
¹H NMR (400 MHz, CD₃CN) δ 7.35 (m, 1H), δ 7.21 (m, 1H), δ 5.44 (q, J=6.8 Hz, 1H)
MS calculated for $C_9H_5F_5N_2O$: 252.03
MS measured: 253 (M+H); 251 (M−H).

Example 90

1-(5,6-DiChloro-1H-benzoimidazol-2-yl-)2,2,2-trifluoro-ethanol

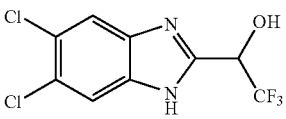

4,5-Dichloro-benzene-1,2-diamine (8.50 g; 48.0 mmoles) and 3,3,3-trifluoro-2-hydroxy-propionic acid (10.59 g; 73.52 mmoles) were suspended in 6N HCl (19 mL; 114 mmoles) under a nitrogen atmosphere. The reaction was stirred vigorously and heated to 108° C. for 18 hrs, then cooled to room temperature. The reaction was diluted with water (200 mL) and with ethyl acetate (200 mL), then sodium bicarbonate (6.05 g; 72.0 mmoles) was added slowly and in portions to quench the reaction. The aqueous layer was separated and extracted with ethyl acetate (3×80 mL). The extracts were combined, washed with water (60 mL) and brine (60 mL), then dried over $Na_2SO_4$. The filtrate was concentrated in vacuo to yield a crude brown solid which was then purified by column chromatography (SiO$_2$; 30% ethyl acetate/CH$_2$Cl$_2$) to yield the title compound as a brown solid.

$^1$H NMR (400 MHz, CD$_3$CN) δ 7.80 (s, 2H), δ 5.43 (q, J=6.8 Hz, 1H)

MS calculated for C$_9$H$_5$Cl$_2$F$_3$N$_2$O: 283.97

MS measured: 285, 287 (M+H); 283, 285 (M−H).

Example 91

Diastereomers of 3,3,3-Trifluoro-2-methoxy-2-phenyl-propionic Acid 1-(5,6-dichloro-1H-benzamidazol-2-yl)-2,2,2-trifluoro-1-methyl-ethyl Ester

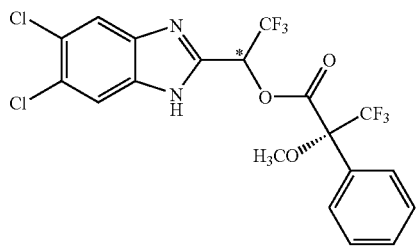

2-(5,6-Dichloro-1H-benzoimidazol-2-yl)-1,1,1-trifluoro-propan-2-ol (2.24 g; 7.86 mmoles) was dissolved in pyridine (1.4 mL; 17 mmoles) and THF (20 mL), then stirred under a nitrogen atmosphere. (R)-(−)-α-Methoxy-α-(trifluoromethyl)phenylacetyl chloride (1.85 mL; 9.91 mmoles) was added to the reaction mixture and stirred at room temperature for 18 hrs. The reaction mixture was concentrated in vacuo, and then dissolved in 50% diethyl ether/ethyl acetate (50 mL), then washed with water (30 mL). The aqueous layer was extracted with 50% diethyl ether/ethyl acetate (3×50 mL), the extracts were combined, washed with water (30 mL), brine (50 mL) and dried over Na$_2$SO$_4$. The filtrate was concentrated in vacuo then purifed by column chromatography (SiO$_2$; 100% CH$_2$Cl$_2$) to yield the title compound as a yellow oil, as a mixture of diasteriomers. The diasteriomeric mixture was separated by chiral chromatography (Chiralpak AD; 30% isopropanol/heptane), to yield a white foam (peak 1; retention time: 9.04 min. (@ 100 mL/min)) and an off white solid (peak 2; retention time: 19.04 min. (@ 100 ml/min)).

Peak 1:

$^1$H NMR (300 MHz, CD$_3$CN) δ 11.19 (br s, 1H), δ 7.87 (br s, 1H), δ 7.77 (br s, 1H), δ 7.51-7.37 (series of m, 5H), δ 6.76 (q, J=6.4, 1H), δ 3.61 (s, 3H)

MS calculated for C$_{19}$H$_{12}$Cl$_2$F$_6$N$_2$O$_3$: 500.01

MS measured: 501, 503 (M+H); 499, 501 (M−H).

[α]$_D^{20}$=−22; c=0.306 in methanol.

Peak 2

$^1$H NMR (300 MHz, CD$_3$CN) δ 11.18 (br s, 1H), δ 7.91-7.81 (br m, 2H), δ 7.58-7.45 (series of m, 5H), δ 6.78 (q, J=6.3, 1H), δ 3.53 (s, 3H)

MS calculated for C$_{19}$H$_{12}$Cl$_2$F$_6$N$_2$O$_3$: 500.01

MS measured: 501, 503 (M+H); 499, 501 (M−H)

[α]$_D^{20}$=−49; c=0.314 in methanol.

Example 92

1-(5,6-DiChloro-1H-benzoimidazol-2-yl)-2,2,2-trifluoro-ethanone

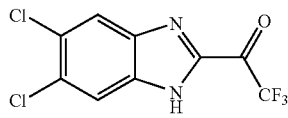

1-(5,6-Dichloro-1H-benzoimidazol-2-yl)-2,2,2-trifluoro-ethanol (0.29 g; 1.00 mmole), 4-methoxy-2,2,6,6-tetramethyl-1-piperdinyloxy free radical (4-methoxy-TEMPO free radical; 4.4 mg; 0.03 mmoles) and potassium bromide (KBr; 13 mg; 0.11 mmoles) were dissolved in THF (2.9 mL). The reaction mixture was stirred while cooled to −10° C., after 10 min. a sodium hypochlorite solution (bleach; 10-13% aqueous; 2.10 mL; 3.53 mmoles) was added and allowed to stir for 15 min., then warmed to room temperature and stirred for 15 min. The reaction mixture was diluted with water (20 mL) and ethyl acetate (30 mL), the layers were separated and the aqueous layer was extracted with ethyl acetate (3×30 mL). The extracts were combined and washed with water (30 mL) and brine (40 mL), then dried over Na$_2$SO$_4$. The filtrate was concentrated in vacuo and purified by column chromatography (SiO$_2$; 100% ether) to yield the title compound as a light yellow solid.

$^1$H NMR (400 MHz, CD$_3$CN) δ 8.01 (s, 1H), δ 7.83 (br s, 2H)

MS calculated for C$_9$H$_3$Cl$_2$F$_3$N$_2$O: 281.96

MS measured: 281, 283 (M−H).

Example 93

1-(5,6-Dichloro-1H-benzoimidazol-2-yl)-2,2,2-trifluoro-ethanone Oxime

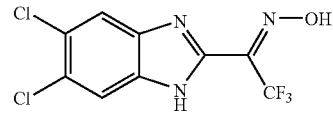

1-(5,6-Dichloro-1H-benzoimidazol-2-yl)-2,2,2-trifluoro-ethanone (0.3005 g; 1.062 mmoles) and hydroxylamine hydrochloride (0.2389 g, 3.438 mmoles) were suspended in pyridine (3 mL) and ethanol (3 mL), then heated to 70° C. for 3 hrs. The reaction mixture was cooled to room temperature, water was water (50 mL) and the reaction mixture was then extracted with ethyl acetate (3×40 ml). The extracts were combined then washed with water (20 mL), brine (30 mL) and dried over Na$_2$SO$_4$. The filtrate was concentrated in vacuo and purifed by column chromatography (SiO$_2$; 30% ethyl acetate/CH$_2$Cl$_2$) to yield the title compound as an off-white solid, as a mixture of oxime E and Z isomers.

$^1$H NMR (400 MHz, d$_6$-DMSO) δ 8.33-7.64 (series of s, 2H)

MS calculated for C$_9$H$_4$Cl$_2$F$_3$N$_2$O: 296.96

MS measured: 296, 298 (M−H).

Example 94

1-(5-Chloro-6-methyl-1H-benzoimidazol-2-yl-)2,2,2-trifluoro-ethanol

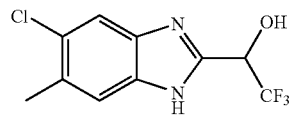

4-Chloro-5-methyl-benzene-1,2-diamine (5.06 g; 32.3 mmoles) and 3,3,3-trifluoro-2-hydroxy-propionic acid (7.11 g; 49.4 mmoles) were suspended in 6N HCl (12 mL; 72 mmoles) under a nitrogen atmosphere. The reaction was stirred vigorously and heated to 108° C. for 18 hrs, then cooled to room temperature. The reaction was diluted with water (100 mL) and with ethyl acetate (100 mL), then sodium bicarbonate (9.12 g; 109 mmoles) was added slowly and in portions to quench the reaction. The aqueous layer was separated and extracted with ethyl acetate (3×40 mL). The extracts were combined, washed with water (30 mL) and brine (30 mL), then dried over $Na_2SO_4$. The filtrate was concentrated in vacuo to yield a crude brown solid which was then purified by column chromatography ($SiO_2$; 30% ethyl cetate/$CH_2Cl_2$) to yield the title compound as a purple/brown solid.

$^1$H NMR (400 MHz, $CD_3CN$) δ 7.65 (s, 1H), δ 7.52 (s, 1H), δ 5.40 (q, J=6.9 Hz, 1H), δ 2.46 (s, 3H)

MS calculated for $C_{10}H_8ClF_3N_2O$: 264.03

MS measured: 265, 267 (M+H); 263, 265 (M−H).

Example 95

1-(5-Chloro-6-methyl-1H-benzoimidazol-2-yl-)2,2,2-trifluoro-ethanone

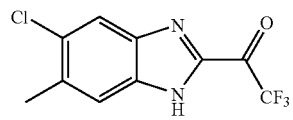

1-(5-Chloro-6-methyl-1H-benzoimidazol-2-yl)-2,2,2-trifluoro-ethanol (0.33 g; 1.2 mmole), 4-methoxy-2,2,6,6-tetramethyl-1-piperdinyloxy free radical (4-methoxy-TEMPO free radical; 5.6 mg; 0.03 mmoles) and potassium bromide (KBr; 22 mg, 0.18 mmoles) were dissolved in THF (3.5 mL). The reaction mixture was stirred while cooled to −10° C., after 10 min. a sodium hypochlorite solution (bleach; 10-13% aqueous; 3.0 mL; 5.0 mmoles) was added and the reaction mixture was allowed to stir for 15 min., then warmed to room temperature and stirred for 15 min. The reaction mixture was diluted with water (20 mL) and ethyl acetate (30 mL), the layers were separated and the aqueous layer was extracted with ethyl acetate (3×30 mL). The extracts were combined and washed with water (30 mL) and brine (40 mL), then dried over $Na_2SO_4$. The filtrate was concentrated in vacuo and then purified by column chromatography ($SiO_2$; 100% diethyl ether) to yield the title compound as a white solid.

$^1$H NMR (400 MHz, $CD_3CN$) δ 7.86 (br s, 1H), δ 7.69 (br s, 1H), δ 7.54 (br s, 1H), δ 2.47 (s, 3H)

MS calculated for $C_{10}H_6ClF_3N_2O$: 262.01

MS measured: 261, 263 (M−H).

Example 96

1-(5-1H-benzoimidazol-2-yl-)2,2,2-trifluoro-ethanol

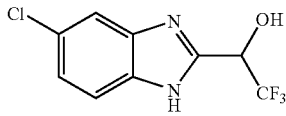

4-Chloro-benzene-1,2-diamine (2.02 g; 14.2 mmoles) and 3,3,3-trifluoro-2-hydroxy-propionic acid (3.10 g; 21.5 mmoles) were suspended in 6N HCl (5 mL; 30 mmoles) and water (4 mL) under a nitrogen atmosphere. The reaction was stirred vigorously and heated to 108° C. for 18 hrs, then cooled to room temperature. The reaction was diluted with water (400 mL) and with ethyl acetate (500 mL), then sodium bicarbonate (3.83 g; 45.6 mmoles) was added slowly and in portions to quench the reaction. The aqueous layer was separated and extracted with ethyl acetate (3×30 mL). The extracts were combined, washed with water (30 mL) and brine (30 mL), then dried over $Na_2SO_4$. The filtrate was concentrated in vacuo to yield a crude brown solid which was then purified by column chromatography ($SiO_2$; 30% ethyl acetate/$CH_2Cl_2$) to yield the title compound as a tan solid.

$^1$H NMR (400 MHz, $CD_3CN$) δ 7.65 (n d, J=1.5, 1H), δ 7.58 (d, J=8.6, 1H), δ 7.27 (dd, J=6.6, 2.0, 3H) δ 5.42 (q, J=6.9 Hz, 1H)

MS calculated for $C_9H_6ClF_3N_2O$: 250.01

MS measured: 251, 253 (M+H); 249, 251 (M−H).

Example 97

2-(2,2,2-Trifluoro-1-hydroxy-ethyl)-6-trifluoromethyl-1H-benzoimdazole-5-carbonitrile

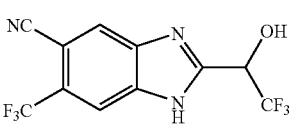

4,5-Diamino-2-trifluoromethyl-benzonitrile (4.14 g; 20.6 mmoles) and 3,3,3-trifluoro-2-hydroxy-propionic acid (4.50 g; 31.2 mmoles) were suspended in 6N HCl (7 mL; 42 mmoles) under a nitrogen atmosphere. The reaction was stirred vigorously and heated to 108° C. for 18 hrs, then cooled to room temperature. The reaction was diluted with water (100 mL) and with ethyl acetate (100 mL), then sodium bicarbonate (5.19 g; 62.0 mmoles) was added slowly and in portions to quench the reaction. The aqueous layer was separated and extracted with ethyl acetate (3×40 mL). The extracts were combined, washed with water (30 mL) and brine (30 mL), then dried over $Na_2SO_4$. The filtrate was concentrated in vacuo to yield a crude dark solid which was then purified by column chromatography ($SiO_2$; 30% ethyl acetate/$CH_2Cl_2$) to yield the title compound as a dark brown solid.

$^1$H NMR (400 MHz, $CD_3CN$) δ 8.27 (s, 1H), δ 8.14 (s, 1H), 85.54 (q, J=6.9 Hz, 1H)

MS calculated for $C_{11}H_5F_6N_3O$: 309.03

MS measured: 310 (M+H); 308 (M−H).

Example 98

1-(5,6-Dinitro-1H-benzoimidazol-2-yl-)2,2,2-trifluoro-ethanol

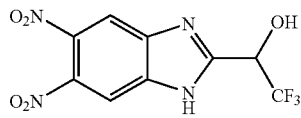

4,5-Dinitro-benzene-1,2-diamine (2.01 g; 10.2 mmoles) and 3,3,3-trifluoro-2-hydroxy-propionic acid (2.22 g; 15.4 mmoles) were suspended in 6N HCl (5 mL; 30 mmoles) and water (4 mL) under a nitrogen atmosphere. The reaction was stirred vigorously and heated to 108° C. for 18 hrs, then cooled to room temperature. The reaction was diluted with water (40 mL) and with ethyl acetate (40 mL), then sodium bicarbonate (3.79 g; 45.0 mmoles) was added slowly and in portions to quench the reaction. The aqueous layer was separated and extracted with ethyl acetate (3×30 mL). The extracts were combined, washed with water (30 mL) and brine (40 mL), then dried over $Na_2SO_4$. The filtrate was concentrated in vacuo to yield a crude brown solid which was then purified by column chromatography ($SiO_2$; 30% ethyl acetate/$CH_2Cl_2$) to yield the title compound as a brown solid.

$^1$H NMR (400 MHz, $CD_3CN$) δ 8.29 (s, 2H), δ 5.55 (q, J=6.8, 1H)

MS calculated for $C_9H_5F_3N_4O_5$: 306.16

MS measured: 305 (M−H).

Example 99

1-(5,6-Dimethoxy-1H-benzoimidazol-2-yl-)2,2,2-trifluoro-ethanol

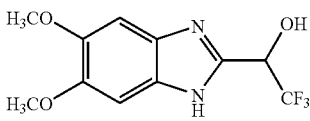

4,5-Dimethoxy-benzene-1,2-diamine (2.02 g; 12.0 mmoles) and 3,3,3-trifluoro-2-hydroxy-propionic acid (2.67 g; 18.5 mmoles) were suspended in 6N HCl (5 mL; 30 mmoles) and water (4 mL) under a nitrogen atmosphere. The reaction was stirred vigorously and heated to 108° C. for 18 hrs, then cooled to room temperature. The reaction was diluted with water (40 mL) and with ethyl acetate (40 mL), then sodium bicarbonate (3.84 g; 46.0 mmoles) was added slowly and in portions to quench the reaction. The aqueous layer was separated and extracted with ethyl acetate (3×30 mL). The extracts were combined, washed with water (30 mL) and brine (40 mL), then dried over $Na_2SO_4$. The filtrate was concentrated in vacuo to yield a crude dark orange solid which was then purified by column chromatography ($SiO_2$; 30% ethyl acetate/$CH_2Cl_2$) to yield the title compound as a bright orange solid.

$^1$H NMR (400 MHz, $CD_3CN$) δ 7.15 (br s, 1H), δ 7.06 (br s, 1H), δ 5.34 (q, J=6.8, 1H)

MS calculated for $C_{11}H_{11}F_3N_2O_3$: 267.07

MS measured: 277 (M+H); 275 (M−H).

Example 100

3-(5,6-Dichloro-2-1H-benzoimidazol-2-yl)-1,1,1-trifluoro-2-methyl-propan-2-ol

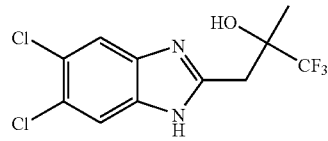

4,5-Dichloro-benzene-1,2-diamine (0.53 g; 3.0 mmoles) and 4,4,4-trifluoro-3-hydroxy-3-methyl-butyric acid (0.78 g; 4.5 mmoles) were suspended in 6N HCl (4 mL; 24 mmoles) and water (4 mL) under a nitrogen atmosphere. The reaction was stirred vigorously and heated to 108° C. for 18 hrs, then cooled to room temperature. The reaction was diluted with water (25 mL) and with ethyl acetate (30 mL), then sodium bicarbonate (7.59 g; 90.3 mmoles) was added slowly and in portions to quench the reaction. The aqueous layer was separated and extracted with ethyl acetate (3×20 mL). The extracts were combined, washed with water (20 mL) and brine (20 mL), then dried over $Na_2SO_4$. The filtrate was concentrated in vacuo to yield a crude brown solid which was then purified by column chromatography ($SiO_2$; 100% $CH_2Cl_2$) to yield the title compound as a light orange solid.

$^1$H NMR (400 MHz, $CD_3CN$) δ 7.74 (s, 2H), δ 3.28 (d, J=15, 1H), δ 3.15 (d, J=15, 1H), δ 1.37 (s, 3H)

MS calculated for $C_{11}H_{19}Cl_2F_3N_2O$: 312.00

MS measured: 313, 315 (M+H); 311, 313 (M−H).

Example 101

5,6-Dichloro-2-(1,2,22-tetrafluoro-ethyl)-1H-benzoimidazole

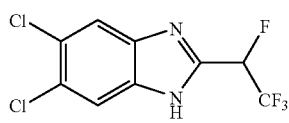

4,5-Dichloro-benzene-1,2-diamine (2.03 g; 11.5 mmoles) and 2,3,3,3-tetrafluoro-propionic acid (1.99 g; 13.6 mmoles) were suspended in 6N HCl (5 mL; 30 mmoles) under a nitrogen atmosphere. The reaction was stirred vigorously and heated to 108° C. for 18 hrs, then cooled to room temperature. The reaction was diluted with water (60 mL) and with ethyl acetate (60 mL), then sodium bicarbonate (4.02 g; 47.9 mmoles) was added slowly and in portions to quench the reaction. The aqueous layer was separated and extracted with ethyl acetate (3×30 mL). The extracts were combined, washed with water (30 mL) and brine (30 mL), then dried over $Na_2SO_4$. The filtrate was concentrated in vacuo to yield a crude brown solid. A sample of the crude brown solid was purified by column chromatography ($SiO_2$; 100% $CH_2Cl_2$) to yield the title compound as a light orange solid.

$^1$H NMR (400 MHz, $CD_3CN$) δ 7.65 (s, 1H), δ 6.28 (dq, J=37, 6.0 Hz, 1H)

MS calculated for $C_9H_5Cl_2F_4N_2$: 285.97

MS measured: 287, 289 (M+H); 285, 287 (M−H).

Example 102

5,6-Dichloro-2-(pentafluoroethyl)-1H-benzoimidazole

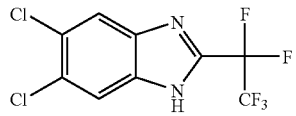

4,5-Dichloro-benzene-1,2-diamine (2.01 g; 11.4 mmoles) and 2,2,3,3,3-pentafluoro-propionic acid (1.80 mL; 17.3 mmoles) were suspended in 6N HCl (10 mL; 60 mmoles) under a nitrogen atmosphere. The reaction was stirred vigorously and heated to 108° C. for 18 hrs, then cooled to room temperature. The reaction was diluted with water (60 mL) and with ethyl acetate (60 mL), then sodium bicarbonate (7.59 g; 90.3 mmoles) was added slowly and in portions to quench the reaction. The aqueous layer was separated and extracted with ethyl acetate (3×30 mL). The extracts were combined, washed with water (30 mL) and brine (30 mL), then dried over $Na_2SO_4$. The filtrate was concentrated in vacuo to yield a crude brown solid which was then purified by column chromatography ($SiO_2$; 100% $CH_2Cl_2$) to yield the title compound as a light tan solid.

$^1$H NMR (400 MHz, $CD_3CN$) δ 7.94 (s, 2H)

MS calculated for $C_9H_3Cl_2F_5N_2$: 303.96

MS measured: 305, 307 (M+H); 303, 305 (M−H).

Example 103

4-[5,6-Dichloro-2-(trifluoro-ethyl)-benzoimidazol-1-ylmethyl]-benzaldehyde

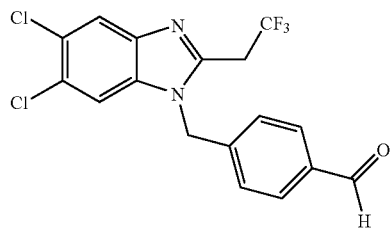

4-[5,6-Dichloro-2-(2,2,2-trifluoro-ethyl)-benzoimidazol-1-ylmethyl]-benzonitrile (0.4079 g; 1.0617 mmoles) was suspended in $CH_2Cl_2$ (3 mL), treated with 1.5 M diisobutylaluminium hydride in toluene (1.42 mL; 2.13 mmoles) and stirred at room temperature for 3 hrs. The reaction mixture was quenched with saturated Rochelle's salt solution (1 mL) and stirred overnight, then filtered through a pad of Celite. The filtrate was diluted with ethyl acetate (30 mL), washed with water (20 mL), brine and dried over $Na_2SO_4$. The filtrate was concentrated in vacuo and then purified by column chromatography ($SiO_2$; 100% $CH_2Cl_2$) to yield the title compound as a yellow oil.

MS calculated for $C_{17}H_{11}Cl_2F_3N_2O$: 389.02

MS measured: 389, 387 (M+H); 385, 387 (M−H).

Example 104

(+)-1-(5,6-DiChloro-1H-benzoimidazol-2-yl-)2,2,2-trifluoro-ethanol

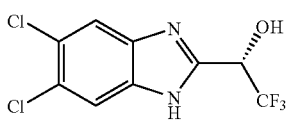

A solution of "Peak 1" prepared as in Example 91 (136 mg; 0.27 mmoles) was suspended in a mixture of dioxane and water (10 mL, 4:1) and treated with NaOH (0.5 mL; 2 mmoles). The reaction was stirred vigorously and heated to 50° C. for 30 min, then cooled to room temperature. The reaction was diluted with water (50 mL) and 1 N HCl (3 mL, 3 mmol). The resulting white precipitate was collected by suction filtration, dissolved in ethyl acetate and then purified by flash chromatography ($SiO_2$, 30% ethyl acetate/dcm) to yield the title compound as a white solid.

$^1$H NMR (400 MHz, $CD_3CN$) δ 7.80 (s, 2H), δ 5.43 (q, J=6.8 Hz, 1H)

MS calculated for $C_9H_5Cl_2F_3N_2O$: 283.97

MS measure: 285, 287 (M+H); 283, 285 (M−H).

$[\alpha]_D^{20}$=+29; c=0.196 in MeOH.

Example 105

(−)-1-(5,6-DiChloro-1H-benzoimidazol-2-yl-)2,2,2-trifluoro-ethanol

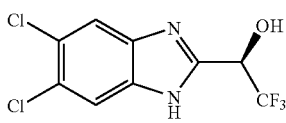

A solution of "Peak 2" prepared as in Example 91 (103 mg; 0.21 mmoles) was suspended in a mixture of dioxane and water (10 mL, 4:1) and treated with NaOH (0.5 mL; 2 mmoles). The reaction was stirred vigorously and heated to 50° C. for 30 min, then cooled to room temperature. The reaction was diluted with water (50 mL) and 1 N HCl (3 mL, 3 mmol). The resulting white precipitate was collected by suction filtration, dissolved in ethyl acetate and then purified by flash chromatography ($SiO_2$, 30% ethyl acetate/dcm) to yield the title compound as a white solid.

$^1$H NMR (400 MHz, $CD_3CN$) δ 7.80 (s, 2H), δ 5.43 (q, J=6.8 Hz, 1H)

MS calculated for $C_9H_5Cl_2F_3N_2O$: 283.97

MS measured: 285, 287 (M+H); 283, 285 (M−H).

$[\alpha]_D^{20}$=−27; c=0.183 in MeOH.

Example 106

5,6-Dichloro-2-(2,2,2-trifluoro-ethyl)-1H-benzoimidazole

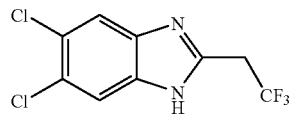

4,5-Dichloro-benzene-1,2-diamine (10.0114 g; 56.5520 mmoles) and 3,3,3-trifluoro-propionic acid (7.5 mL; 84.9 mmoles) were combined with 6N HCl (20 mL; 120 mmoles) and heated to 108° C. for 18 hrs. The reaction mixture was cooled to room temperature, diluted with ethyl acetate (200 mL) and water (200 mL), then then sodium bicarbonate (15.15 g; 180.3 mmoles) was added slowly and in portions to quench the reaction. The aqueous layer was separated and extracted with ethyl acetate (3×60 mL). The extracts were combined, washed with water (60 mL) and brine (60 mL), then dried over $Na_2SO_4$. The filtrate was concentrated in vacuo to yield a crude brown solid. A sample of the crude brown solid was purified by column chromatography ($SiO_2$; 100% $CH_2Cl_2$) to yield the title compound as a light brown solid.

$^1$H NMR (400 MHz, $CD_3CN$) δ 7.78 (s, 2H), δ 3.87 (q, J=10.7 Hz, 2H)

MS calculated for $C_9H_5Cl_2F_3N_2$: 267.98

MS measured: 269, 271 (M+H); 267, 269 (M−H).

Example 107

Ventral Prostate and Seminal Vesicle Weight In Vivo Assay

Immature (approximately 50 g) castrated male Sprague Dawley rats (Charles River) were treated once daily for five days with test compound (usually given orally at 40 mg/kg in a volume of 0.3 mL, in 30% cyclodextrin or 0.5% methylcellulose vehicle) and with testosterone propionate (given subcutaneously by injection at the nape of the neck at 2 mg/kg, in a volume of 0.1 mL in sesame oil). On the sixth day, the rats were euthanized by asphyxiation in carbon dioxide. Ventral prosatates and seminal vesicles were removed and their wet weights determined. Test compound activity was determined as the percent inhibition of testosterone-enhanced tissue weights, with a vehicle-treated control group set to zero percent and a testosterone alone-treated control group set to 100%.

Representative compounds of the present invention were tested according to the procedure described, with results as listed in Table 7 below. A test compound is listed as "active" if the non weight adjusted prostate weight was ≦40 mg or the % Inhibition prostate weight, body weight adjusted was ≧40%@2 mg/day dosage. $ID_{50}$'s, if determined, of ≦15 mg/day also indicated an "active" compound. For the compounds listed in Table 7 as "inactive", one skilled in the art will recognize that said compounds may or may not have shown an effect on prostate and/or vesical weight, rather they are listed herein as "inactive" as they did not meet the specified criteria defined above.

TABLE 7

| ID No. | Activity |
|---|---|
| 1 | active |
| 2 | active |
| 3 | inactive |
| 4 | active |
| 5 | inactive |
| 7 | active |
| 8 | active |
| 9 | active |
| 10 | inactive |
| 12 | active |
| 13 | active |
| 14 | active |
| 15 | active |
| 16 | active |
| 17 | inactive |
| 18 | active |
| 20 | inactive |
| 21 | active |
| 22 | inactive |
| 23 | active |
| 24 | inactive |
| 25 | active |
| 26 | inactive |
| 27 | active |
| 28 | active |
| 29 | active |
| 30 | active |
| 31 | active |
| 33 | active |
| 36 | inactive |
| 37 | active |
| 38 | inactive |
| 39 | active |
| 40 | active |
| 41 | active |
| 42 | inactive |
| 44 | inactive |
| 45 | inactive |
| 46 | inactive |
| 48 | active |
| 49 | inactive |
| 50 | active |
| 51 | active |
| 53 | inactive |
| 54 | inactive |
| 55 | active |
| 56 | inactive |
| 57 | active |
| 58 | active |
| 59 | active |
| 60 | inactive |
| 61 | active |
| 62 | active |
| 63 | active |
| 64 | inactive |
| 65 | inactive |
| 66 | active |
| 68 | active |
| 69 | inactive |
| 70 | inactive |
| 71 | active |
| 72 | inactive |
| 73 | active |
| 74 | inactive |
| 75 | active |
| 76 | active |
| 77 | inactive |
| 78 | active |
| 79 | inactive |
| 80 | active |
| 81 | inactive |
| 82 | active |
| 83 | active |
| 84 | inactive |
| 85 | inactive |
| 86 | inactive |
| 87 | inactive |

TABLE 7-continued

| ID No. | Activity |
| --- | --- |
| 88 | inactive |
| 89 | active |
| 90 | inactive |
| 91 | active |
| 92 | active |
| 93 | active |
| 94 | inactive |
| 95 | inactive |
| 96 | inactive |
| 97 | active |
| 98 | active |
| 99 | active |
| 100 | active |
| 101 | inactive |
| 102 | active |
| 104 | inactive |
| 105 | active |
| 106 | active |
| 107 | active |
| 108 | active |
| 109 | active |
| 110 | active |
| 111 | inactive |
| 112 | active |
| 113 | inactive |
| 114 | active |
| 115 | active |
| 116 | active |
| 117 | active |
| 119 | active |
| 120 | active |
| 121 | active |
| 123 | inactive |
| 124 | active |
| 125 | active |
| 126 | inactive |
| 128 | inactive |
| 129 | inactive |
| 131 | inactive |
| 132 | inactive |
| 133 | active |
| 134 | inactive |
| 135 | inactive |
| 136 | active |
| 137 | active |
| 138 | active |
| 139 | active |
| 140 | inactive |
| 141 | active |
| 142 | inactive |
| 144 | active |
| 146 | active |
| 147 | active |
| 148 | active |
| 149 | active |
| 150 | active |
| 151 | active |
| 152 | active |
| 153 | inactive |
| 154 | inactive |
| 155 | inactive |
| 156 | inactive |
| 157 | inactive |
| 159 | active |
| 160 | active |

Example 108

Ventral Prostate and Levator Ani Weight In Vivo Assay

Mature (150 to 200 g) castrated male Sprague Dawley rats (Charles River) were treated once daily for 14 days with test compound (usually administered by oral gavage at up to the desired dosage, up to 30 mg/kg in a volume of 1 mL, in 30% cyclodextrin or 0.5% methylcellulose vehicle), or with testosterone propionate (administered subcutaneously by injection at the nape of the neck at 5 mg/kg, in a volume of 0.1 mL in sesame oil), or with vehicle (1 mL of 30% cyclodextrin or 0.5% methylcellulose, given orally). On the fifteenth day, the rats were euthanized by asphyxiation in carbon dioxide. Ventral prostates and levator ani muscles were removed and their wet weights determined.

Test compound activity was determined as the percent stimulation of tissue weight, with the vehicle-treated control group set to zero percent and the testosterone alone-treated control group set to 100%. A compound was designated as "active" if it produced greater than or equal to 25% stimulation of levator ani at 30 mg/kg.

Compound #7 was tested according to the above procedure described above, dosing at 30 mg/kg and was measured to be active, according to the above criteria.

Example 109

As a specific embodiment of an oral composition, 100 mg of the Compound #7 prepared as in Example 1 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound selected from
   1-(5,6-dichloro-1H-benzimidazol-2-yl)-2,2,2-trifluoro-ethanol;
   3-(5,6-dichloro-1H-benzimidazol-2-yl)-3-hydroxy-butyronitrile;
   or a pharmaceutically acceptable salt thereof.
2. A pharmaceutical composition comprising a pharmaceutically acceptable carrier and a compound of claim 1.
3. A pharmaceutical composition made by mixing a compound of claim 1 and a pharmaceutically acceptable carrier.

\* \* \* \* \*